US00RE49514E

(19) United States
(12) Reissued Patent
Chopra et al.

(10) Patent Number: US RE49,514 E
(45) Date of Reissued Patent: May 2, 2023

(54) METHODS FOR TREATING PLAGUE

(71) Applicants: The Board of Regents of The University of Texas System, Austin, TX (US); Westport Bio, LLC, Sugar Land, TX (US)

(72) Inventors: Ashok K. Chopra, League City, TX (US); Vladimir L. Motin, League City, TX (US); Eric Rothe, Houston, TX (US)

(73) Assignees: The Board of Regents of the University of Texas System, Austin, TX (US); Westport Bio, LLC, Sugar Land, TX (US)

(21) Appl. No.: 17/023,547

(22) Filed: Sep. 17, 2020

Related U.S. Patent Documents

Reissue of:
(64) Patent No.: 10,076,562
Issued: Sep. 18, 2018
Appl. No.: 15/490,261
Filed: Apr. 18, 2017

U.S. Applications:
(60) Provisional application No. 62/324,528, filed on Apr. 19, 2016.

(51) Int. Cl.
*A61K 39/02* (2006.01)
*A61K 39/00* (2006.01)

(52) U.S. Cl.
CPC ..... *A61K 39/0291* (2013.01); *A61K 39/025* (2013.01); *A61K 2039/53* (2013.01); *A61K 2039/543* (2013.01); *A61K 2039/545* (2013.01); *A61K 2039/70* (2013.01); *C12N 2710/10043* (2013.01); *Y02A 50/30* (2018.01)

(58) Field of Classification Search
CPC ..... A61K 39/0291; A61K 39/025
See application file for complete search history.

(56) References Cited

U.S. PATENT DOCUMENTS 6,261,807 B1 7/2001 Crouzet et al.
9,410,129 B2 8/2016 Ranki et al.
2010/0209451 A1* 8/2010 Clarke ..... A61P 31/12 435/320.1

FOREIGN PATENT DOCUMENTS

WO 2008/045601 A2 4/2008

OTHER PUBLICATIONS

Heath et al., Vaccine 16(No. 11/12):1131-37, 1998.*
Matson et al., BMC Microbiol., 5:38, pp. 1-10, 2005.*
Agar et al., "Deletion of Braun lipoprotein gene (lpp) and curing of plasmid pPCPl dramatically alter the virulence of *Yersinia pestis* CO92 in a mouse model of pneumonic plague," *Microbiology*, 2009; 155:3247-3259.
Alvarez et al., Plant-made subunit vaccine against pneumonic and bubonic plague is orally immunogenic in mice, *Vaccine*; 2006; 24(44):2447-2490.
Bessis et al., "Immune responses to gene therapy vectors: influence on vector function and effector mechanisms," *Gene Ther*, 2004; ll(Suppl 1):S10-17.
Guyton, "Measurement of the respiratory volumes of laboratory animals," *Am J Physiol*, 1947, 150(l):70-77.
Mizel et al., "Flagellin-F1-V fusion protein is an effective plague vaccine in mice and two species of nonhuman primates," *Clin Vaccine Immunol*, 2009; 16(l):21-28.
Pitt, "Nonhuman Primates as a Model for Pneumonic Plague," Proceedings of the Animal Models and Correlates of Protection for Plague Vaccines Workshop, Food and Drug Administration, National Institute of Allergy and Infectious Disease, and Department of Health and Human Services, Oct. 13-14, 2004; 300 pages.
Powell et al., "Design and testing for a nontagged F1-V fusion protein as vaccine antigen against bubonic and pheumonic plague," *Biotechnol Prog*, 2005; 21(5): 1490-1510.
Quenee et al., "*Yersinia pestis caf1* variants and the limits of plague vaccine protection," *Infect Immun.*, 2008; 76:2025-2036.
Quenee et al., "Prevention of pneumonic plague in mice, rats, guinea pigs and non-human primates with clinical grade rV10, rV10-2 or F1-V vaccines," *Vaccine*, 2011, 29:6572-6583.
Rothe, Eric and Chopra, Ashok K. "Evaluation and Production of a Multivalent Adenoviral Plague Vaccine," Grant Abstract, Grant No. AI071634 [online]. National Institute of Allergy and Infectious Diseases, National Institutes of Health, project dates Jul. 1, 2006 to Jun. 30, 2015 [retrieved on May 10, 2018]. Retrieved from the Internet: <URL:http://grantome.com//grant/NIH/R44-AI071634-05>; 3 pgs.
Tao et al., "Mutated and bacteriophage T4 nanoparticle arrayed F1-V immunogens from *Yersinia pestis* as next generation plague vaccines," *PLoS Pathog.*, 2013;9:e1003495.
Welkos et al., "Modified caspase-3 assay indicates correlation of caspase-3 activity with immunity of nonhuman primates to Yersinia pestis infection," *Clin Vaccine Immunol*, 15(7):1134-1137.
"African Green monkey (*Chlorocebus aethiops*) animal model development to evaluate treatment of pneumonic plague," Food and Drug Administration (FDA) Anti-Infective Drugs Advisory Committee Meeting, Apr. 3, 2012, Silver Spring, MD; 68 pages.

(Continued)

*Primary Examiner* — Sharon Turner
(74) *Attorney, Agent, or Firm* — Mueting Raasch Group

(57) ABSTRACT

Provided herein are methods for using compositions that include a fusion protein having a YscF protein domain, a mature F1 protein domain, and a LcrV protein domain. In one embodiment the composition is used to confer immunity to plague, such as pneumonic plague, caused by Yersinia pestis. In one embodiment, the composition is administered to a mucosal surface, such as by an intranasal route. In one embodiment, the administration to a mucosal surface includes a vector that has a polynucleotide encoding a fusion protein, where the fusion protein includes a YscF protein domain, a mature F1 protein domain, and a LcrV protein domain. The administration is followed by a second administration by a different route, such as an intramuscular route. The second administration includes a fusion protein having the same three domains, and in one embodiment the fusion protein is the same one administered to a mucosal surface.

19 Claims, 31 Drawing Sheets

Specification includes a Sequence Listing.

(56) References Cited

OTHER PUBLICATIONS

Agar et al., "Characterization of a mouse model of plague after aerosolization of *Yersinia pestis* CO92," *Microbiology*, Jul. 2008; 154(Pt. 7):1939-1948.
Agar et al., "Characterization of the rat pneumonic plague model: infection kinetics following aerosolization of *Yersinia pestis*CO92," Microbes Infect, 2009; 11:205-214.
Andrews et al., Protective efficacy of recombinant Yersinia outer proteins against bubonic plague caused by encapsulated and nonencapsulated Yersinia pestis, *Infect Immun*, 1999; 67(3):1533-1537.
Anisimov et al., "Amino acid and structural variability of Yersinia pestis LcrV protein," *Infect Genet Evol*, 2010; 10(1):137-145.
Baker et al., "Studies on immunization against plague. I. The isolation and characterization of the soluble antigen of Pasteurella pestis," *J Immunol*, 1952; 68(2):134-145.
Barouch et al., "Immunogenicity of recombinant adenovirus serotype 35 vaccine in the presence of pre-existing anti-Ad5 immunity," *J Immunol*, 2004; 172(10):6290-6297.
Barouch et al., "Adenovirus vector-based vaccines for human immunodeficiency virus type 1," *Hum Gene Ther*, 2005; 16(2):149-156.
Benner et al., "Immune response to Yersinia outer proteins and other Yersinia pestis antigens after experimental plague infection in mice," *Infect Immun*, 1999; 67(4):1922-1928.
Bowie et al., "Deciphering the message in protein sequences: tolerance to amino acid substitutions," *Science*, 1990, 247(4948):1306-1310.
Boyer et al., "Adenovirus-based genetic vaccines for biodefense," *Hum Gene Ther*, 2005; 16(2):157-168.
Byvalov et al., "Effectiveness of revaccinating hamadryas baboons with NISS live dried plague vaccine and fraction I of the plague microbe," *ZH Mikrobiol Epidermiol Immunobiol*, 1984, 4:74-76. In Russian, with English abstract.
Cathelyn et al., "RovA, a global regulator of Yersinia pestis, specifically required for bubonic plague," *PNAS USA*, 2006; 103(36):13514-13519.
Chen et al., "Susceptibility of the langur monkey (Semnopithecus entellus) to experimental plague: pathology and immunity," *J Infect Dis*, 1965; 115(5):456-464.
Chen et al., "Immunity in plague: protection induced in Cercopithecus aethiops by oral administrationof live, attenuated Yersinia pestis," *J Infect Dis*, 1976; 133(3):302-309.
Chen et al., "Fusion protein linkers: property, design and functionality," *Adv Drug Deliv Rev*, 2013; 65(10):1357-1369.
Chiuchiolo et al., Protective immunity against respiratory tract challenge with Yersina pestis in mice immunized with an adenovirus-based vaccine vector expressing V antigen, *J Infect Dis*, 2006; 194(9):1249-1257.
Cornelis, "*Yersinia type*III secretion: send in the effectors," *J Cell Biol.*, 2002; 158:401-408.
Cornelius et al., "Immunization with recombinant V10 protects cynomolgus macaques from lethal pneumonic plague," *Infect Immun*, 2008, 76(12):5588-5597.
Croyle et al., "Nasal delivery of an adenovirus-based vaccine bypasses pre-existing immunity to the vaccine carrier and improves the immune response in mice," *PLoS One*, 2008; 3(10):e3548.
Cui et al., "Genetic variations of live attenuated plague vaccine strains (*Yersinia pestis*EV76 lineage) during laboratory passages in different countries," *Infect Genet Evol.*, 2014; 26:172-179.
Danthinne et al., "Production of first generation adenovirus vectors: a review," *Gene Ther*, 2000; 7(20):1707-1714.
Do et al., "Induction of pulmonary mucosal immune responses with a protein vaccine targeted to the DEC-205/CD205 receptor," *Vaccine*, 2012; 30(45):6359-6367.
Doll et al., "Cat-transmitted fatal pneumonic plague in a person who traveled from Colorado to Arizona," *Am J Trop Med Hyg*, 1994; 51(1):109-114.
Fellows et al., "Characterization of a *Cynomolgus Macaque*Model of Pneumonic Plague for Evaluation of Vaccine Efficacy," *Clin Vaccine Immunol.*, 2015; 22:1070-1078.
Finegold et al., "Studies on the pathogenesis of plague. Blood coagulation and tissue responses of Macaca mulatta following exposure to aerosols of Pasteurella pestis," *Am J Pathol*, 1968; 53(1):99-114.
Goujon et al., "A new bioinformatics analysis tools framework at EMBL-EBI," *Nucleic Acids Res*, 2010; 38:W695-9.
Hackett et al., Antivector and antitransgene host responses in gene therapy, *Curr Opin Mol Ther*, 2000, 2(4):376-382.
Hallett et al., "Pathogenicity and immunogenic efficacy of a live attentuated plaque vaccine in vervet monkeys," *Infect Immun.*, 1973; 8:876-881.
Hu et al., "Crystal structure of TET2-DNA complex: insight into TET-mediated 5mC oxidation," *Cell*, 2013; 155(7):1545-1555.
Jones et al., "Prevention of influenza virus shedding and protection from lethal H1N1 challenge using a consensus 2009 H1N1 HA and NA adenovirus vector vaccine," *Vaccine*, 2011; 29(40):7020-7026.
Koster et al., "Milestones in progression of primary pneumonic plague in cynomolgus macaques," *Infect Immun*, 2010; 78(7):2946-2955.
Larkin et al., "Clustal W and Clustal X version 2.0," *Bioinformatics*, 2007; 23(21):2947-2948.
Lathem et al., "Progression of primary pneumonic plague: a mouse model of infection, pathology, and bacterial transcriptional activity," *Proc Natl Acad Sci U S A*, 2005; 102:17786-17791.
Lathem et al., "A plasminogen-activating protease specifically controls the development of primary pneumonic plague," *Science*, 2007; 315:509-513.
Lin et al., "IL-17 contributes to cell-mediated defense against pulmonary *Yersinia pestis*infection," *J Immunol.*, 2011; 186:1675-1684.
Matson et al., "Immunization of mice with YscF provides protection from Yersinia pestis infections," *BMC Microbiol*, 2005; 5:38.
Mett et al., "A plant-produced plague vaccine candidate confers protection to monkeys," *Vaccine*, 2007; 25(16):3014-3017.
Molinier-Frenkel et al., "Adenovirus hexon protein is a potent adjuvant for activation of a cellular immune response," *J Virol*, 2002, 76(1):127-135.
Motin et al., the difference in the IcrV sequences between Y. pestis and Y. pseudotuberculosis and its application for characterization of Y. pseudotuberculosis strains, *Microb Pathog*, 1992; 12(3):165-175.
Nanda et al., Immunogenicity of recombinant fiber-chimeric adenovirus serotype 35 vector-based vaccines in mice and rhesus monkeys, *J Virol*, 2005; 79(22):14161-14168.
Oyston et al., "An aroA mutant of Yersinia pestis is attenuated in guinea-pigs, but virulent in mice," *Microbiology*, 1996, 142(Pt 7):1847-1853.
Oyston et al., "The response regulator PhoP is important for survival under conditions of macrophage-induced stress and virulence in Yersinia pestis," *Infect Immun*, 2000; 68(6):3419-3425.
Patel et al., "Mucosal delivery of adenovirus-based vaccine protects against Ebola virus infection in mice," *J Infect Dis*, 2007; 196(Suppl 2): S413-20.
Perry et al., "*Yersinia pestis*—etiologic agent of plague," *Clin Microbiol Rev.*, 1997; 10:35-66.
Quenee et al., "Plague in Guinea pigs and its prevention by subunit vaccines," *Am J Pathol.*, 2011; 178:1689-1700.
Ransom et al., "Chronic pheumonic plague in Macaca mulatta," *Am J Trop Med Hyg*, 1954, 3(6):1040-1054.
Rosenzweig et al., "Progress on plague vaccine development," *Appl Microbiol Biotechnol.*, 2011; 91:265-286.
Russell et al., "A comparison of Plague vaccine, USP and EV76 vaccine induced protection against *Yersinia pestisin* a murine model," *Vaccine*, 1995; 13:1551-1556.
Russell, "Adenoviruses: update on structure and function," *J Gen Virol*, 2009; 90(Pt 1):1-20.
Sambrook et al. (Eds.), *Molecular Cloning: A Laboratory Manual*, Cold Spring Harbor Laboratory Press: Cold Spring Harbor, NY; 1989. Title page, publisher's page, and table of contents; 30 pgs.

(56) References Cited

OTHER PUBLICATIONS

Sha et al., "Braun lipoprotein (Lpp) contributes to virulence of yersiniae: potential role of Lpp in inducing bubonic and pneumonic plague," *Infect Immun.*, 2008; 76:1390-1409.
Sha et al., "Characterization of an F1 deletion mutant of *Yersinia pestis*CO92, pathogenic role of F1 antigen in bubonic and pneumonic plague, and evaluation of sensitivity and specificity of F1 antigen capture-based dipsticks," *J Clin Microbiol.*, 2011; 49:1708-1715.
Sha et al., "Deletion of the Braun lipoprotein-encoding gene and altering the function of lipopolysaccharide attenuate the plague bacterium," *Infect Immun.*, 2013; 81:815-828.
Sha et al., "A non-invasive in vivo imaging system to study dissemination of bioluminescent *Yersinia pestis*CO92 in a mouse model of pneumonic plague," *Microb Pathog.*, 2013; 55:39-50.
Sha et al., "a replication-defective human type 5 adenovirus-based trivalent vaccine confers complete protection against plague in mice and nonhuman primates," *Clinical and Vaccine Immunology*, 2016; 23(7):586-600.
Sievers et al., "Fast scalable generation of high-quality protein multiple sequence alignments using Clustal Omega," *Mol Syst Biol*, 2011; 7:539.
Smiley, "Current challenges in the development of vaccines for pneumonic plague," *Expert Rev Vaccines*, 2008; 7:209-221.
Smiley, "Immune defense against pneumonic plague," *Immunol Rev.*, 2008; 225:256-271.
Song et al., "Cytotoxic T lymphocyte responses to proteins encoded by heterologous transgenes transferred in vivo by adenoviral vectors," *Hum Gene Ther*, 1997; 8(10)1207-1217.
Stacy et al., "An age-old paradigm challenged: old baboons generate vigorous humoral immune responses to LcrV, a plague antigen," *J Immunol, 2008*; 181(1):109-115.
Suarez et al., "Role of Hcp, a type 6 secretion system effector, of *Aeromonas hydrophilain* modulating activation of host immune cells," *Microbiology*, 2010; 156:3678-3688.
Sun et al "Developing live vaccines against plague," *J Infect Dev Ctries*, 2011; 5:614-627.
Swietnicki et al., "*Yersinia pestis*Yop secretion protein F: purification, characterization, and protective efficacy against bubonic plague," *Protein Expr Purif*, 2005; 42(1):166-172.
Tatsis et al., "Adenoviruses as vaccine vectors," *Mol Ther*, 2004; 10(4):616-629.
Tatusova et al., "BLAST 2 Sequences, a new tool for comparing protein and nucleotide sequences," *FEMS Microbiol Lett.*, May 1999; 174(2):247-250.
Tiner et al., "Combinational Deletion of Three Membrane Protein-Encoding Genes Highly Attenuates *Yersinia pestis*while Retaining Immunogenicity in a Mouse Model of Pneumonic Plague," *Infect Immun.*, 2015; 83:1318-1338.
Tiner et al., "Intramuscular immunization of mice with a live-attenuated triple mutant of *Yersina pestis*CO92 induces robust humoral and cell-mediated immunity to completely protect animals against pneumonic plague," *Clin Vaccine Immunol*, Dec. 2015; 22(12):1255-1268.
Titball et al., "Vaccination against bubonic and pneumonic plague," *Vaccine*, 2001; 19(30):4175-4184.
Titball et al., "*Yersinia pestis*(plague) vaccines," *Expert Opin Biol Ther*, 2004; 4(6):965-973.
Tripathy et al., "Immune responses to transgene-encoded proteins limit the stability of gene expression after injection of replication-defective adenovirus vectors," *Nat Med*, 1996; 2(5):545-550.
Van Andel et al., "Clinical and pathologic features of cynomolgus macaques (Macaca fascicularis) infected with aerosolized *Yersinia pestis," Comp Med*, 2008; 58(1):68-75.
van Lier et al., "Deletion of Braun lipoprotein and plasminogen-activating protease-encoding genes attenuates *Yersinia pestisin* mouse models of bubonic and pneumonic plague," *Infect Immun.*, 2014; 82:2485-2503.
van Lier et al., "Further characterization of a highly attenuated *Yersinia pestis*CO92 mutant deleted for the genes encoding braun lipoprotein and plasminogen activator protease in murine alveolar and primary human macrophages," *Microb Pathog*, 2015, 80:27-38.
Warren et al., "Cynomolgus macaque model for pneumonic plague," *Microb Pathog*, 2011; 50(1):12-22.
Williams et al., "Investigation into the role of the serine protease HtrA in *Yersinia pestis*pathogenesis," 2000; 186(2):281-286.
Williamson et al., "Immunogenicity of the rF1+rV vaccine for plague with identification of potential immune correlates," *Microb Pathog*, 2007; 42(1):11-21.
Williamson et al., "Recombinant (F1+V) vaccine protects *cynomolgus macaques*against pneumonic plague," *Vaccine*, 2011; 29:4771-4777.
Wilson, "Adenoviruses as gene-delivery vehicles," *N. Engl J Med*, 1996; 334(18):1185-1187.
Xu et al., "An adenoviral vector-based mucosal vaccine is effective in protection against botulism," *Gene Ther*, 2009; 16(3):367-375.
Yu et al., Single intranasal immunization with recombinant adenovirus-based vaccine induces protective immunity against respiratory syncytial virus infection, *J Virol*, 2008; 82(5):2350-2357.
Zhang et al., "An adenovirus-vectored nasal vaccine confers rapid and sustained protection against anthrax in a single-dose regimen," *Clin Vaccine Immunol*, 2013; 20(1):1-8.

* cited by examiner

FIG. 15-01

An example of a nucleotide sequence (SEQ ID NO:1) encoding the YscF protein domain SEQ ID NO:2:

ATGGCTAATTTCTCCGGGTTCACAAAGGGCACTGACATTGCCGATCTTGATGCCGTTGCCCAGA
CTCTCAAGAAGCCTGCGGACGATGCCAACAAGGCAGTAAATGATTCCATCGCAGCCCTGAAAGA
CAAGCCTGACAATCCAGCACTCTTGGCCGACCTGCAACATAGTATCAACAAATGGTCTGTAATT
TACAATATAAACTCTACCATTGTGCGGTCCATGAAAGATCTGATGCAGGGGATCCTGCAAAAAT
TTCCC

An example of a YscF protein domain (SEQ ID NO:2):

MANFSGFTKGTDIADLDAVAQTLKKPADDANKAVNDSIAALKDKPDNPALLADLQHSINKWSVI
YNINSTIVRSMKDLMQGILQKFP

An example of a nucleotide sequence (SEQ ID NO:3) encoding the mature F1 protein domain SEQ ID NO:4:

GCCGACCTTACAGCTAGTACCACTGCCACAGCAACGCTTGTAGAGCCTGCCCGAATCACCCTGA
CGTATAAGGAGGGGGCTCCAATCACAATAATGGACAATGGAAACATCGATACCGAACTGCTGGT
GGGGACCCTGACACTGGGTGGCTACAAGACCGGCACAACCTCCACATCCGTGAACTTCACCGAC
GCCGCCGGCGATCCCATGTATCTCACATTCACTTCACAGGACGGCAACAATCATCAGTTCACCA
CTAAGGTGATTGGCAAGGATTCCAGAGACTTCGACATCTCTCCCAAGGTGAATGGCGAGAACCT
CGTGGGGGACGACGTGGTACTGGCAACAGGTTCCCAGGATTTCTTTGTCCGGTCCATTGGAAGC
AAAGGGGGCAAGCTGGCAGCAGGAAAATACACCGACGCAGTTACAGTGACTGTGTCAAACCAG

An example of a mature F1 protein domain (SEQ ID NO:4):

ADLTASTTATATLVEPARITLTYKEGAPITIMDNGNIDTELLVGTLTLGGYKTGTTSTSVNFTD
AAGDPMYLTFTSQDGNNHQFTTKVIGKDSRDFDISPKVNGENLVGDDVVLATGSQDFFVRSIGS
KGGKLAAGKYTDAVTVTVSNQ

FIG. 15-02

An example of a nucleotide sequence (SEQ ID NO:5) encoding a LcrV protein domain SEQ ID NO:6:

ATGATCCGCGCCTACGAGCAAAATCCTCAGCACTTCATTGAAGACCTTGAGAAGGTGCGCGTGG
AGCAGCTCACAGGCCACGGTAGCAGTGTCCTGGAGGAGCTTGTGCAGCTGGTGAAGGACAAGAA
TATCGATATTAGTATAAAATACGATCCAAGGAAAGACTCTGAGGTGTTCGCGAACCGCGTTATT
ACCGACGATATTGAACTCCTGAAGAAAATCCTGGCCTATTTTTTGCCAGAGGACGCTATCCTGA
AAGGGGGGCACTATGATAATCAGCTCCAAAATGGTATCAAACGGGTGAAAGAGTTCCTGGAGTC
TAGCCCAAATACTCAGTGGGAGCTGCGGGCCTTTATGGCTGTGATGCACTTTAGTCTGACAGCC
GATCGGATTGACGATGATATCCTTAAGGTGATCGTCGATAGCATGAACCATCATGGTGACGCAA
GAAGTAAACTGAGGGAGGAACTGGCCGAGCTGACTGCAGAGCTCAAAATCTATAGCGTCATACA
GGCCGAAATCAATAAGCACTTGAGCTCATCAGGCACCATTAACATCCACGACAAGTCCATTAAT
CTGATGGACAAAAATCTGTACGGATATACCGACGAGGAGATTTTCAAAGCGTCCGCCGAGTATA
AAATCCTCGAGAAAATGCCTCAGACAACTATACAGGTGGATGGTTCTGAAAAAAAGATTGTTTC
TATAAAGGACTTCCTCGGGTCCGAGAACAAAAGGACCGGCGCACTGGGCAATCTCAAGAACTCA
TACAGTTATAATAAAGATAATAATGAGCTTTCCCATTTTGCCACAACCTGCTCCGACAAAAGTA
GACCTCTGAACGACCTCGTGTCCCAAAAGACAACACAGCTGAGTGATATAACCTCCAGGTTCAA
CTCAGCGATCGAGGCTTTGAACAGGTTCATCCAGAAGTACGATTCAGTGATGCAGAGGCTGTTG
GATGATACTAGCGGTAAG

An example of a LcrV protein domain (SEQ ID NO:6):

MIRAYEQNPQHFIEDLEKVRVEQLTGHGSSVLEELVQLVKDKNIDISIKYDPRKDSEVFANRVI
TDDIELLKKILAYFLPEDAILKGGHYDNQLQNGIKRVKEFLESSPNTQWELRAFMAVMHFSLTA
DRIDDDILKVIVDSMNHHGDARSKLREELAELTAELKIYSVIQAEINKHLSSSGTINIHDKSIN
LMDKNLYGYTDEEIFKASAEYKILEKMPQTTIQVDGSEKKIVSIKDFLGSENKRTGALGNLKNS
YSYNKDNNELSHFATTCSDKSRPLNDLVSQKTTQLSDITSRFNSAIEALNRFIQKYDSVMQRLL
DDTSGK

FIG. 15-03

An example of a nucleotide sequence (SEQ ID NO:7) encoding a fusion protein SEQ ID NO:8:

ATGGCTAATTTCTCCGGGTTCACAAAGGGCACTGACATTGCCGATCTTGATGCCGTTGCCCAGA
CTCTCAAGAAGCCTGCGGACGATGCCAACAAGGCAGTAAATGATTCCATCGCAGCCCTGAAAGA
CAAGCCTGACAATCCAGCACTCTTGGCCGACCTGCAACATAGTATCAACAAATGGTCTGTAATT
TACAATATAAACTCTACCATTGTGCGGTCCATGAAAGATCTGATGCAGGGGATCCTGCAAAAAT
TTCCCGCCGACCTTACAGCTAGTACCACTGCCACAGCAACGCTTGTAGAGCCTGCCCGAATCAC
CCTGACGTATAAGGAGGGGGCTCCAATCACAATAATGGACAATGGAAACATCGATACCGAACTG
CTGGTGGGGACCCTGACACTGGGTGGCTACAAGACCGGCACAACCTCCACATCCGTGAACTTCA
CCGACGCCGCCGGCGATCCCATGTATCTCACATTCACTTCACAGGACGGCAACAATCATCAGTT
CACCACTAAGGTGATTGGCAAGGATTCCAGAGACTTCGACATCTCTCCCAAGGTGAATGGCGAG
AACCTCGTGGGGGACGACGTGGTACTGGCAACAGGTTCCCAGGATTTCTTTGTCCGGTCCATTG
GAAGCAAAGGGGGCAAGCTGGCAGCAGGAAAATACACCGACGCAGTTACAGTGACTGTGTCAAA
CCAGATGATCCGCGCCTACGAGCAAAATCCTCAGCACTTCATTGAAGACCTTGAGAAGGTGCGC
GTGGAGCAGCTCACAGGCCACGGTAGCAGTGTCCTGGAGGAGCTTGTGCAGCTGGTGAAGGACA
AGAATATCGATATTAGTATAAAATACGATCCAAGGAAAGACTCTGAGGTGTTCGCGAACCGCGT
TATTACCGACGATATTGAACTCCTGAAGAAAATCCTGGCCTATTTTTTGCCAGAGGACGCTATC
CTGAAAGGGGGGCACTATGATAATCAGCTCCAAAATGGTATCAAACGGGTGAAAGAGTTCCTGG
AGTCTAGCCCAAATACTCAGTGGGAGCTGCGGGCCTTTATGGCTGTGATGCACTTTAGTCTGAC
AGCCGATCGGATTGACGATGATATCCTTAAGGTGATCGTCGATAGCATGAACCATCATGGTGAC
GCAAGAAGTAAACTGAGGGAGGAACTGGCCGAGCTGACTGCAGAGCTCAAAATCTATAGCGTCA
TACAGGCCGAAATCAATAAGCACTTGAGCTCATCAGGCACCATTAACATCCACGACAAGTCCAT
TAATCTGATGGACAAAAATCTGTACGGATATACCGACGAGGAGATTTTCAAAGCGTCCGCCGAG
TATAAAATCCTCGAGAAAATGCCTCAGACAACTATACAGGTGGATGGTTCTGAAAAAAAGATTG
TTTCTATAAAGGACTTCCTCGGGTCCGAGAACAAAAGGACCGGCGCACTGGGCAATCTCAAGAA
CTCATACAGTTATAATAAAGATAATAATGAGCTTTCCCATTTTGCCACAACCTGCTCCGACAAA
AGTAGACCTCTGAACGACCTCGTGTCCCAAAAGACAACACAGCTGAGTGATATAACCTCCAGGT
TCAACTCAGCGATCGAGGCTTTGAACAGGTTCATCCAGAAGTACGATTCAGTGATGCAGAGGCT
GTTGGATGATACTAGCGGTAAG

An example of a fusion protein (SEQ ID NO:8):

MANFSGFTKGTDIADLDAVAQTLKKPADDANKAVNDSIAALKDKPDNPALLADLQHSINKWSVI
YNINSTIVRSMKDLMQGILQKFPADLTASTTATATLVEPARITLTYKEGAPITIMDNGNIDTEL
LVGTLTLGGYKTGTTSTSVNFTDAAGDPMYLTFTSQDGNNHQFTTKVIGKDSRDFDISPKVNGE
NLVGDDVVLATGSQDFFVRSIGSKGGKLAAGKYTDAVTVTVSNQMIRAYEQNPQHFIEDLEKVR
VEQLTGHGSSVLEELVQLVKDKNIDISIKYDPRKDSEVFANRVITDDIELLKKILAYFLPEDAI
LKGGHYDNQLQNGIKRVKEFLESSPNTQWELRAFMAVMHFSLTADRIDDDILKVIVDSMNHHGD
ARSKLREELAELTAELKIYSVIQAEINKHLSSSGTINIHDKSINLMDKNLYGYTDEEIFKASAE
YKILEKMPQTTIQVDGSEKKIVSIKDFLGSENKRTGALGNLKNSYSYNKDNNELSHFATTCSDK
SRPLNDLVSQKTTQLSDITSRFNSAIEALNRFIQKYDSVMQRLLDDTSGK

FIG. 15-04

An example of a nucleotide sequence (SEQ ID NO:9) encoding a fusion protein including linkers SEQ ID NO:10:

ATGGCTAATTTCTCCGGGTTCACAAAGGGCACTGACATTGCCGATCTTGATGCCGTTGCCCAGA
CTCTCAAGAAGCCTGCGGACGATGCCAACAAGGCAGTAAATGATTCCATCGCAGCCCTGAAAGA
CAAGCCTGACAATCCAGCACTCTTGGCCGACCTGCAACATAGTATCAACAAATGGTCTGTAATT
TACAATATAAACTCTACCATTGTGCGGTCCATGAAAGATCTGATGCAGGGGATCCTGCAAAAAT
TTCCCGGGGGCGGGGGTTCCGGGGGAGGCGGTAGTGGCGGCGGTGGATCAGCCGACCTTACAGC
TAGTACCACTGCCACAGCAACGCTTGTAGAGCCTGCCCGAATCACCCTGACGTATAAGGAGGGG
GCTCCAATCACAATAATGGACAATGGAAACATCGATACCGAACTGCTGGTGGGGACCCTGACAC
TGGGTGGCTACAAGACCGGCACAACCTCCACATCCGTGAACTTCACCGACGCCGCCGGCGATCC
CATGTATCTCACATTCACTTCACAGGACGGCAACAATCATCAGTTCACCACTAAGGTGATTGGC
AAGGATTCCAGAGACTTCGACATCTCTCCCAAGGTGAATGGCGAGAACCTCGTGGGGGACGACG
TGGTACTGGCAACAGGTTCCCAGGATTTCTTTGTCCGGTCCATTGGAAGCAAAGGGGGCAAGCT
GGCAGCAGGAAAATACACCGACGCAGTTACAGTGACTGTGTCAAACCAGGGAGGCGGTGGATCC
GGAGGCGGAGGCTCAGGAGGCGGGGGGAGCATGATCCGCGCCTACGAGCAAAATCCTCAGCACT
TCATTGAAGACCTTGAGAAGGTGCGCGTGGAGCAGCTCACAGGCCACGGTAGCAGTGTCCTGGA
GGAGCTTGTGCAGCTGGTGAAGGACAAGAATATCGATATTAGTATAAAATACGATCCAAGGAAA
GACTCTGAGGTGTTCGCGAACCGCGTTATTACCGACGATATTGAACTCCTGAAGAAAATCCTGG
CCTATTTTTTGCCAGAGGACGCTATCCTGAAAGGGGGGCACTATGATAATCAGCTCCAAAATGG
TATCAAACGGGTGAAAGAGTTCCTGGAGTCTAGCCCAAATACTCAGTGGGAGCTGCGGGCCTTT
ATGGCTGTGATGCACTTTAGTCTGACAGCCGATCGGATTGACGATGATATCCTTAAGGTGATCG
TCGATAGCATGAACCATCATGGTGACGCAAGAAGTAAACTGAGGGAGGAACTGGCCGAGCTGAC
TGCAGAGCTCAAAATCTATAGCGTCATACAGGCCGAAATCAATAAGCACTTGAGCTCATCAGGC
ACCATTAACATCCACGACAAGTCCATTAATCTGATGGACAAAAATCTGTACGGATATACCGACG
AGGAGATTTTCAAAGCGTCCGCCGAGTATAAAATCCTCGAGAAAATGCCTCAGACAACTATACA
GGTGGATGGTTCTGAAAAAAAGATTGTTTCTATAAAGGACTTCCTCGGGTCCGAGAACAAAAGG
ACCGGCGCACTGGGCAATCTCAAGAACTCATACAGTTATAATAAAGATAATAATGAGCTTTCCC
ATTTTGCCACAACCTGCTCCGACAAAAGTAGACCTCTGAACGACCTCGTGTCCCAAAAGACAAC
ACAGCTGAGTGATATAACCTCCAGGTTCAACTCAGCGATCGAGGCTTTGAACAGGTTCATCCAG
AAGTACGATTCAGTGATGCAGAGGCTGTTGGATGATACTAGCGGTAAG

An example of a fusion protein including linkers (SEQ ID NO:10):

MANFSGFTKGTDIADLDAVAQTLKKPADDANKAVNDSIAALKDKPDNPALLADLQHSINKWSVI
YNINSTIVRSMKDLMQGILQKFPGGGGSGGGGSGGGGSADLTASTTATATLVEPARITLTYKEG
APITIMDNGNIDTELLVGTLTLGGYKTGTTSTSVNFTDAAGDPMYLTFTSQDGNNHQFTTKVIG
KDSRDFDISPKVNGENLVGDDVVLATGSQDFFVRSIGSKGGKLAAGKYTDAVTVTVSNQGGGGS
GGGGSGGGGSMIRAYEQNPQHFIEDLEKVRVEQLTGHGSSVLEELVQLVKDKNIDISIKYDPRK
DSEVFANRVITDDIELLKKILAYFLPEDAILKGGHYDNQLQNGIKRVKEFLESSPNTQWELRAF
MAVMHFSLTADRIDDDILKVIVDSMNHHGDARSKLREELAELTAELKIYSVIQAEINKHLSSSG
TINIHDKSINLMDKNLYGYTDEEIFKASAEYKILEKMPQTTIQVDGSEKKIVSIKDFLGSENKR
TGALGNLKNSYSYNKDNNELSHFATTCSDKSRPLNDLVSQKTTQLSDITSRFNSAIEALNRFIQ
KYDSVMQRLLDDTSGK

METHODS FOR TREATING PLAGUE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application *is a reissue of U.S. Pat. No. 10,076,562, which* claims the benefit of U.S. Provisional Application Ser. No. 62/324,528, filed Apr. 19, 2016, which [is] *are* incorporated by reference herein.

GOVERNMENT FUNDING

This invention was made with government support under grant number AI071634, awarded by the NIH. The government has certain rights in the invention.

SEQUENCE LISTING

This application contains a Sequence Listing electronically submitted via EFS-Web to the United States Patent and Trademark Office as an ASCII text file entitled "265-00920101-SequenceListing_ST25.txt" having a size of 24 kilobytes and created on Jun. 22, 2017. The information contained in the Sequence Listing is incorporated by reference herein.

SUMMARY OF THE APPLICATION

Provided herein are methods that include administering a first composition to a subject. The administration is to a mucosal surface, and in one embodiment the administration is by an intranasal route. The first composition includes a vector that has a polynucleotide encoding a fusion protein, where the fusion protein includes a YscF protein domain, a mature F1 protein domain, and a LcrV protein domain. The method also includes administering a second composition to the subject by a different route, such as an intramuscular route. The second composition includes a fusion protein having the same three domains, and in one embodiment the fusion protein is the same one administered by an intranasal route. In one embodiment, the fusion protein is isolated. The second composition is administrated after the intranasal administration.

In one embodiment, the fusion protein includes at least one linker, where the linker is present between two of the domains. In one embodiment, the fusion protein includes a His-tag. In one embodiment, the vector is a replication defective adenovirus vector, such as a type-5 (Ad5). In one embodiment, the fusion protein includes the YscF protein, the mature F1 protein, and the LcrV protein. In one embodiment, the second administration is at least 7 days after the intranasal administration. In one embodiment, the subject is a human. In one embodiment, the administering confers immunity to plague, such as pneumonic plague, caused by Yersinia pestis.

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, tetramers). Thus, the terms peptide, oligopeptide, and polypeptide are all included within the definition of protein and these terms are used interchangeably.

As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. In one embodiment, a polynucleotide is isolated. A polynucleotide can be linear or circular in topology. A polynucleotide can be, for example, a portion of a vector, such as an expression or cloning vector, or a fragment.

As used herein, an "isolated" substance is one that has been removed from a cell and many of the proteins, nucleic acids, and other cellular material of its natural environment are no longer present. A substance may be purified, i.e., at least 60% free, at least 75% free, or at least 90% free from other components with which they are naturally associated. Proteins and polynucleotides that are produced by recombinant, enzymatic, or chemical techniques are considered to be isolated and purified by definition, since they were never present in a cell. For instance, a protein, a polynucleotide, or a viral particle can be isolated or purified.

As used herein, the terms "coding region," "coding sequence," and "open reading frame" are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end.

A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 15-01-15-04 shows protein sequences and examples of nucleotide sequences encoding the proteins.

DETAILED DESCRIPTION OF ILLUSTRATIVE EMBODIMENTS

Figure 1:
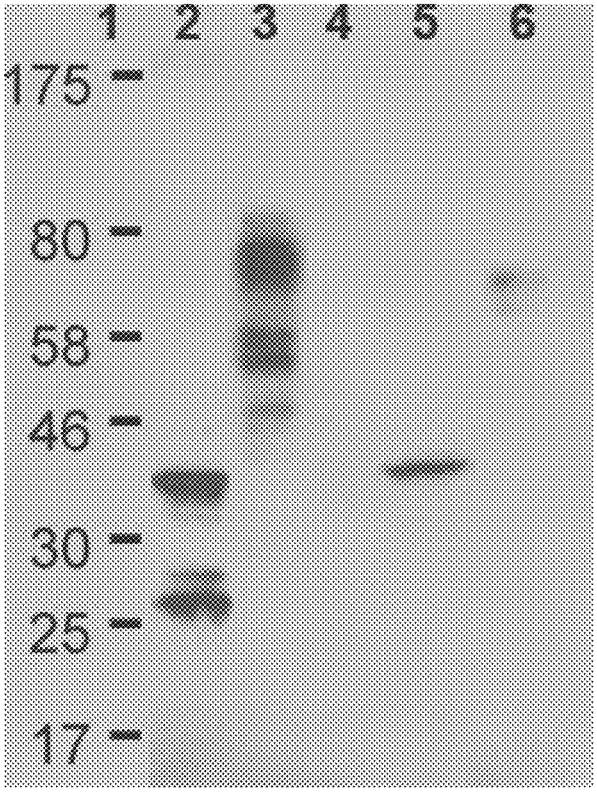
FIG. 1 shows immunoblot analysis of recombinant adenoviruses. Human lung epithelial cells A549 were infected with rAd5 constructs at 1000 v.p. per cell. Host cell lysates were harvested after 24 h p.i. An aliquot of the cell lysates was then resolved by SDSPAGE and subjected to Western blot analysis by using mAb-LcrV antibody. Lane 1: Standard protein molecular weight markers in kilo-daltons (kDa). Lanes 2-4: A549 cells infected with rAd5-LcrV, rAd5-YFV and Ad5-empty, respectively. Lane 5: Purified rLcrV (50 ng). Lane 6: Purified rYFV (30 ng). The HRP-labeled anti-mouse secondary antibody and ECL Western blotting reagent kit (Millipore, Billerica, Mass.) was used for protein detection.

Provided herein are methods for using a fusion protein. The fusion protein includes at least three protein domains. The three domains are a YscF protein domain, a mature F1 protein domain, and a LcrV protein domain. A fusion protein can be isolated, and optionally purified.

An example of a YscF protein domain is depicted at SEQ ID NO:2. Other examples of YscF protein domains include those having sequence similarity with the amino acid sequence of SEQ ID NO:2.

An example of a mature F1 protein domain is depicted at SEQ ID NO:4. Other examples of mature F1 protein domains include those having sequence similarity with the amino acid sequence of SEQ ID NO:4.

An example of a LcrV protein domain is depicted at SEQ ID NO:6. Other examples of LcrV protein domains include those having sequence similarity with the amino acid sequence of SEQ ID NO:6.

An example of a fusion protein is depicted at SEQ ID NO:8. The fusion protein depicted at SEQ ID NO:8 includes, from amino-terminal to carboxy-terminal end, a YscF domain, a mature F1 domain, followed by a LcrV domain; however, a fusion protein can include the three domains in any order. Thus, other fusion proteins have the domains in the order of, from amino-terminal to carboxy-terminal end, a LcrV domain, a YscF domain, followed by a mature F1 domain; a LcrV domain, a mature F1 domain, followed by a YscF domain; a YscF domain, a LcrV domain, followed by a mature F1 domain; a mature F1 domain, a YscF domain, followed by a LcrV domain; and a mature F1 domain, a LcrV domain, followed by a YscF domain. Other examples of a fusion protein include those having sequence similarity with the amino acid sequence of SEQ ID NO:8, and those having sequence similarity with any other fusion protein described herein.

A fusion protein described herein has immunological activity. "Immunological activity" refers to the ability of a protein to elicit an immunological response in a subject. An immunological response to a protein is the development in a subject of a cellular and/or antibody-mediated immune response to the protein. Usually, an immunological response includes but is not limited to one or more of the following effects: the production of antibodies, B cells, helper T cells, suppressor T cells, and/or cytotoxic T cells, directed to an epitope or epitopes of the protein. "Epitope" refers to the site on an antigen to which specific B cells and/or T cells respond so that antibody is produced. The immunological activity may be protective. "Protective immunological activity" refers to the ability of a protein to elicit an immunological response in a subject that prevents or inhibits infection by a Yersinia spp., such as Yersinia pestis. Whether a protein has protective immunological activity can be determined by methods known in the art such as, for example, the methods described in Example 1. For example, a protein described herein, or combination of proteins described herein, protects a subject against challenge with a Yersinia pestis.

Sequence similarity of two proteins can be determined by aligning the residues of the two proteins (for example, a candidate protein domain and a reference protein, e.g., a YscF protein domain such as SEQ ID NO:2, a mature F1 protein domain such as SEQ ID NO:4, a LcrV protein domain such as SEQ ID NO:6, or a fusion protein such as SEQ ID NO:8) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein. A candidate protein is the protein being compared to the reference protein. A candidate protein may be isolated, for example, from a microbe such as a Yersinia pestis, or can be produced using recombinant techniques, or chemically or enzymatically synthesized. When the candidate protein domain is present as part of a fusion protein, only those amino acids of the protein domain are compared with a reference protein. For instance, if the candidate protein is YscF and is part of a fusion protein, only those residues of the YscF domain of the fusion protein are aligned with a reference protein.

Unless modified as otherwise described herein, a pairwise comparison analysis of amino acid sequences can be carried out using the Blastp program of the BLAST 2 search algorithm, as described by Tatiana et al., (FEMS Microbiol Lett, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on. Alternatively, proteins may be compared using the BESTFIT algorithm in the GCG package (version 10.2, Madison Wis.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein described herein may be selected from other members of the class to which the amino acid belongs. For example, it is known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a protein sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Guidance on how to modify the amino acid sequences of the protein domains disclosed herein can also be obtained by producing a protein alignment of a reference protein (e.g., SEQ ID NO:2, SEQ ID NO:4, or SEQ ID NO:6) with other related polypeptides. For instance, the reference protein SEQ ID NO:2 can be aligned in a multiple protein alignment with other YscF proteins. Such an alignment shows the locations of residues that are identical between each of the proteins, the locations of residues that are conserved between each of the proteins, and the locations of residues that are not conserved between each of the proteins. By reference to such an alignment, the skilled person can predict which alterations to an amino acid sequence are likely to modify activity, as well as which alterations are unlikely to modify activity. Methods for producing multiple protein alignments are routine, and algorithms such as ClustalW (Larkin et al., 2007, ClustalW and ClustalX version 2, Bioinformatics 23(21): 2947-2948) and Clustl Omega (Sievers et al., 2011, Molecular Systems Biology 7: 539, doi:10.1038/msb.2011.75; Goujon et al., 2010, Nucleic acids research 38 (Suppl 2):W695-9, doi:10.1093/nar/gkq313).

Thus, as used herein, a candidate protein domain useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% amino acid sequence similarity, or complete identity to a reference amino acid sequence.

Alternatively, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% amino acid sequence similarity, or complete identity to the reference amino acid sequence.

In one embodiment, a fusion protein described herein includes a linker between one or more the protein domains. A linker is an amino acid sequence that joins protein domains in a fusion protein. A linker can be flexible or rigid, and in one embodiment is flexible. In one embodiment, a linker can be at least 3, at least 4, at least 5, or at least 6 amino acids in length. It is expected that there is no upper limit on the length of a linker used in a fusion protein described herein; however, in one embodiment, a linker is no greater than 10, no greater than 9, no greater than 8, or no greater than 7 amino acids in length. Many linkers are known to a skilled person (see Chen et al. 2013, Adv, Drug Deliv. Rev., 65(10):1357-1369). Specific examples of linkers include GGGGS (SEQ ID NO:11). In one embodiment, a fusion protein can include more than one type of linker, e.g., one type of linker between a YscF protein domain and a mature F1 protein domain, and another type of linker between a mature F1 protein and a LcrV protein. In one embodiment, a fusion protein can include more than one linker between two protein domains, e.g., two GGGGS (SEQ ID NO:11) linkers or three GGGGS (SEQ ID NO:11) linkers between a YscF protein domain and a mature F1 protein domain. An example of a fusion protein having three GGGGS (SEQ ID NO:11) linkers between the domains is depicted at SEQ ID NO:10 (the amino acids corresponding to the linkers are underlined). This fusion protein includes, from amino-terminal to carboxy-terminal end, a YscF domain, a mature F1 domain, followed by a LcrV domain, with three GGGGS (SEQ ID NO:11) linkers between the YscF domain and the mature F1 domain, and three GGGGS (SEQ ID NO:11) linkers between the mature F1 domain and the LcrV domain.

A fusion protein as described herein also can be designed to include one or more additional sequences such as, for example, the addition of C-terminal and/or N-terminal amino acids. In one embodiment, additional amino acids may facilitate purification by trapping on columns or use of antibodies. Such additional amino acids include, for example, histidine-rich tags that allow purification of proteins on nickel columns.

Also provided are polynucleotides encoding a fusion protein described herein that includes at least three protein domains. Given the amino acid sequence of a fusion protein described herein that includes at least three protein domains, a person of ordinary skill in the art can determine the full scope of polynucleotides that encode that amino acid sequence using conventional, routine methods. The class of nucleotide sequences encoding a selected protein sequence is large but finite, and the nucleotide sequence of each member of the class may be readily determined by one skilled in the art by reference to the standard genetic code, wherein different nucleotide triplets (codons) are known to encode the same amino acid. An example of a polynucleotide encoding a YscF protein domain is depicted at SEQ ID NO:1. An example of a polynucleotide encoding a mature F1 protein domain is depicted at SEQ ID NO:3. An example of a polynucleotide encoding a LcrV protein domain is depicted at SEQ ID NO:5. An example of a polynucleotide encoding a fusion protein is depicted at SEQ ID NO: 7.

A fusion protein described herein that includes at least three protein domains may include additional nucleotides flanking the coding region encoding the fusion protein. The boundaries of a coding region are generally determined by a translation start codon at its 5' end and a translation stop codon at its 3' end. In one embodiment, the additional nucleotides include vector nucleotides. In another embodiment, the additional nucleotides aid in expression of the fusion protein, such as expression for subsequent isolation and optional purification.

A polynucleotide that encodes a fusion protein described herein can be present in a vector. A vector is a replicating polynucleotide, such as a plasmid, phage, or cosmid, to which another polynucleotide may be attached so as to bring about the replication of the attached polynucleotide. Construction of vectors containing a polynucleotide described herein employs standard ligation techniques known in the art. See, e.g., Sambrook et al, Molecular Cloning: A Laboratory Manual., Cold Spring Harbor Laboratory Press (1989). A vector can provide for further cloning (amplification of the polynucleotide), e.g., a cloning vector, or for expression of the polynucleotide, e.g., an expression vector. The term vector includes, but is not limited to, plasmid vectors, viral vectors, cosmid vectors, and transposon vectors. A vector may be replication-proficient or replication-deficient. A vector may result in integration into a cell's genomic DNA.

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as yeast cells, murine cells, and human cells. Suitable prokaryotic cells include eubacteria, such as gram-negative organisms, for example, E. coli. Suitable eukaryotic cells include, but are not limited to, human embryonic kidney 293 (HEK293) cells.

An expression vector optionally includes regulatory sequences operably linked to a polynucleotide encoding the fusion protein. An example of a regulatory sequence is a promoter. A promoter may be functional in a host cell used, for instance, in the construction and/or characterization of a polynucleotide encoding a fusion protein described herein, and/or may be functional in the ultimate recipient of the vector. A promoter may be inducible, repressible, or constitutive, and examples of each type are known in the art. A polynucleotide encoding a protein described herein may also include a transcription terminator. Suitable transcription terminators are known in the art.

A vector introduced into a host cell optionally includes one or more marker sequences, which typically encode a molecule that inactivates or otherwise detects or is detected by a compound in the growth medium. Certain selectable markers may be used to confirm that the vector is present within the target cell. For example, the inclusion of a marker sequence may render the transformed cell resistant to an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, neomycin, puromycin, hygromycin, DHFR, GPT, zeocin, histidinol, and others.

In one embodiment, the vector is an adenoviral vector. Adenoviruses are non-enveloped viruses 70-90 nm in diameter with an icosahedral capsid. Their genome is linear, double stranded DNA varying between 25-45 kilobases in size with inverted terminal repeats (ITRs) at both termini and a terminal protein attached to the 5' ends (Russell, 2000, J Gen Virol., 90:1-20). Their genome also encompasses an encapsidation sequence (Psi), early genes, and late genes. The principal early genes are contained in the regions E1, E2, E3 and E4. Of these, the genes contained in the E1 region are required for viral propagation. The principal late genes are contained in the regions L1 to L5.

Adenoviruses have been used as the basis for a variety of vectors which incorporate various coding regions. In each of these constructs, the adenovirus has been modified in such a way as to render it unable to replicate following gene transfer. Thus, available constructs are adenoviruses in which genes of the early region, adenoviral E1, E2A, E2B, E3, E4, or combinations thereof, are deleted and into the sites of which a DNA sequence encoding a desired protein can be inserted. One example of an adenoviral vector routinely used is adenovirus serotype 5 (Ad5). In the first Ad5 vectors, E1 and/or E3 regions were deleted enabling insertion of foreign DNA to the vectors (Danthinne and Imperiale, 2000, Gene Ther., 7:1707-14; see also Rankii et al., U.S. Pat. No. 9,410,129, and Crouset et al., U.S. Pat. No. 6,261,807). Furthermore, deletions of other regions as well as further mutations have provided extra properties to viral vectors. An example of an adenovirus encoding a fusion protein described herein is disclosed in Clarke (US Patent Publication 2010/0209451). A viral vector, such as a adenoviral vector, can be present as a polynucleotide or as a polynucleotide inside a viral particle.

In one embodiment, a composition includes at least one fusion protein described herein. In one embodiment, a composition includes a vector encoding a fusion protein described herein. In one embodiment, the vector is an adenovirus vector, and the vector can be present in a viral particle. Unless a specific level of sequence similarity and/or identity is expressly indicated herein (e.g., at least 80% sequence similarity, at least 90% sequence identity, etc.), reference to the amino acid sequence of an identified SEQ ID NO includes variants having the levels of sequence similarity and/or the levels of sequence identity described herein.

The compositions as described herein optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, orally, parenterally including intradermal, transcutaneous and subcutaneous, intramuscular, intravenous, intraperitoneal, etc., and topically, such as, intranasal, intrapulmonary, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the subject's body.

A composition described herein can be referred to as a vaccine. The term "vaccine" as used herein refers to a composition that, upon administration to a subject, will increase the likelihood the recipient is protected against a Yersinia spp., such as Y. pestis.

A composition as described herein may be administered in an amount sufficient to treat certain conditions as described herein. The amount of fusion protein or vector present in a composition as described herein can vary. In one embodiment, a dosage of viral particles containing a vector that encodes a fusion protein described herein can be at least $1\times10^{8}$, at least $5\times10^{8}$, at least $1\times10^{9}$, or at least $5\times10^{9}$ viral particles, and no greater than $1\times10^{10}$, no greater than $5\times10^{10}$, no greater than $1\times10^{11}$, or no greater than $5\times10^{11}$ viral particles. In one embodiment, a dosage of a fusion protein (e.g., intramuscular) described herein can be at least 0.01 micrograms (m), at least 0.1 μg, at least 1 μg, or at least 10 μg, and no greater than 20 μg, no greater than 50 μg, or no greater than 100 μg.

The formulations may be conveniently presented in unit dosage form and may be prepared by methods well known in the art of pharmacy. Methods of preparing a composition with a pharmaceutically acceptable carrier include the step of bringing the active compound (e.g., a viral particle or fusion protein as described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyl dioctadecyl ammonium bromide (DDA), avridine, aluminum hydroxide, magnesium hydroxide, oils, saponins, alpha-tocopherol, polysaccharides, emulsified paraffins, ISA-70, RIBI, and other substances known in the art. It is expected that proteins as described herein will have immunoregulatory activity and that such proteins may be used as adjuvants that directly act as T cell and/or B cell activators or act on specific cell types that enhance the synthesis of various cytokines or activate intracellular signaling pathways. Such proteins are expected to augment the immune response to increase the protective index of the existing composition.

In another embodiment, a composition as described herein including a pharmaceutically acceptable carrier can include a biological response modifier, such as, for example, IL-2, IL-4 and/or IL-6, TNF, IFN-α, IFN-γ, and other cytokines that effect immune cells. A composition can also include other components known in the art such as an antibiotic, a preservative, an anti-oxidant, or a chelating agent.

Also provided are methods of using the compositions described herein. The methods include administering to a subject an effective amount of a composition described herein. The subject can be, for instance, a human, a non-human primate (such as a cynomolgus macaque), a murine (such as a mouse or a rat), a guinea pig, or a rabbit.

In some aspects, the methods may further include additional administrations (e.g., one or more booster administrations) of the composition to the subject to enhance or stimulate a secondary immune response. A booster can be administered at a time after the first administration, for instance, one to eight weeks, such as two to four weeks, after the first administration of the composition. Subsequent boosters can be administered one, two, three, four, or more times annually. Without intending to be limited by theory, it is expected that in some aspects annual boosters will not be necessary, as a subject will be challenged in the field by exposure to microbes expressing proteins present in the compositions having epitopes that are identical to or structurally related to epitopes present on proteins of the composition administered to the subject.

In one embodiment, a method includes an administration of a vector that includes a coding region encoding a fusion protein described herein. The vector can be a viral vector, and the viral vector can be present in a viral particle. An example of a viral vector is an adenovirus. The administration of the vector can be topical, such as delivery to the nasal or respiratory mucosa. The administration of the vector can be followed by a booster administration of an isolated or purified fusion protein described herein. The booster can be parenteral, such as intramuscular, intradermal, or subcutaneous. Optionally, more than one administration of the vector can occur, and more than one administration of the fusion protein can occur.

In one aspect, the invention is directed to methods for producing an immune response in the recipient subject. An immune response can be humoral, cellular, or a combination thereof Antibody produced includes antibody that specifically binds the fusion protein. A cellular immune response includes immune cells that are activated by the fusion protein. In this aspect, an "effective amount" is an amount effective to result in the production of an immune response in the subject. Methods for determining whether a subject has produced antibodies that specifically bind a fusion protein, and determining the presence of a cellular immune response, are routine and know in the art.

In one aspect the invention is also directed to conferring immunity to plague in a subject, including a human, caused by Yersinia spp., such as Y. pestis. The plague can be pneumonic, bubonic, or septicemic. Conferring immunity is typically prophylactic—e.g., initiated before a subject is infected by a microbe causing plague, and is referred to herein as treatment of a subject that is "at risk" of infection. As used herein, the term "at risk" refers to a subject that may or may not actually possess the described risk. Thus, typically, a subject "at risk" of infection by a microbe causing plague is a subject present in an area where subjects have been identified as infected by the microbe and/or is likely to be exposed to the microbe even if the subject has not yet manifested any detectable indication of infection by the microbe and regardless of whether the subject may harbor a subclinical amount of the microbe. An example of a subject likely to be exposed to the microbe includes a subject in the armed forces deployed at a location where there is risk of exposure to Y. pestis, such as a weaponized Y. pestis. While the methods described herein are of use in prophylactic treatment, the methods can also be used to treat a subject after the subject is infected by the microbe. Accordingly, administration of a composition can be performed before, during, or after the subject has first contact with the microbe, and the subject can have or be at risk of having plague, such as pneumonic plague. Treatment initiated before the subject's first contact with the microbe can result in increased immunity to infection by the microbe.

In another aspect, the method is directed to treating one or more symptoms or clinical signs of certain conditions in a subject that can be caused by infection by a microbe causing plague including Yersinia spp., such as Y. pestis. As used herein, the term "symptom" refers to subjective evidence of a disease or condition experienced by the patient and caused by infection by a microbe. As used herein, the term "clinical sign" or, simply, "sign" refers to objective evidence of disease or condition caused by infection by a microbe. The method includes administering an effective amount of a composition described herein to a subject having a condition, or exhibiting symptoms and/or clinical signs of a condition, and determining whether at least one symptom and/or clinical sign of the condition is changed, preferably, reduced. Examples of symptoms and/or clinical signs caused by a microbe causing plague, such as Y. pestis, are known to the person skilled in the art. The successful treatment of infection by Y. pestis in a subject is disclosed in Example 1, which demonstrates the protection against plague disease caused by Y. pestis in a mouse model and cynomolgus macaques by administering a composition described herein. Mouse and cynomolgus macaques models are a commonly accepted model for the study of disease caused by Y. pestis.

Also provided herein is a kit for immunizing a subject to protect against plague. The kit includes a vector described herein, such as an adenoviral vector, which includes a coding region encoding a fusion protein described herein in a suitable packaging material in an amount sufficient for at least one administration. The kit also includes a fusion protein described herein, in a suitable packaging material in an amount sufficient for at least one administration. Optionally, other reagents such as buffers and solutions needed to administer the two compositions are also included. Instructions for use of the packaged materials are also typically included. As used herein, the phrase "packaging material" refers to one or more physical structures used to house the contents of the kit. The packaging material is constructed by well known methods, generally to provide a sterile, contaminant-free environment. The packaging material may have a label which indicates that the materials can be used for conferring immunity to a subject. In addition, the packaging material contains instructions indicating how the materials within the kit are employed to immunize a subject to protect against plague. As used herein, the term "package" refers to a container such as glass, plastic, paper, foil, and the like, capable of holding within fixed limits the materials and other optional reagents. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following example. It is to be understood that the particular examples, materials, amounts, and procedures are to be interpreted broadly in accordance with the scope and spirit of the invention as set forth herein.

Example 1

Currently, no plague vaccine exists in the United States for human use. The capsular antigen (Cafl or F1) and two type 3 secretion system (T3SS) components, the low calcium response V antigen (LcrV) and the needle protein YscF, represent protective antigens of Yersinia pestis. We used a replication-defective human type-5 adenovirus vector (Ad5) and constructed recombinant monovalent and trivalent vaccines (rAd5-LcrV and rAd5-YFV) that expressed either the codon-optimized lcrV or the fusion gene YFV (made up of ycsF, cafl and lcrV). Immunization of mice with the trivalent rAd5-YFV vaccine by either the intramuscular (i.m.) or the intranasal (i.n.) route provided superior protection compared to the monovalent rAd5-LcrV vaccine against bubonic and pneumonic plague when animals were challenged with Y. pestis CO92. Pre-existing adenoviral immunity did not diminish the protective response, and the protection was always higher when mice were administered one i.n. dose of the trivalent vaccine (priming) followed by a single i.m. booster dose of the purified YFV antigen. Immunization of cynomolgus macaques with the trivalent rAd5-YFV vaccine by the prime-boost strategy provided 100% protection to animals that had pre-existing adenoviral immunity, against a stringent aerosol challenge dose of CO92. The vaccinated and challenged macaques had no signs of disease, and the invading pathogen rapidly cleared with no histopathological lesions. This is the first report showing the efficacy of an adenovirus-vectored trivalent vaccine against pneumonic plague in mouse and NHP models.

INTRODUCTION

Yersinia pestis is the causative agent of plague, and can be transmitted to humans via an infected flea bite or by direct inhalation of the aerosolized bacilli from an infected person or an animal (1, 2). Plague manifests itself in three major forms in humans, namely bubonic, septicemic, and pneumonic (2). Pneumonic plague is the most feared form due to its rapid onset and associated high mortality rate (1, 2). Y. pestis has been responsible for at least three pandemics in the past, which killed more than 200 million people (3). Current epidemiological records suggest 4,000 human plague cases annually worldwide (2) The emergence of multi-antibiotic resistant Y. pestis strains from plague patients, and the potential of malicious dissemination of recombinantly engineered bacteria as an airborne bioweapon, necessitates the development of an effective pre-exposure and/or post-exposure prophylaxis treatment (1, 2).

Currently, no Food and Drug Administration (FDA)-licensed plague vaccine exists in the United States, and recent efforts have focused on the development of recombinant subunit plague vaccines consisting of two well-characterized Y. pestis antigens, the F1 capsular antigen, and the type 3 secretion system (T3SS) component and effector LcrV (4-8). F1 encoded by the caf1 gene has a polymeric structure and confers bacterial resistance to phagocytosis (9). The F1-V-based vaccines are generally protective against pneumonic plague in rodents and non-human primates (NHPs), and are currently undergoing clinic trails (10-17). However, considering the natural existence of fully virulent F1 minus Y. pestis strains (18, 19) or those that have highly diverged LcrV variants (20, 21), such F1-V-based vaccines would most likely not provide optimal protection across all plague-causing Y. pestis strains in humans.

In an effort to search for new immunogenic antigens for the plague subunit vaccines, recent studies have shown that vaccination of mice with recombinant T3SS needle structure protein YscF (rYscF) provided protection to mice against subcutaneous injection of the fully virulent and encapsulated Y. pestis strain CO92, and against an intravenously injected pigmentation locus-negative Y. pestis KIM strain (22, 23).

In this study, we used a replication-defective human type-5 adenovirus vector (Ad5) to construct recombinant monovalent and trivalent (rAd5-LcrV and rAd5-YFV) vaccines that expressed either the lcrV or the fusion gene YFV (ycsF, cafl, and lcrV). We demonstrated the trivalent rAd5-YFV vaccine provided superior protection to immunized mice than the monovalent rAd5-LcrV vaccine against both bubonic and pneumonic plague, irrespective of whether or not the pre-existing adenoviral immunity was artificially developed in these animals. Most importantly, one dose of the trivalent rAd5-YFV vaccine by the intranasal (i.n.) route in conjunction with a single dose of the purified recombinant fusion protein rYFV by the intramuscular (i.m.) route in a prime-boost strategy, provided impressive (up to 100%) protection to both mice and cynomolgus macaques against high challenge doses of WT CO92 when given by the aerosol route. Vaccinated NHPs rapidly cleared the pathogen with no signs of disease and histopathological lesions in various organs.

Materials and Methods

Bacterial strains and reagents. Y. pestis CO92 strain (WT CO92) was isolated in 1992 from a fatal human pneumonic plague case and acquired through the BEI Resources, Manassas, Va. The bioluminescent WT Y. pestis CO92 luc2 strain (WT CO92 luc2), which contains the luciferase operon (luc or lux), allowing in vivo imaging of mice for bacterial dissemination in real time, was previously constructed in our laboratory (26, 27). Y. pestis strains were grown in heart infusion broth (HIB) medium (Difco, Voigt Global Distribution Inc., Lawrence, Kans.) at 26 to 28° C. with constant agitation (180 rpm) or on either 1.5% HIB agar or 5% sheep blood agar (SBA) plates (Teknova, Hollister, Calif.). For the aerosol challenge, WT CO92 was grown in HIB enriched with 0.2% xylose (DL-xylose; Sigma-Aldrich, St. Louis, Mo.) as we previously described (28). Luria-Bertani (LB) medium was used for growing Escherichia coli at 37° C. with agitation. Restriction endonucleases and T4 DNA ligase were obtained from Promega (Madison, Wis.). Advantage cDNA PCR kits were purchased from Clontech (Palo Alto, Calif.). All digested plasmid DNA or DNA fragments from agarose gels were purified using QIAquick kits (Qiagen, Inc., Valencia, Calif.).

Production and purification of recombinant proteins. Genes encoding YscF, Caf1 (F1), and LcrV were amplified from the genome of WT CO92 by polymerase chain reaction (PCR) with the primer sets YscFHis_F.cln (CA CATATGAGTAACTTCTCTGGATTTACGAAAG, SEQ ID NO:12) and YscFHis_R.cln (CA CTCGAGTGGGAACTTCTGTAGGATGCCTT, SEQ ID NO:13), Caf1His_F.cln (CA CATATGAAAAAAATCAGTTCCGTTATCG, SEQ ID NO:14) and Caf1His_R.cln (CA CTCGAGTTGGTTAGATACGGTTACGGTTACAG, SEQ ID NO:15), LcrVHis_F.cln (CA CATATGATTAGAGCCTACGAACAAAACCC, SEQ ID NO:16) and LcrVHis_R.cln (CA GTCGACTTTACCAGACGTGTCATCTAGCAGAC, SEQ ID NO:17), respectively. The underlines denote the restriction enzyme sites in the primers. The amplified genes were individually cloned into the pET20b+ vector at the NdeI and XhoI restriction enzyme sites, which resulted in attaching a histidine (His)-Tag at the C-terminus of each of the gene products. In addition, the yscF, caf1, and lcrV fusion gene (YFV) was synthetically constructed by Epoch Biolabs, Inc. (Houston, Tex.) after codon optimization for E. coli by using Blue Heron Biotechnology (Bothell, Wash.) online service (https://wwws.blueheronbio.com). A flexible linker of 3× (GGGGS, SEQ ID NO:11) between YscF, Caf1 (F1), and LcrV domains was added to facilitate correct folding of the fusion protein. The fusion gene was similarly cloned into the pET20b+ vector with a His-Tag attached to the C-terminus of the YFV protein. Individual or the fusion genes were expressed from E. coli BL21(DE3) (New England BioLabs, Ipswich, Mass.) after induction with 0.5 mM IPTG (isopropyl-beta-D-thiogalactopyranoside) for 4 h at 37° C. The recombinant proteins (rYscF, rF1, rLcrV, and rYFV) were then purified by using $Ni^{2+}$-charged agarose (29). The recombinant F1 and LcrV fusion protein (rF1-V) was purchased from the BEI Resources, and used as a control for some of the experiments.

Construction of recombinant adenoviruses. The lcrV and the YFV fusion genes were codon optimized for expression in humans by using the Blue Heron Biotechnology online service, which also allowed us to optimize secondary structures of the corresponding RNAs and removal of unwanted sites for the restriction enzymes, except for those used for cloning purposes. The resulting constructs were designed to produce LcrV (37.2 kDa), as well as the YFV fusion protein consisting of YscF (9.5 kDa), mature form of F1 (15.6 kDa), and LcrV (37.2 kDa), interconnected via a flexible linker, as mentioned above. To improve expression of the corresponding genes, the Kozak consensus sequence was also placed upstream of the start codon. The constructs were then synthesized and verified via DNA sequence analysis by Epoch Biolabs, Inc. Each synthetic construct was cloned into pShuttleX vector (Clonetech Laboratories, Inc., Mountain View, Calif.) under the control of a CMV promoter.

To generate recombinant adenoviruses, the above gene constructs with their CMV promoters were removed from the pShuttleX vector and cloned into the replication-defective human type-5 adenovirus plasmid vector Adeno-X (Clonetech Laboratories, Inc.). The adenoviral constructs were created at the Baylor College of Medicine (BCM), Vector Development Laboratory, Houston, Tex. (available through the World Wide Web at the internet site maintained by the Vector Development Laboratory, for instance, bcm.edu/research/advanced-technology-core-labs/lab-listing/vector-development/adenovirus-vectors). The resulting recombinant plasmid vectors, Adeno-X/crV and Adeno-XYFV were transfected separately into human embryonic kidney 293 (HEK293) cells and the plaque formation was monitored. After small-scale expansion, eight plaques from each of the recombinant vector transfections were examined for the production of target proteins by dot blot analysis of the infected whole cell lysates with a monoclonal antibody to LcrV (mAb-LcrV) (BEI Resources). The positive plaques were selected and designated as rAd5-LcrV and rAd5-YFV, respectively. The control adenovirus Ad5-CMV-Empty without recombinant gene insertion was purchased from the BCM Vector Development Laboratory, and designated as Ad5-empty.

The Ad5-empty, rAdS-LcrV, and the rAd5-YFV were then expanded on a large scale by using HEK293 cells in a chemically-defined, protein-free CD-293 medium (Thermo Fisher Scientific, Waltham, Mass.) and purified at the BCM Vector Development Laboratory under GLP (good laboratory practice) conditions, and used for the subsequent studies. To examine expression of the target protein-encoding genes in the stocked recombinant viruses, A549 human lung epithelial cells (American Type Culture Collection, Manassas, Va.) were infected with Ad5 constructs at 1000 viral particles (v.p.) per cell. The host cell lysates were harvested after 24 h post-infection (p.i.). An aliquot of the cell lysates was then resolved by SDS-PAGE and subjected to Western blot analysis with mAb-LcrV antibody. The purified rLcrV and rYFV antigens were used as controls. As shown in FIG. 1, the size of the major band detected in the A549 cell lysate infected with either the rAdS-LcrV (lane 2) or rAdS-YFV (lane 3) corresponded to the size of purified rLcrV (lane 5) or rYFV (lane 6). No band was detected in the A549 cell lysate infected with the Ad5-empty (lane 4). The multiple bands detected in lanes 2, 3, and 6 most likely represented degradation, or incomplete synthesis of the target proteins.

Animal studies. Six-to-eight-week old, female Swiss-Webster mice (17 to 20 g) were purchased from Taconic Laboratories (Germantown, N.Y.). All of the animal studies were performed in the Animal Biosafety Level (ABSL)-3 facility within the Galveston National Laboratory (GNL) under approved Institutional Animal Care and Use Committee (IACUC) protocols.

1) Induction of Pre-Existing Immunity to Adenovirus in Mice.

To establish pre-existing immunity to adenovirus, animals received a single dose of the Ad5-Empty by i.m. injection of $8\times10^9$ v.p./100 μl into both quadriceps (50 μl each) 30 days prior to vaccination. Mice receiving saline (phosphate-buffered saline, PBS) served as a control. Blood was collected by the retro-orbital route before and 30 days after the Ad5-Empty injection, and microtiter plates pre-coated with 0.3 μg/well of Ad5-empty were used to evaluate antibody titers to adenovirus. Animals with pre-existing adenovirus immunity were designated as PreAd-mice.

2) Immunization of Mice with the Recombinant Proteins or Recombinant Ad5 Constructs.

Naïve mice (40 per group) were immunized with either the mixture of three recombinant proteins (rYscF, rF1, and rLcrV, 25 μg/each) or 45 μg of the corresponding recombinant fusion protein (rYFV) via the i.m. route. The antigens were emulsified 1:1 in Imject Alum adjuvant (Pierce Companies, Dallas, Tex.). One primary immunization and two identical boosters were given on days 0, 15 and 30. Naïve mice receiving adjuvant alone served as a control. For the recombinant Ad5 constructs, naïve mice or preAd-mice (40 per group) were either i.m. or i.n. immunized with one dose ($8\times10^9$ v.p) of rAd5-LcrV monovalent or rAd5-YFV trivalent vaccine. Control animals (both naïve and preAd-mice) received the same dose of Ad5-empty via the same route as their corresponding immunized mice. In some cases, the dose of Ad5-Empty was split equally into i.m. injection and i.n. instillation for the control naïve mice. During i.m.

immunizations, the dose in a 100 μl volume was equally split and injected into both quadriceps, while for the i.n. immunizations, the dose in 40 μl was equally distributed into each of the nares of mice followed by 20 μl of PBS wash.

3) Immunization of Mice with the Combination of rAd5-YFV and rYFV.

PreAd-mice (20 per group) were first i.n. immunized with $8\times10^9$ v.p./40 μl of rAd5-YFV trivalent vaccine and then followed (two weeks later) by i.m. immunization with 10 μg rYFV (emulsified 1:1 in Alum adjuvant). PreAd-mice immunized with either 10 μg of rYFV or $8\times10^9$ v.p./40 μl of rAd5-YFV alone were used for comparison, and PreAd-mice without further immunizations served as a negative control.

4) Evaluation of Antibody Titers in Mice.

Blood was collected by the retro-orbital route from all vaccinated and control mice at day 0 and after 12-15 days of last vaccination. Sera were separated and the antigen-specific antibodies were then evaluated. Briefly, ELISA plates were pre-coated with 200 ng/well of the recombinant proteins (e.g., rLcrV, rF1 or rYscF). Two-fold serially diluted sera was then added in the wells of the ELISA microtiter plates, followed by the addition of secondary horseradish peroxidase (HRP)-conjugated anti-mouse specific antibodies to IgG, its isotypes, and/or IgA. The ELISA was performed as we described previously (30).

5) T-Cell Responses.

T cells were isolated from splenocytes of PreAd-mice (n=5) immunized with either rAd5-YFV (i.n., $8\times10^9$ v.p) alone or in a prime-boost combination with rYFV (10 i.m.) on day 15 after the last immunization. The isolated T cells were co-cultured with γ-irradiated splenocytes from naïve mice (severed as antigen-presenting cells [APCs]) pulsed or un-pulsed with F1-V fusion protein, 100 μg/ml. After 72 h of incubation, 1 μCi of [$^3$H] thymidine was added into each well, and the cells harvested 16 h later using a semi-automated sample harvester, FilterMate Harvester (PerkinElmer, Waltham, Mass.), followed by the measurement of radioactive counts (TopCount NXT, PerkinElmer) as we previously described (31, 32). To measure interferon (IFN)-γ producing T cells, the isolated T cells were incubated with the pulsed and un-pulsed APCs for 2 days and evaluated by the enzyme-linked immunospot (Elispot) assay (R&D Systems Inc., Minneapolis, Minn.).

6) Challenge and Re-Challenge.

Mice were challenged with WT CO92 on day 14-15 post last vaccination by either the subcutaneous (s.c.), i.n., or the aerosol route as we previously described (28, 33). Aerosolization was performed using a 6-jet Collison nebulizer attached to a whole-body mouse aerosol chamber. The challenge doses ranged from 24 to 8,500 $LD_{50}$ for the s.c. route and 21 to 800 $LD_{50}$ for the i.n. route. The presented dose (Dp) for the aerosol challenge was calculated to be in the range of 3.14 to $6.34\times10^5$ colony forming units (CFU). The $LD_{50}$ of WT CO92 for Swiss-Webster mice is ~50 CFU for developing bubonic plague (s.c.), ~500 CFU for inducing pneumonic plague (i.n.), and ~Dp of 2100 CFU for the aerosol route (28, 32). For the re-challenge experiment(s), on day 32 after the initial WT CO92 aerosol challenge, the vaccinated mice that survived were infected i.n. with 100 $LD_{50}$ of the WT CO92 luc2 strain. The age matched naïve mice served as a control. The animals were imaged on day 3 p.i. with WT CO92 luc2 strain by using an in vivo imaging system (IVIS) 200 bioluminescent and fluorescence whole-body imaging workstation (Caliper Corp. Alameda, Calif.) in the ABSL-3 facility.

Non-human primate (NHPs) study. Cynomolgus macaques (2.5-3.5 kg, males) were purchased from Prelabs, Hines, Ill. The NHPs were sedated by the administration of ketamine i.m. during the procedures, and all of the studies were performed in the ABSL-3 facility under an approved IACUC protocol.

1) Induction of Pre-Existing Immunity to Adenovirus and Immunization.

To induce pre-existing immunity, four randomly selected NHPs were injected in the left quadriceps muscle with $5\times10^{10}$ v.p./250 μl of Ad5-Empty (day 0). After 30 days, these NHPs were i.n. immunized with $1\times10^{11}$ v.p./500 μl of rAd5-YFV, followed by 50 μg/250 μl of rYFV boost (emulsified 1:1 in Alum adjuvant) via the i.m. route on day 42. In the control group, four NHPs received 250-500 μl of saline at days 0, 30 and 42 via the same routes as the immunized NHPs, and served as controls (Table 1). The nasal administration of rAd5-YFV was performed by using a Mucosal Atomization Device (MAD Nasal, Wolfe Tory Medical, Inc., Salt Lake City, Utah) that delivers intranasal medication in a fine mist, thus enhancing the absorption and improving bioavailability.

TABLE 1

NHP immunization and challenge timeline

| Group (size) | Induction of preexisting anti-adenovirus immunity (Day 0) | Prime vaccination (Day 30) | Boost with rYFV (Day 42) | Aerosol Challenge (Day 85) |
|---|---|---|---|---|
| Immunized (4) | $5\times10^{10}$ v.p./250 μl Ad5-empty i.m. route | $1\times10^{11}$ v.p./500 μl rAd5-YFV i.n. route (250 μl per nostril) | 50 μg of the rYFV mixed with alhydrogel (250 μl) given by the i.m. route | WT CO92 (Dp: 1.32 to $8.08\times10^7$ CFU) |
| Control (4) | Saline (250 μl) i.m. route | Saline (500 μl) i.n. route (250 μl per nostril) | Saline (250 μl) i.m. route | |

2) Aerosol Challenge.

The immunized and control NHPs were challenged with WT CO92 by the aerosol route on day 85 (Table 1). Briefly, WT CO92 was aerosolized with a 6-jet Collison nebulizer. The nebulizer was attached to a head-only NHP aerosol exposure box and real-time plethysmography was performed on each of the anesthetized NHP during aerosol challenge. The aerosol/plethysmography system was controlled by a Biaera AeroMP aerosol platform (Biaera Technologies, LLC Hagerstown, Md.) integrated with a respiratory inductive plethysmography (RIP) system (Data Sciences International St. Paul, Minn.). Aerosol samples were collected during each animal exposure by using all glass BioSamplers to assure accurate aerosol delivery, and the corresponding Dps were calculated (28, 34).

The NHPs were monitored and evaluated closely for developing clinical signs of the disease. Clinical scores were provided after thorough examination of the animals by the veterinarian staff. The NHPs were euthanized when they were found with a clinical score of 8 and above. The parameters examined but not limited to included absence of grooming, decreased breathing, and non-responsive to human presence at cage side. All NHP exposures to aerosols of WT CO92 were performed in our ABSL-3 facility within the GNL in a specialized aerobiology suite equipped with a Class III biosafety glove cabinet.

3) Antibody Titers, Blood Cell Counts, and Bacterial Burden.

Blood samples were collected from the femoral veins of NHPs at various time points during the experiment. Antibody titers to Ad5, LcrV, F1, and YscF on days 0, 42, 56, 85, 98 and 112 were evaluated by ELISA as we described above. The last two time points (days 98 and 112) corresponded to days 14 and 28 after WT CO92 challenge. Blood cell counts were analyzed on the day of WT CO92 challenge (day 85) and on days 3 and 6 post challenge by using a Drew Scientific Hemavet 950 hematology system (Drew Scientific, Inc., Dallas, Tex.). The bacterial loads were evaluated by plating the blood samples which were drawn when control NHPs were euthanized (on day 3 or 4 post WT CO92 challenge) or at various time points (e.g., days 3, 6, 14, 28, 70, and 82) post WT CO92 challenge in the case of immunized NHPs.

4) Necropsy and Histopathological Analysis.

After euthanasia, necropsies were performed by the certified chief biocontainment veterinarian at UTMB. NHP organs, such as lungs, liver, spleen, and the lymph nodes (hilar, submandibular, and mediastinal) were removed and grossly examined. A portion of these organs was homogenized and plated for assessing bacterial load (35), while another portion was fixed in 10% neutral buffered formalin (33, 36) and tissues processed and sectioned at 5 μm. The samples were mounted on slides and stained with hematoxylin and eosin (H&E). Sections from the lungs were also subjected to Gram stain to examine the presence of plague bacilli. Tissue lesions were scored on the basis of a severity scale, which correlated with estimates of lesion distribution and the extent of tissue involvement (minimal, 2 to 10%; mild, >10 to 20%; moderate, >20 to 50%; severe, >50%), as previously described (33, 36). The histopathological evaluation of the tissue sections was performed in a blinded fashion.

CT scans. CereTom NL 3000 (Neurologica, MA), which is an eight-slice tomography with high-contrast resolution of 0.6 mm (developed for human head imaging in ICU), was used. The image acquisition settings were: tube voltage, 100 kV; tube current, 5 mA; and axial mode with slice thickness of 1.25 mm. Image resolution was 512×512 pixels. The image sharpness was optimized to soft tissue.

Statistical analysis. Two-way analysis of variance (ANOVA) with the Tukey's post hoc test or the multiple Student's t-test with the Holm-sidak post hoc test correction was used for data analysis. We used Kaplan-Meier survival estimates for animal studies, and p values of ≤0.05 were considered significant for all of the statistical tests used.

Results

Figure 8A:
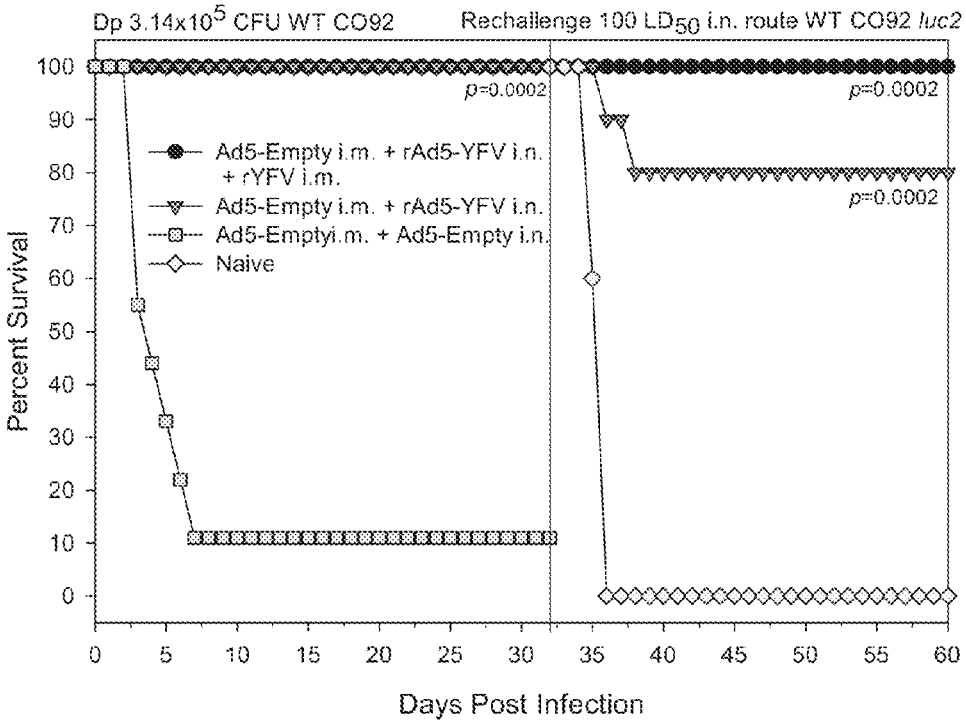
FIG. 8A-8B-02 shows immunization of mice with the rAd5-YFV vaccine alone or in combination with rYFV provided protection against lethal primary aerosol and subsequent intranasal WT CO92 challenges. PreAd-mice (n=10) were either i.n.-immunized with $8\times10^9$ v.p./40 μl of rAd5-YFV alone or in the combination with 10 μg of rYFV (emulsified 1:1 in Alum adjuvant) i.m. The immunizations occurred two weeks apart. PreAd-mice injected with Ad5-Empty served as a negative control. After 15 days post immunization, mice were first challenged with aerosolized WT CO92 at a Dp of $4.62\times10^5$ CFU. After 32 days of the initial aerosol challenge, the survivals from the immunized groups along with five age-matched uninfected naïve mice were infected with 100 $LD_{50}$ of WT CO92 luc2 strain by the i.n. route. The deaths were recorded for the initial aerosol and then the subsequent intranasal challenge, and the percentages of survival were plotted (FIG. 8A). The P values were in comparison to the control group for each challenge and were based on Kaplan-Meier Curve Analysis. The animals were also imaged by IVIS for bioluminescence on day 3 after WT CO92 luc2 strain i.n. challenge (FIGS. 8B-01 and 8B-02). Panel B-I represented infected naïve mice as i.n. challenge control and the very right animal in this panel was uninfected image control. Panel B-II, animals immunized with the prime-boost strategy, and panel B-III, animals immunized with rAd5-YFV vaccine alone. The bioluminescence scale is within the figures and ranged from most intense (top of range) to least intense (bottom of range).
Figures 1, 8B:
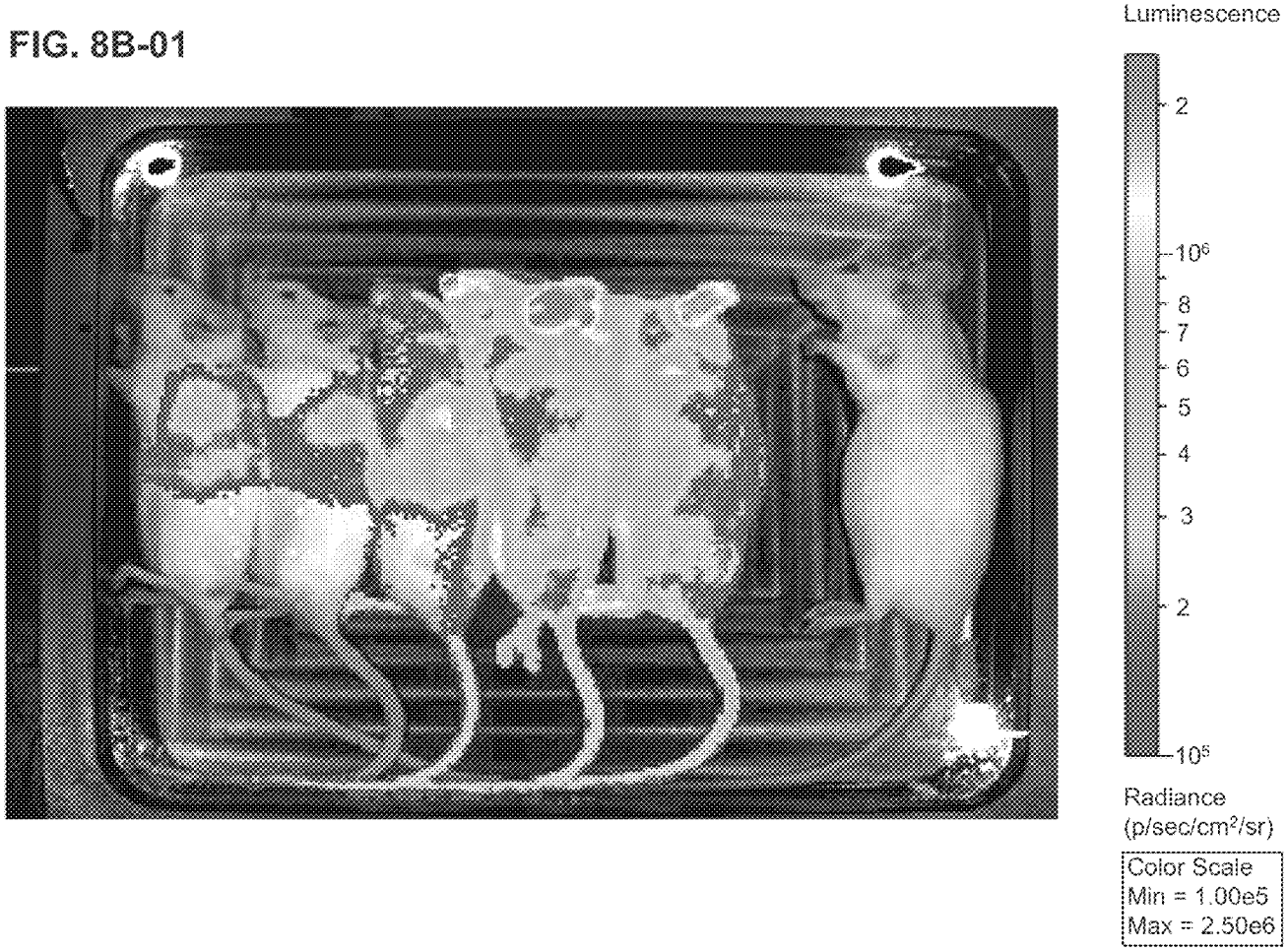
Figures 2, 8B:
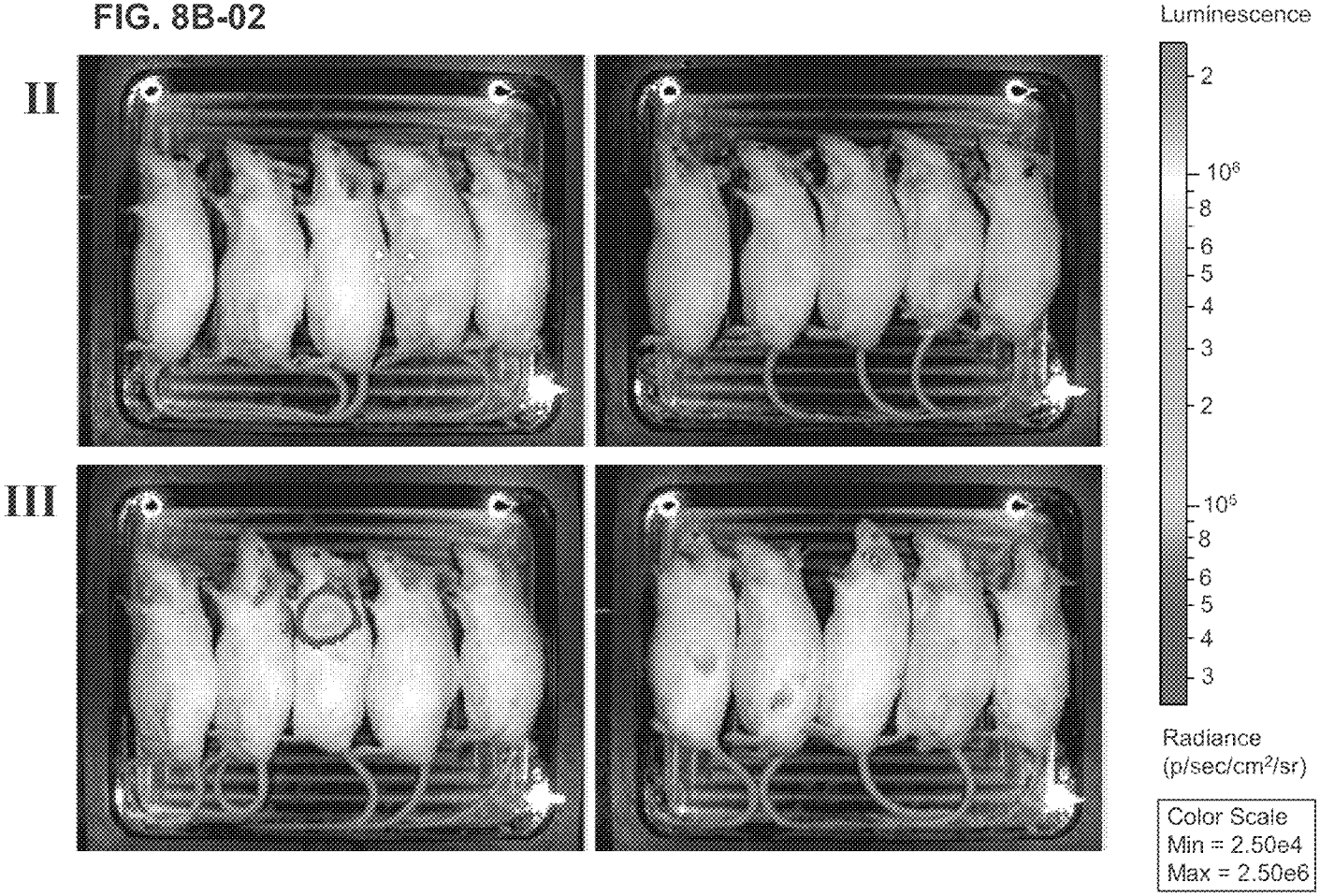

Immunogenicity of rYFV fusion protein. Mice were i.m. immunized with either the mixture of recombinant proteins (rYscF+rF1+rLcrV) or the fusion protein rYFV. Both recombinant proteins (rYFV or rYscF+rF1+rLcrV) conferred 100% protection to mice when challenged by either the s.c. route (8500 $LD_{50}$, to induce bubonic plague) or the i.n. route (800 $LD_{50}$, to induce pneumonic plague) with WT CO92, while developing significant antibody titers to LcrV (FIG. 2).

Figure 3A:
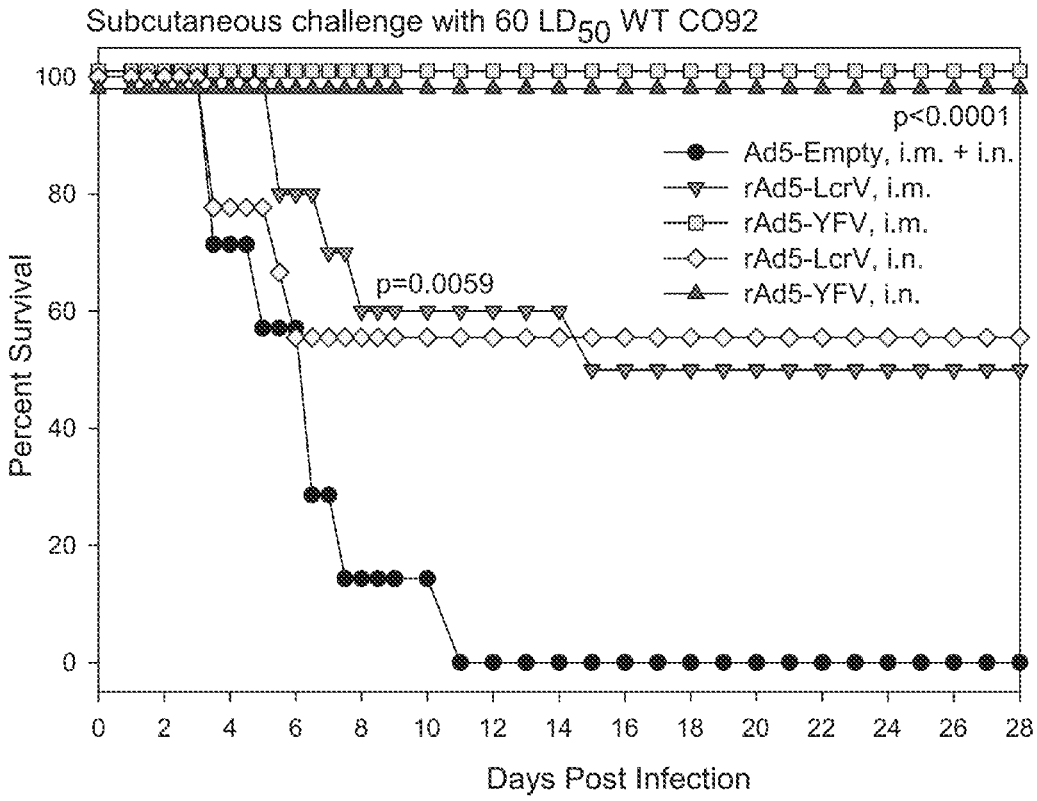
FIG. 3A-3C shows immunization routes comparison in mice. Naïve mice (n=40) were either i.m. or i.n. immunized with one dose ($8\times10^9$ v.p) of rAd5-LcrV or rAd5-YFV vaccines. Animals received the same dose of Ad5-Empty which was split equally into i.m. injection and i.n. instillation, and served as a control. The above immunized and control mice were then divided into two sets and challenged on day 15 post immunization either subcutaneously (s.c.) with 60 $LD_{50}$ (FIG. 3A) or intranasally (i.n.) with 90 $LD_{50}$ (FIG. 3B) of the WT CO92. The P values were in comparison to the control group and were based on Kaplan-Meier Curve Analysis. Mice were also bled prior to the challenge to evaluate IgG antibody titers and that of its isotypes to LcrV by ELISA (FIG. 3C). The P values were in comparison to the indicated groups and were based on Two-way ANOVA (IgG1 and IgA) with the Tukey's post hoc correction.
Figure 3B:
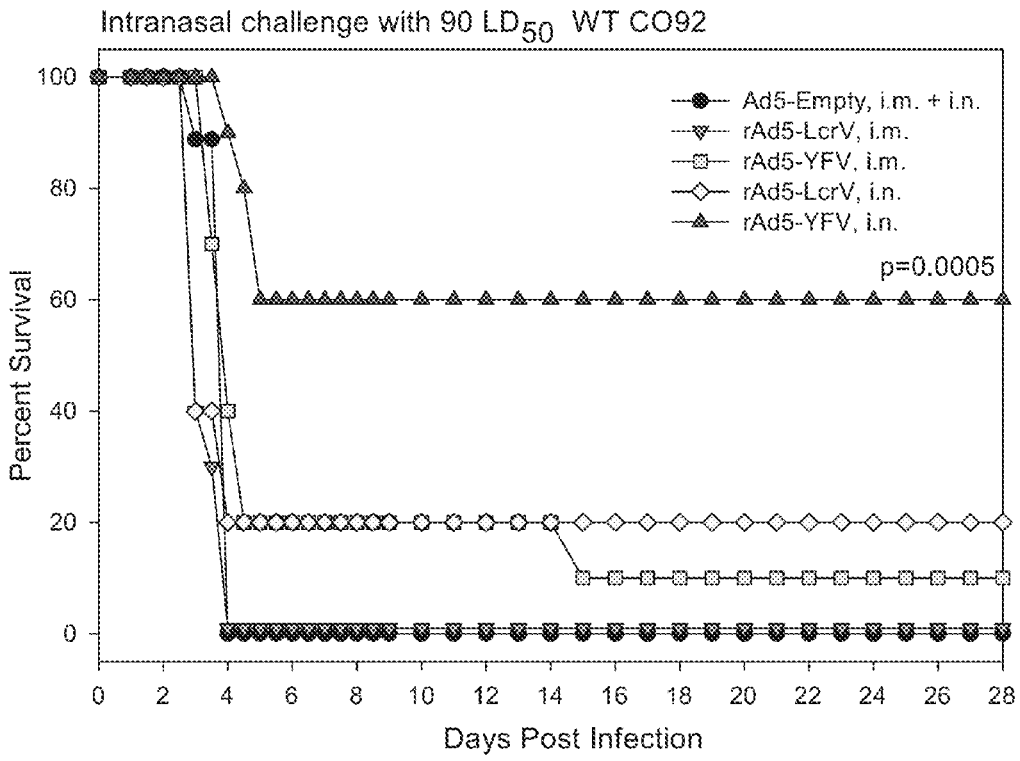

Protective immunity of the recombinant adenoviruses in both bubonic and pneumonic plague mouse models. Mice were immunized i.m. or i.n. with rAd5-LcrV monovalent or rAd5-YFV trivalent vaccines to evaluate their potential to protect animals from plague. Irrespective of the immunization route, mice that were administered rAd5-YFV trivalent vaccine displayed 100% protection when challenged with 60 $LD_{50}$ of WT CO92 in a bubonic plague model (FIG. 3A) However, only 50 to 55% of mice receiving the rAd5-LcrV monovalent vaccine were protected and all control mice died by day 11 p.i. (FIG. 3A). In a more stringent pneumonic plague model (90 $LD_{50}$ of WT CO92), animals vaccinated by the i.n. route with rAd5-YFV trivalent vaccine were 60% protected, while the survival rate declined to 10% when immunization occurred by the i.m. route (FIG. 3B). In comparison, either none or 20% of the animals immunized with the Ad5-LcrV monovalent vaccine survived when vaccination occurred by i.m. versus the i.n. route. Overall, these data indicated vaccines to be more effective when instilled by the i.n. route. The corresponding control mice (receiving Ad5-empty by the i.m. or the i.n. route) succumbed to infection by day 4 p.i. (FIG. 3B).

Figure 2A:
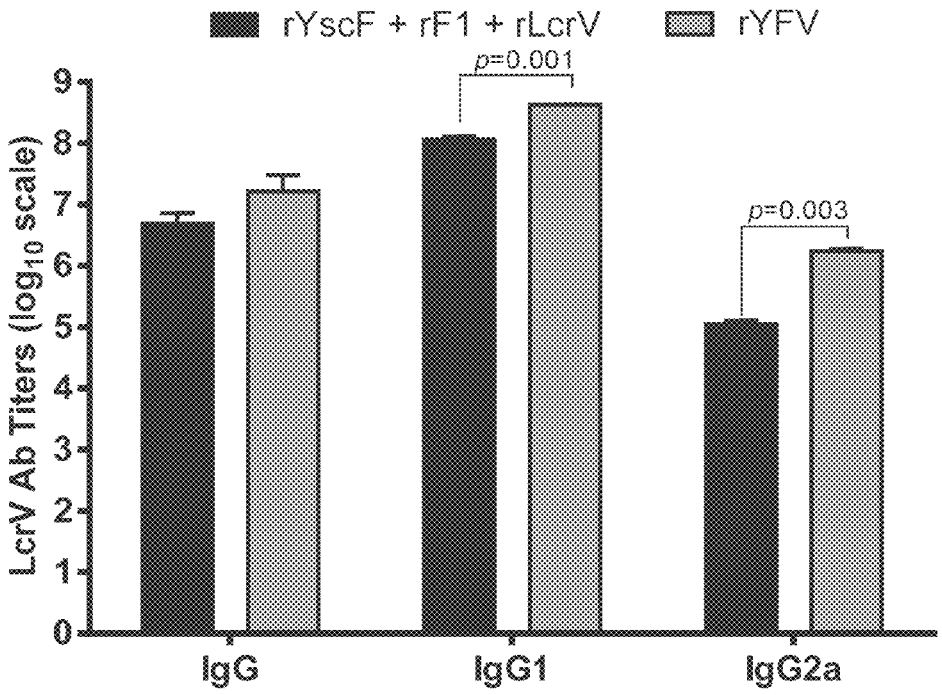
FIG. 2A-2C shows protection conferred by immunization of mice with the purified recombinant proteins. Naïve mice (n=40) were immunized with either the mixture of three recombinant proteins (rYscF, rF1, and rLcrV, 25 μg/each) or 45 μg of the corresponding recombinant fusion protein (rYFV) via the i.m route. The antigens were emulsified 1:1 in Alum adjuvant. One primary immunization and two identical boosters were given on days 0, 15 and 30. Naïve mice received the adjuvant only and served as a control. Mice were bled 14 days post last immunization and an ELISA was performed to examine IgG and its isotype antibody titers to the LcrV antigen (FIG. 2A). The P values were in comparison to the indicated groups and were based on Two-way ANOVA (IgG1 and IgG2a) with the Tukey's post hoc correction. The above immunized and control mice were then split into two sets and challenged on day 15 post immunization either subcutaneously (s.c.) with 8500 $LD_{50}$ (FIG. 2B) or intranasally (i.n.) with 800 $LD_{50}$ (FIG. 2C) of the WT CO92. The P values were in comparison to the control group and were based on Kaplan-Meier Curve Analysis.
Figure 2B:
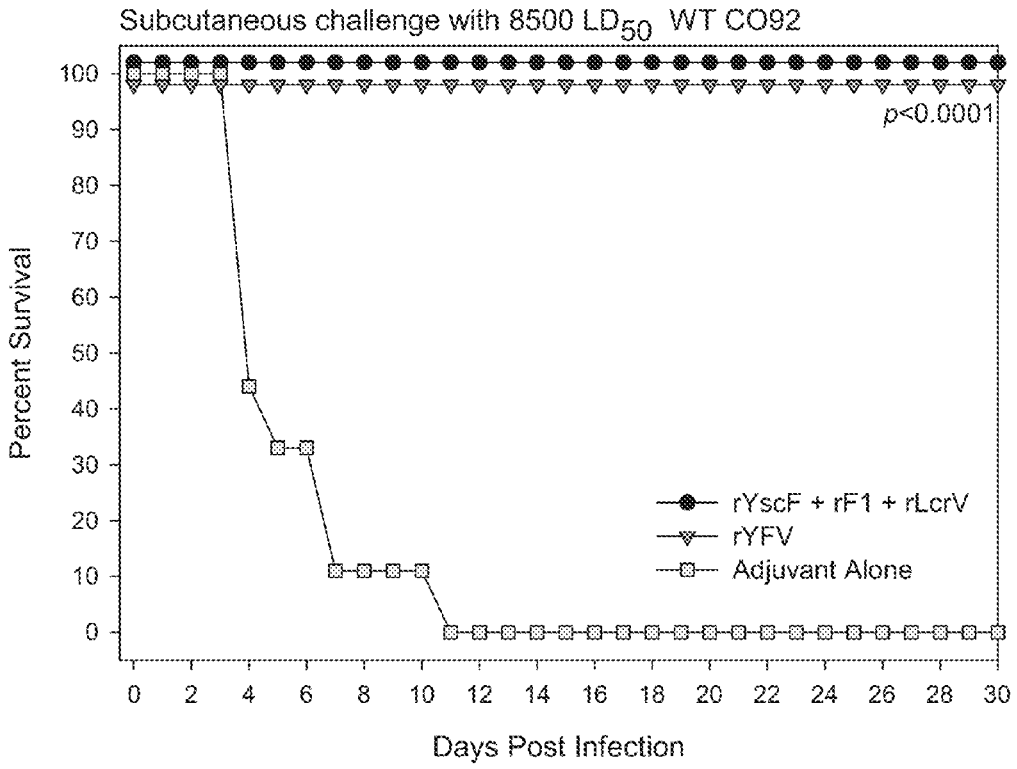
Figure 2C:
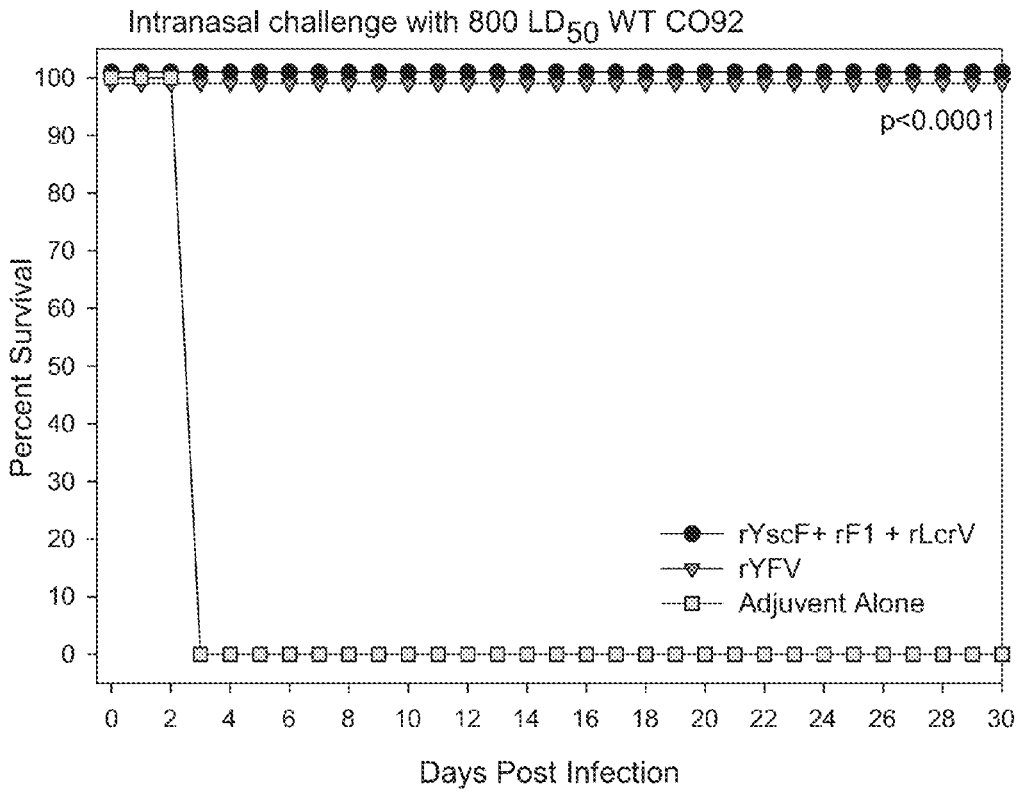
Figure 3C:
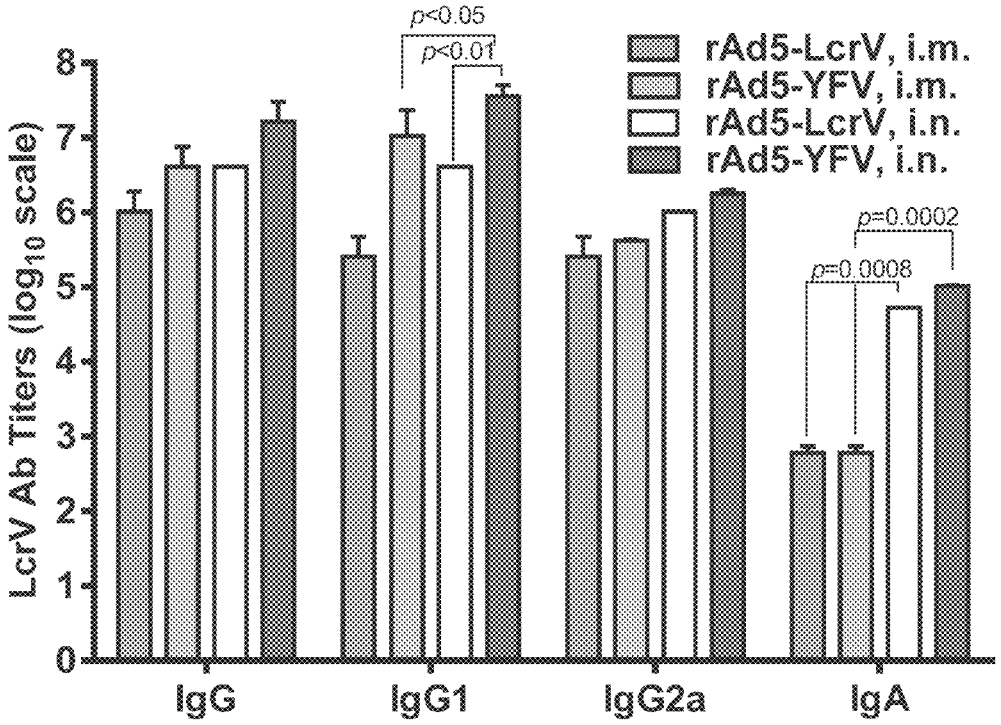

Higher antibody titers to LcrV were generally observed in mice that received the rAd5-YFV trivalent vaccine when compared to that of the rAd5-LcrV monovalent vaccine-immunized animals, reaching statistically significant levels for IgG1 in mice that were immunized by the i.n. route (FIG. 3C). In terms of immunization routes, i.n. vaccinated mice overall had superior antibody titers when compared to animals immunized by the i.m. route, reaching statistical significance for the production of IgG1 and IgA (FIG. 3C). Irrespective of the recombinant virus used and route of immunization, all of the vaccinated mice developed a more balanced Th1 and Th2 type antibody responses when compared to immunization of animals with the recombinant proteins (FIGS. 2A and 3C).

Figure 4A:
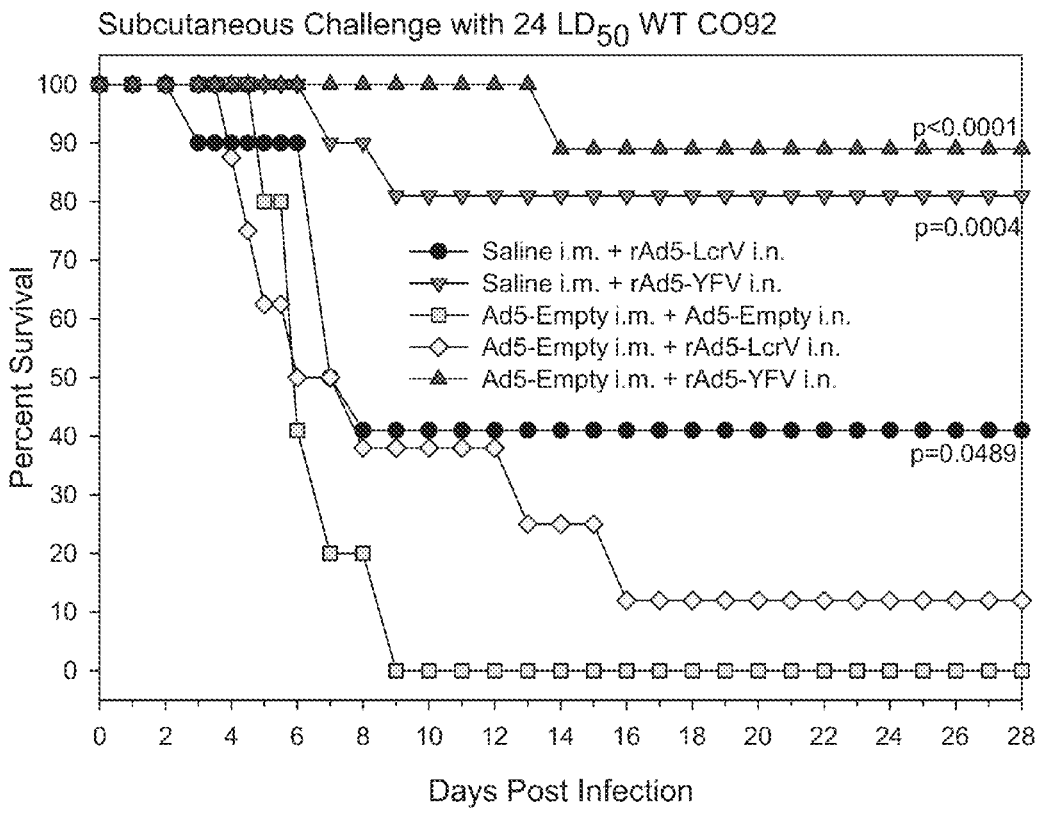
FIG. 4A-4C shows protection conferred by immunization with the recombinant adenoviruses in mice that had pre-existing immunity to adenovirus. To establish pre-existing immunity to adenovirus, naïve mice (n=40) received a single dose ($8\times10^9$ v.p./100 μl) in both quadriceps (50 μl each) of the Ad5-Empty by i.m. injection 30 days prior to vaccination. Naïve mice receiving saline served as a control. Subsequently, mice were i.n. immunized with one dose ($8\times10^9$ v.p) of rAd5-LcrV or rAd5-YFV vaccines. Animals received the same dose of Ad5-Empty by i.n. instillation, and served as a negative control. The above mice were then divided into two sets and challenged on day 15 post immunization either subcutaneously (s.c.) with 24 $LD_{50}$ (FIG. 4A) or intranasally (i.n.) with 21 $LD_{50}$ (FIG. 4B) of the WT CO92. The P values were in comparison to the negative control group and were based on Kaplan-Meier Curve Analysis. Mice were also bled prior to the challenge to evaluate IgG antibody titers, titers to its isotypes, and IgA to LcrV by ELISA (FIG. 4C). The P values were in comparison to the indicated groups and were based on Two-way ANOVA with the Tukey's post hoc correction. The asterisks indicated statistical significance compared to the control (Ad5-Empty) mice for IgA levels by using multiple Student's t-test with the Holm-sidak post hoc test correction.
Figure 4B:
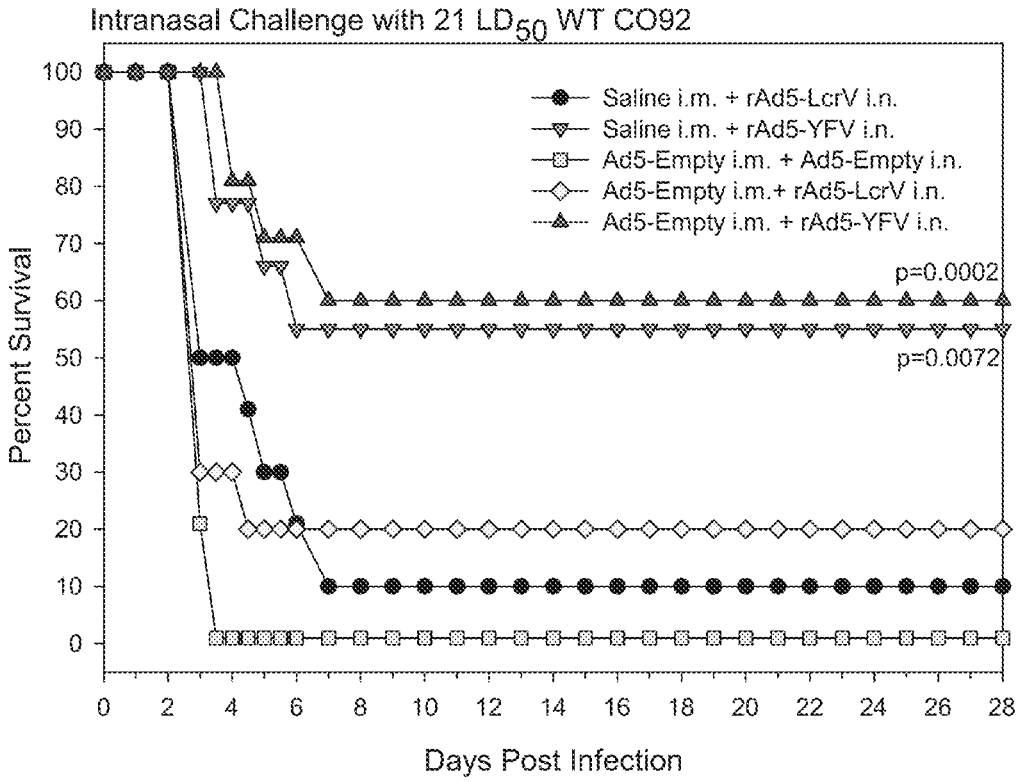

Pre-existing immunity to adenovirus in mice. The adenoviral antibody titers on day 30 after injection of Ad5-empty in mice ranged from 102,400 to 819,200. In a bubonic plague model, at a 24 $LD_{50}$ challenge dose, a similar level of protection (80 to 90%) was noted in mice immunized with rAd5-YFV trivalent vaccine, irrespective of whether or not pre-existing antibodies to adenovirus were developed (FIG. 4A). In contrast, the survival rate was 40% in mice without pre-existing Ad5 antibodies and only 10% in preAd-mice when immunization occurred with the rAd5-LcrV monovalent vaccine (FIG. 4A). In a pneumonic plague model (21 $LD_{50}$), rAd5-YFV-immunized mice with or without pre-existing immunity to Ad5 exhibited a similar 55-60% survival rate which was much higher than in mice immunized with the rAd5-LcrV monovalent vaccine with or without pre-immunity to Ad5 (10-20% protection) (FIG. 4B). All of the control mice died on the indicated days in a bubonic or pneumonic plague model (FIGS. 4A and 4B).

Figure 4C:
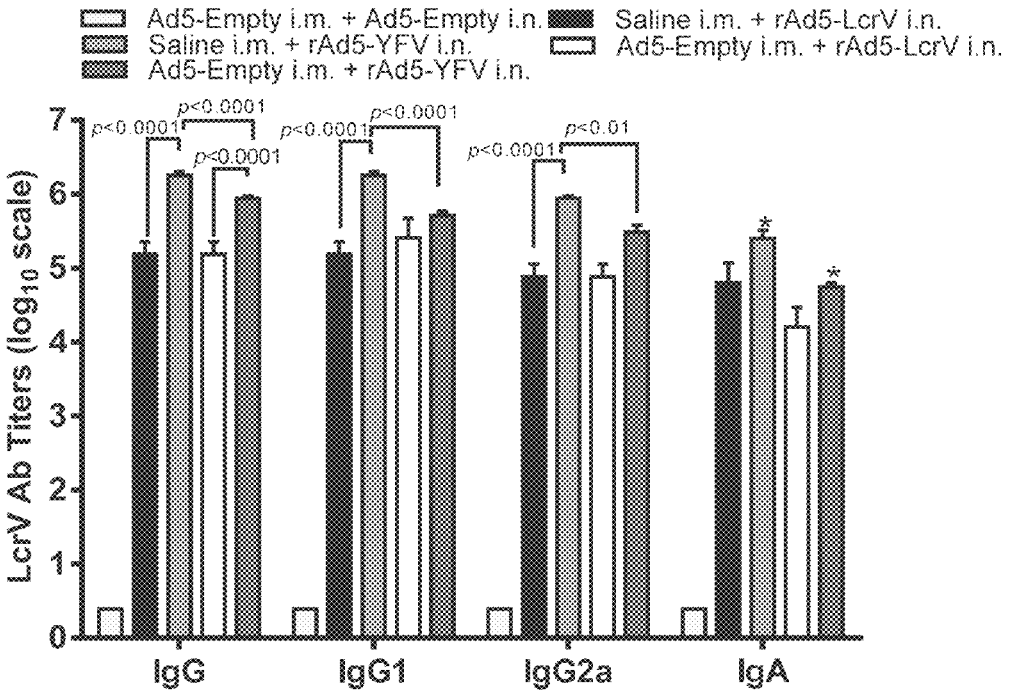

Balanced Th1 and Th2 type antibody responses with robust titers to LcrV were observed across all immunized mice (FIG. 4C). However, two important observations were drawn from this study: 1) compared to rAd5-LcrV monovalent vaccine immunized mice, animals that were vaccinated with the rAd5-YFV trivalent vaccine generally developed better antibody titers (both IgG and its isotypes as well as IgA) to LcrV, although some did not reach statistical significance (e.g., IgG1 and IgG2a in preAd-mice as well as IgA), and 2) mice without pre-existing adenoviral immunity developed slightly higher IgG and IgA antibody titers to LcrV compared to that of preAd-mice receiving the trivalent rAd5-YFV vaccination, although only total IgG and its isotopes reached statistical significance (FIG. 4C). As expected, none of the unimmunized control mice developed any detectable level of protective anti-LcrV antibodies, and, thus, succumbed to infection (FIGS. 4A and 4B). Importantly, in spite of slight lower antibody titers to LcrV in mice with pre-existing Ad5 antibodies, animals were similarly protected when the Ad5 -YFV trivalent vaccine was administered by the i.n. route against challenge with WT CO92 in both bubonic and pneumonic plague models (FIGS. 4A and 4B).

Figure 5:
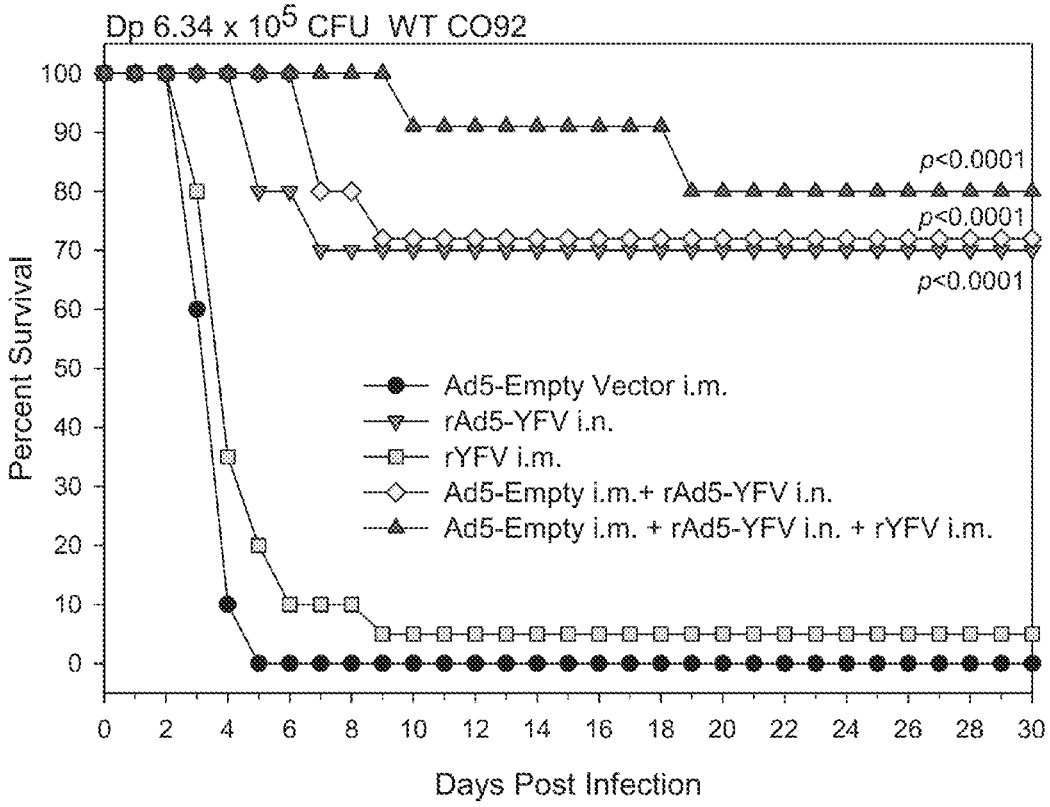
FIG. 5 shows prime-boost immunization provided better protection to mice against lethal WT CO92 aerosol challenge. PreAd-mice (groups of 20) were either i.n.-immunized with $8\times10^9$ v.p./40 μl of rAd5-YFV alone or in the combination with 10 μg of rYFV (emulsified 1:1 in Alum adjuvant) i.m. The immunization occurred two weeks apart. Naïve mice immunized with either 10 μg of rYFV (i.m) or $8\times10^9$ v.p./40 μl (i.n.) of rAd5-YFV alone were used for comparison, and PreAd-mice without further immunizations served as a negative control. After 15 days post immunization, mice were challenged by the aerosol route with WT CO92 at a Dp of $6.34\times10^5$ CFU. The P values were in comparison to the negative control group and were based on Kaplan-Meier Curve Analysis.

Prime-boost and aerosol challenge. Our above data indicated that the trivalent rAd5-YFV vaccine was better than the monovalent rAd5-LcrV vaccine in providing protection to mice against Y. pestis infection. However, the overall protection rate did not reach 100% in the pneumonic plague model (FIGS. 3B and 4B). To enhance protection, a boost with rYFV (10 μs) was administered to mice i.m. two weeks later following i.n. instillation of the rAd5-YFV trivalent vaccine. As shown in FIG. 5, mice immunized with only rAd5-YFV had a 70% survival rate after aerosol exposure of WT CO92, irrespective of whether or not pre-existing adenoviral immunity was developed. The preAd-mice vaccinated with the combination of rAd5-YFV and rYFV displayed a protection rate of 80% with an overall delayed death pattern after WT CO92 aerosol challenge at a Dp of $6.34\times10^5$ CFU (~302 $LD_{50}$). The rYFV-immunized mice alone (single dose, no boosts) had 5% survival, and all unimmunized preAd-mice died after aerosol exposure of the pathogen between days 3 to 5 p.i. (FIG. 5).

Figure 6A:
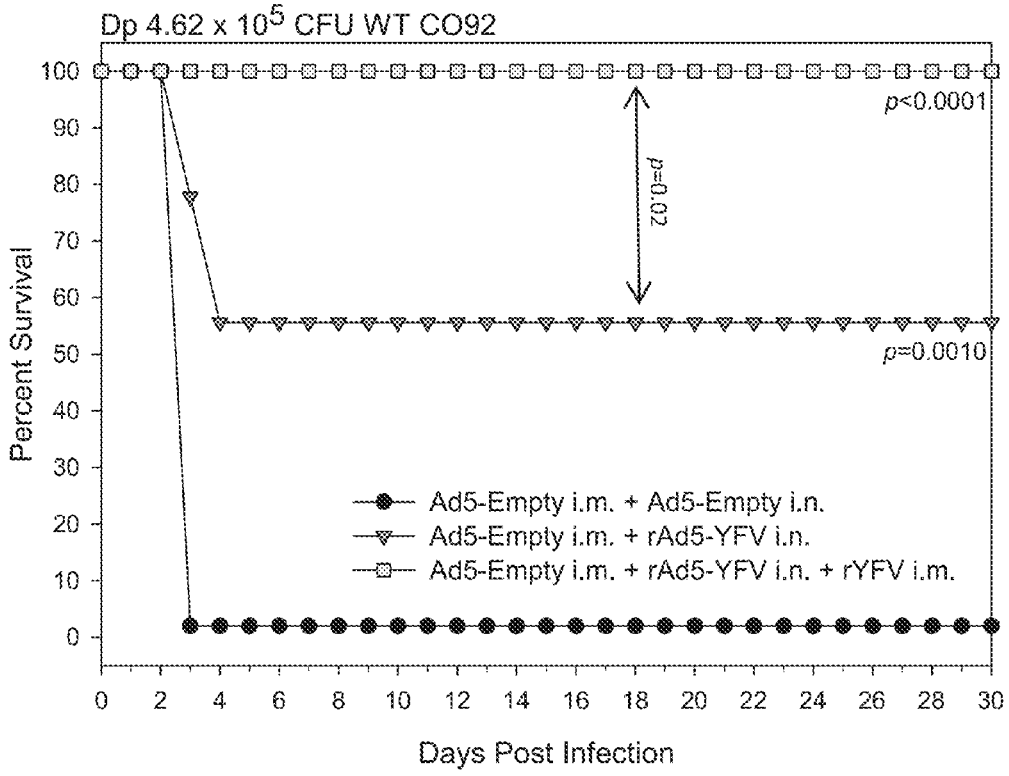
FIG. 6A-6C. T cell mediated immune response in mice elicited by immunization with the rAd5-YFV vaccine alone or in combination with rYFV. PreAd-mice (n=10-25) were either i.n. immunized with $8\times10^9$ v.p./40 μl of rAd5-YFV alone or in the combination with 10 μg of rYFV (emulsified 1:1 in Alum adjuvant) i.m. The immunizations occurred two weeks apart. After 15 days post immunization, 20 mice from each immunized and 10 from control group were aerosol challenged with WT CO92 at a Dp of $4.62\times10^5$ CFU. The P values were in comparison to the negative control group or between groups (as indicated by the arrow) and were based on Kaplan-Meier Curve Analysis (FIG. 6A). On day 15 post last immunization, T cells were isolated separately from the spleens of remaining unchallenged 5 mice in each immunized group. The isolated T cells were co-cultured with γ-irradiated APCs pulsed or un-pulsed with F1-V fusion protein (100 μg/ml). The IFN-γ producing T cells were measured after 2 days of incubation with the APCs by using the enzyme-linked immunospot (Elispot) assay (FIG. 6B). T cell proliferation was assessed by measuring incorporation of [$^3$H] thymidine on day 3 of co-culture with the APCs (FIG. 6C). The arithmetic means±standard deviations were plotted. Data were analyzed by using Two-way ANOVA with the Tukey's post hoc correction. The statistical significance was indicated by asterisks in comparison of the pulsed and un-pulsed T cells within each group or displayed by a horizontal line with the P value.

To further evaluate the potential of the prime-boost strategy, another set of immunized mice were exposed to a slightly lower WT CO92 aerosol challenge dose (Dp of $4.62\times10^5$ CFU, ~220 $LD_{50}$). As shown in FIG. 6A, the preAd-mice first vaccinated with the rAd5-YFV trivalent vaccine and then boosted with rYFV, were 100% protected against developing pneumonic plague. On the other hand, preAd-mice that were vaccinated with only the rAd5-YFV trivalent vaccine showed 55% survival rate, with all the unimmunized preAd-mice succumbed to infection by day 3 post challenge.

Figure 6B:
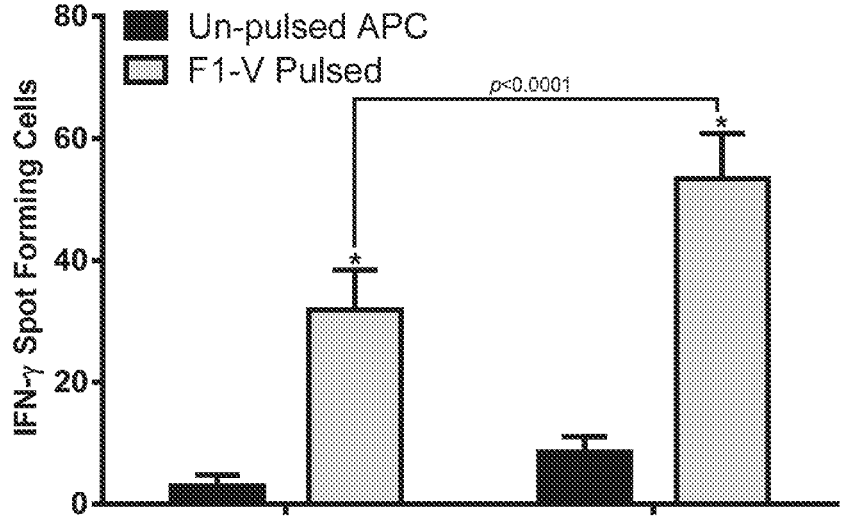
Figure 6C:
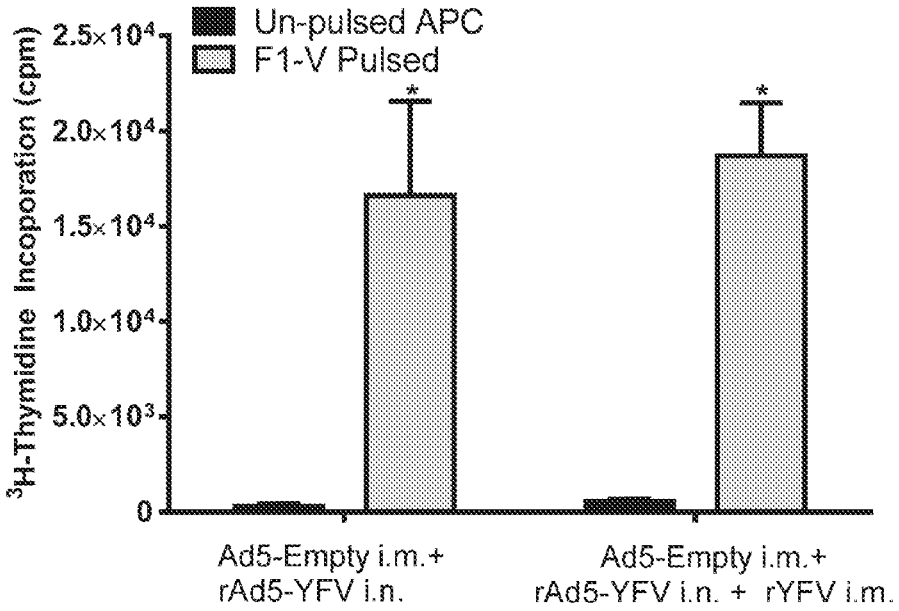

In addition, 55-60% of T cells isolated from the prime-boost group of mice were IFN-γ positive, while this number was only 30% for mice that were immunized with rAd5-YFV trivalent vaccine alone (FIG. 6B). However, there was no difference between the two immunized groups of mice (with or without the prime-boost) in terms of their T cell proliferative responses upon stimulation with the F1-V antigen (FIG. 6C).

Figure 7A:
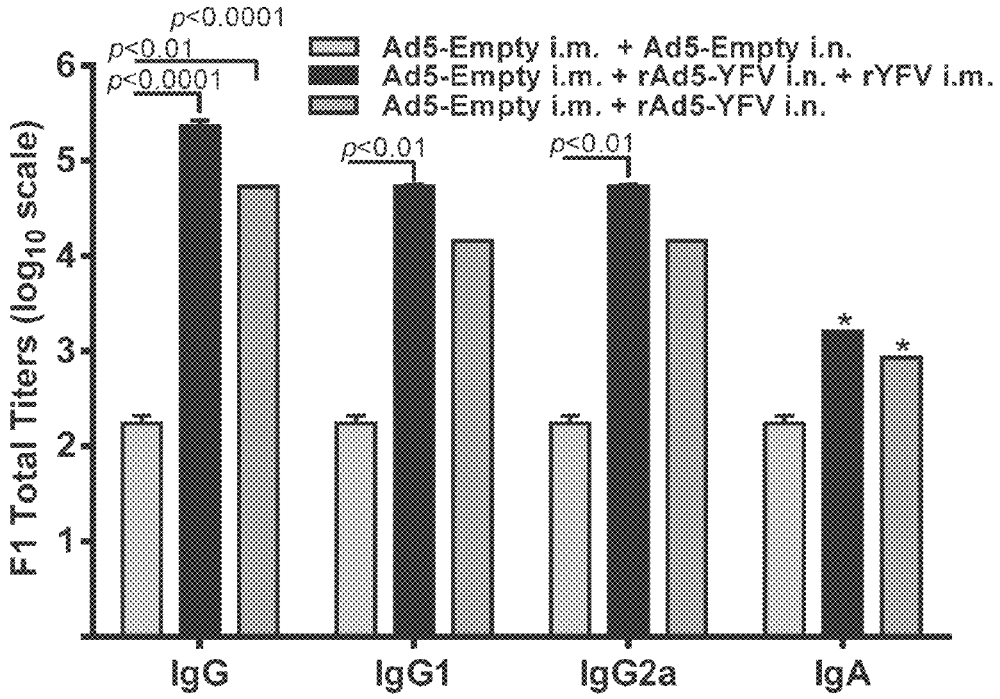
FIG. 7A-7C shows antibody responses in mice elicited by immunization with the rAd5-YFV vaccine alone or in combination with rYFV. Mice from different groups (FIG. 6A-6C) were also bled 15 days post immunization, and an ELISA was performed to examine IgG antibody titers, its isotypes, and IgA to the F1 (FIG. 7A), LcrV (FIG. 7B) and YscF (FIG. 7C), respectively. The P values were in comparison to the indicated groups and based on Two-way ANOVA with the Tukey's post hoc correction. The asterisks indicated statistical significance compared to the control (Ad5-Empty) mice for IgA levels by using multiple Student's t-test with the Holm-sidak post hoc test correction.
Figure 7B:
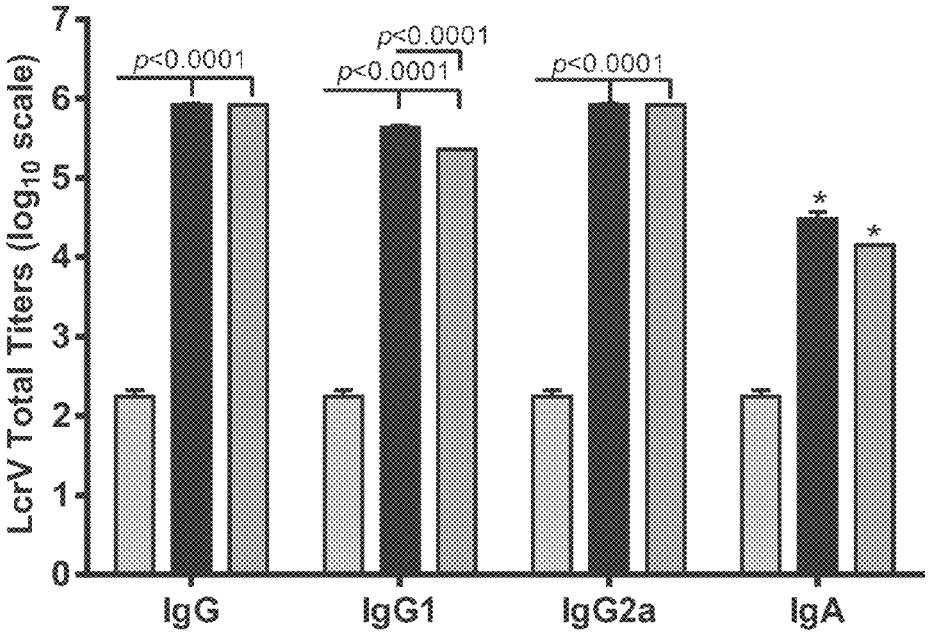
Figure 7C:
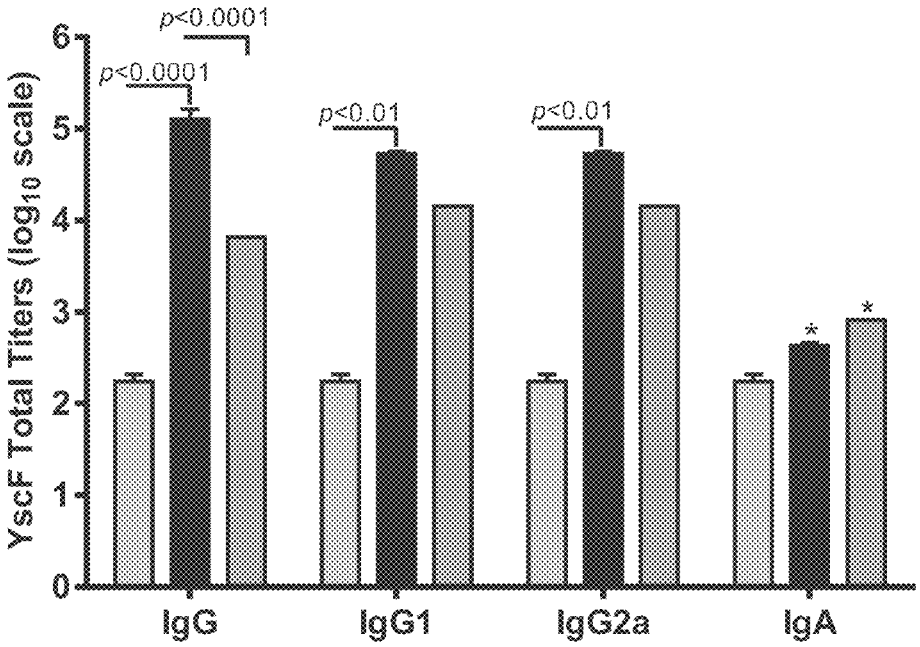

In terms of antibody production, we noted that IgG, its isotypes, and IgA antibody titers to the three antigens (F1, LcrV, and YscF) were generally higher in the prime-boost group of mice over those animals that only received the rAd5-YFV trivalent vaccine. Further, a balanced Th1 and Th2-based antibody responses were observed (FIG. 7A-7C).

Continued protection of mice conferred by prime-boost vaccination strategy against the initial aerosol and then the subsequent intranasal WT CO92 challenge. In our subsequent experiment, preAd-mice were vaccinated with either the rAd5-YFV trivalent vaccine alone or with a rYFV boost. The preAd-mice receiving the Ad5 empty vector alone served as a control. After the vaccination regimen, mice were subjected to WT CO92 aerosol challenge with still a relatively lower Dp ($3.14\times10^5$ CFU, ~150 $LD_{50}$) as compared to the above two aerosol challenges (FIGS. 5 and 6A). As noted in FIG. 8A, 100% of the animals survived the initial challenge in all of the immunized groups, while 90% of the control mice died (FIG. 8A). After 32 days of the initial aerosol challenge, the survivals from the immunized groups were re-challenged with 100 $LD_{50}$ of WT CO92 luc2 strain by the i.n. route, and the age-matched uninfected naïve mice (n=5) served as a control. As shown in FIG. 8A, 80% of the mice were protected from developing plague in the rAd5-YFV-immunized group, while this protection was 100% when the prime-boost strategy was used. In contrast, all of the naïve re-challenge control mice succumbed to infection within day 4 p.i. The bioluminescent images showed that the plague bacilli disseminated from the initial infection site of lungs to the whole body in all 5 naïve control mice after day 3 p.i. (FIG. 8B-I). On the other hand, no animals were positive in the group that received vaccination by the prime-boost regimen (FIG. 8B-II). However, one mouse from the rAd5-YFV-immunized group was bioluminescent positive, with the organisms confined in the lungs (FIG. 8B-III). This bioluminescent-positive animal along with another one mouse in the same group, which did not show bioluminescence at the time of imaging (day 3 p.i.), eventually died, resulting in the overall survival rate of 80% in the rAd5-YFV immunized group of mice (FIG. 8A).

Figure 9:
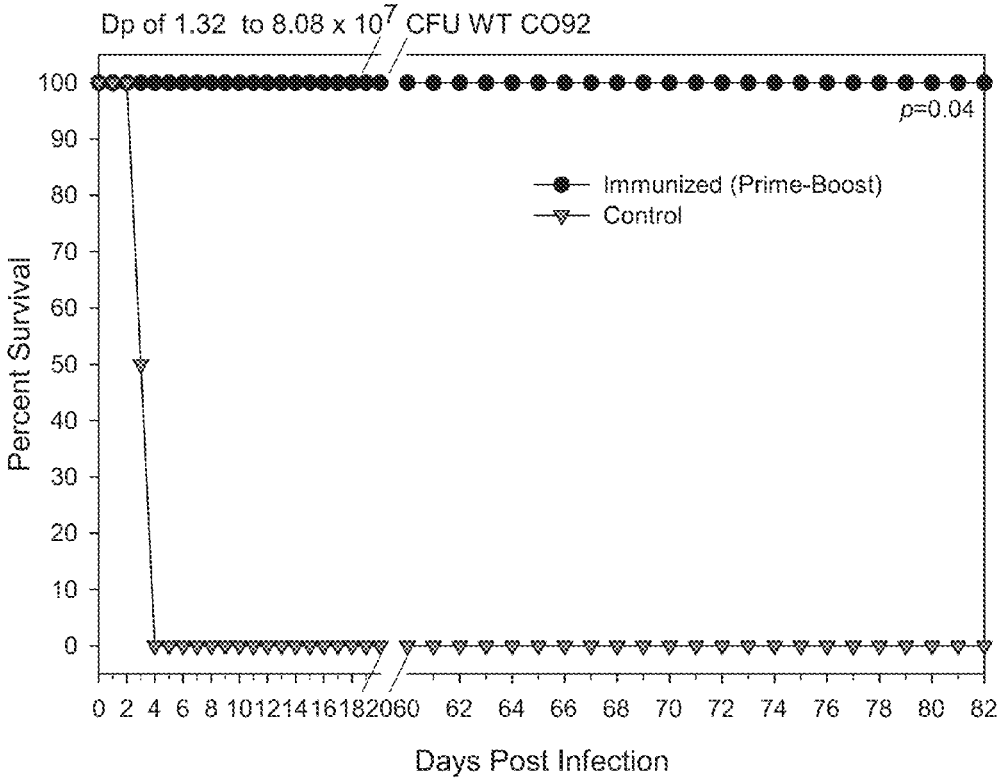
FIG. 9 shows the rAd5-YFV vaccine in combination with rYFV provided protection to NHPs with pre-existing adenovirus immunity against lethal aerosol challenge of WT CO92. To induce pre-existing adenovirus immunity, four NHPs were injected in the quadriceps muscle with $5\times10^{10}$ v.p. of Ad5-Empty (day 0). On day 30, these NHPs were immunized by the intranasal route with $1\times10^{11}$ v.p. of rAd5-YFV, followed by 50 μg of rYFV boost (emulsified 1:1 in Alum adjuvant) via the i.m. route on day 42. Another four NHPs received saline only (without immunization) and served as a control. On day 85, the NHPs were challenged with WT CO92 by the aerosol route with a Dp ranging from 1.32 to $8.08\times10^7$ CFU. The animals were euthanized when reached a clinical score ≥8 or at the termination of the experiment, and percentage of survival was plotted. The P values were in comparison to the NHP control group and are based on Kaplan-Meier Curve Analysis.
Figure 10A:
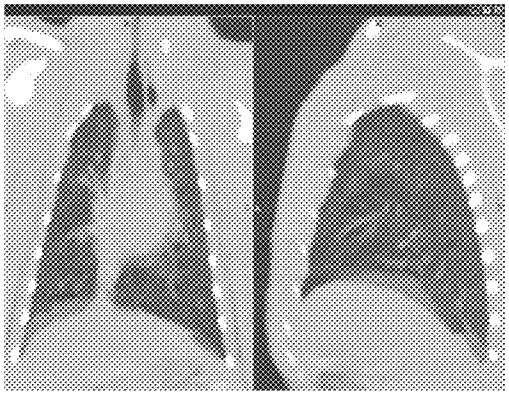
FIG. 10A-10C shows CT scans. NHPs were subjected to CT scan on day 42 (naïve and vaccinated) (FIG. 10A) and on day 88 (3 days post WT CO92 challenge) for the control NHPs (FIG. 10B) or day 167 (82 days post WT CO92 challenge) (FIG. 10C) for the immunized ones. The coronal and sagittal images of the lungs and their surrounding areas from representing NHPs were shown with the resolution of 512×512 pixels. The image sharpness was optimized to soft tissue. The arrows indicated consolidation patches in the lungs of a representative infected control NHP.
Figure 10B:
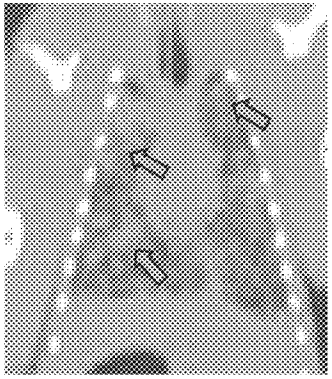
Figure 10C:
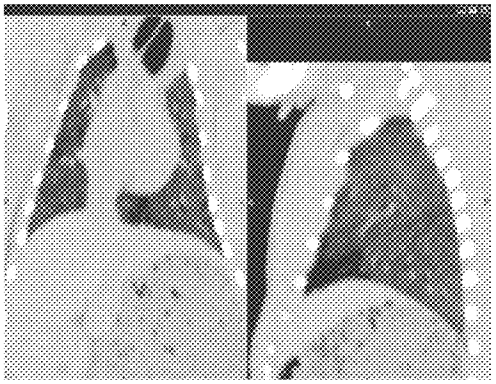

Evaluation of protection provided by the trivalent rAd5-YFV vaccine in cynomolgus macaques against aerosol challenge of WT CO92. Four NHPs were initially i.m. injected with Ad5-empty to generate pre-existing adenoviral immunity. This was followed by one dose of the rAd5-YFV by the i.n. instillation in the form of mist, and then one dose of the rYFV by the i.m. route. Four unimmunized NHPs served as a control (Table 1). These NHPs were then challenged with the aerosolized WT CO92 at Dp ranging from 1.32 to $8.08\times10^7$ CFU (~13,200-80,800 $LD_{90}$, with 1 $LD_{90}$=864 CFU (37)). No clinic signs were noted in the immunized group of NHPs, and the animals remained healthy and survived the WT CO92 challenge until euthanized at the end of the study (FIG. 9). The CT scans of immunized NHPs, that survived the WT CO92 challenge (FIG. 9) and euthanized on day 82 post challenge, did not display any abnormalities in the lungs and their surrounding areas when compared to the images of the animals before the WT CO92 challenge on day 85 (FIG. 10) (Table 1). In contrast, the control NHPs euthanized on day 3-to-4 post challenge, showed consolidation in both the right and the left lung, an indication of severe inflammation (FIG. 10).

Necropsy on immunized NHPs was performed 82 days after the WT CO92 challenge, and no gross abnormities were observed, and the internal organs (lungs, liver, spleen and the lymph nodes) were all free of bacteria (Table 2). In contrast, all unimmunized control NHPs developed clinical signs of the disease as early as 36 h p.i. and reached a clinical score of 8 and higher on day 3-to-4 p.i. The control NHPs had cough, abnormal respiration, lethargy, and a hunched posture. Although we did not notice fever in these animals during the progression of the disease, it could be related to not continuously monitoring these NHPs by using telemetry. Necropsy of these animals revealed serous hemorrhagic fluid in the thorax with respiratory frothy serous discharge. Lungs were hyper-inflated with hemorrhagic frothy fluid, and the spleen, liver and the lymph nodes were enlarged. The highest bacterial loads (1.12 to $1.26\times10^9$ CFU/node) were noted in the hilar lymph nodes and lungs ($2.22\times10^7$ to $1.06\times10^9$ CFU/g) followed by the liver ($8.16\times10^6$ to $1.69\times10^7$ CFU/g), spleen (2.13 to $4.47\times10^6$ CFU/g) and submandibular lymph nodes ($2.33\times10^5$ CFU/node). Only one animal showed bacteria in the blood with a count of 2500 CFU/ml, and no bacilli was detected in the other control NHPs (Table 2).

TABLE 2

NHP clinical score, bacterial loads and necropsy report

| NHP | Days Post Infection | Bacterial loads in blood/organs | Clinical Score | Necropsy Report |
|---|---|---|---|---|
| Control | 3-4 | Blood: 0-2500 CFU/ml<br>Lung: $2.22 \times 10^7$-$1.06 \times 10^9$ CFU/g<br>Liver: $8.16 \times 10^6$-$1.69 \times 10^7$ CFU/g<br>Spleen: 2.13-$4.47 \times 10^6$ CFU/g<br>Hilar lymph node: 1.12-$1.26 \times 10^9$ CFU/node<br>Submandibular lymph node: 2.0-$2.33 \times 10^5$ CFU/node | ≥8 | External: Thin, pale, dehydrated and scruffy coat<br>Respiratory: Frothy serous discharge; hyper-inflated with hemorrhagic frothy fluid (~50 mL)<br>Lymphatic: Enlarged submandibular node<br>Spleen: Firm and enlarged<br>Liver: Firm, enlarged and rounded edges<br>Locomotion: Lethargic<br>Body Cavities: Serous hemorrhagic fluid in thorax (~50 mL) |
| Immunized | 82 | Negative for all the organs; blood samples were negative for bacteria as early as day 3 post infection | 0 | Normal |

Figure 11A:
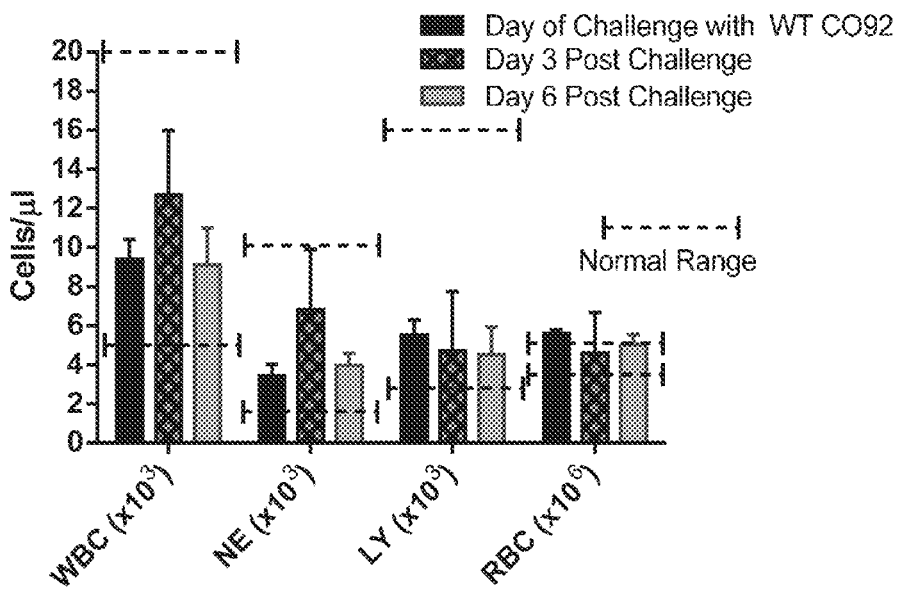
FIG. 11A-11B shows hematologic analysis. Blood samples of immunized (FIG. 11A) and unimmunized control (FIG. 11B) NHPs were collected from the femoral veins and analyzed on the day of challenge with WT CO92 and on days 3 and 6 post challenge (days 88 and 91 post immunization and challenge) by using a Drew Scientific Hemavet 950 hematology system. WBC: white blood cells; NE: neutrophils; LY: lymphocytes. The arithmetic means±standard deviations of the cell counts/μl were plotted. The dotted lines indicated the physiological ranges for each of the corresponding parameters measured.
Figure 11B:
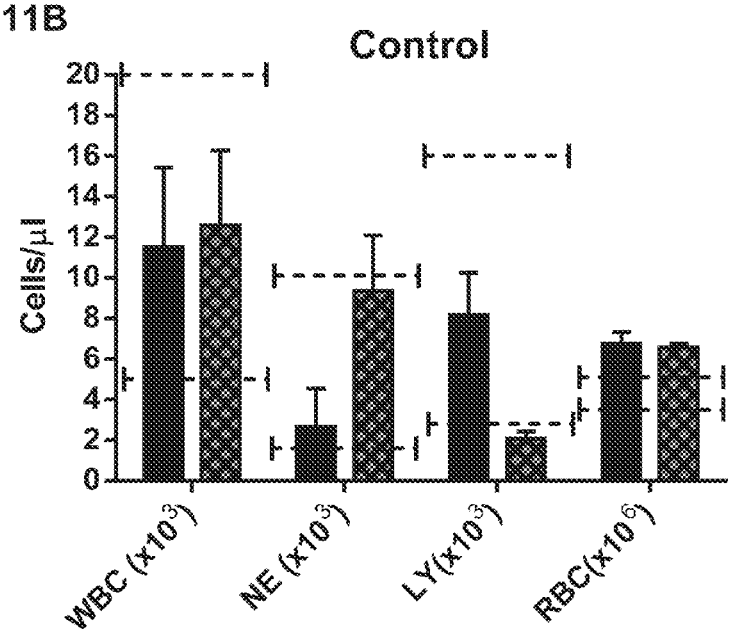

NHP blood cell counts and antibody titers. The changes in the blood cell counts in immunized NHPs versus the control after WT CO92 challenge are shown in FIG. 11. Only the lymphocyte (LY) counts in the control NHPs fell below the normal range by day 3 post WT CO92 challenge before they were euthanized. However, in the immunized NHPs, LY counts remained within the normal range on days 3 and 6 post WT CO92 challenge.

Figure 12A:
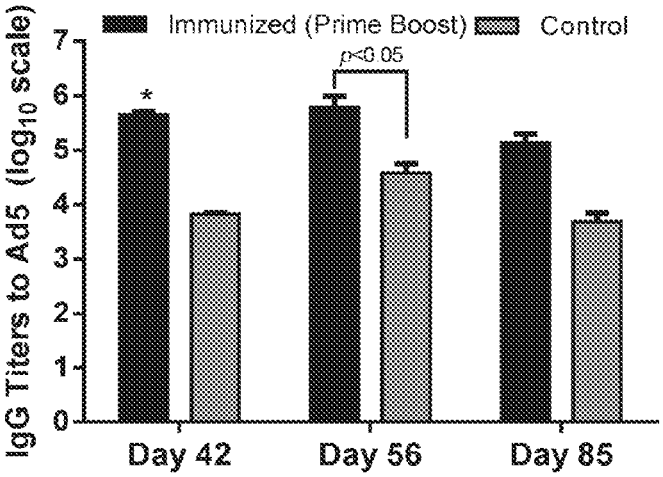
FIG. 12A-12E shows antibody responses in NHPs immunized with the rAd5-YFV vaccine in combination of rYFV. Four randomly selected NHPs were injected in the quadriceps muscle with $5\times10^{10}$ v.p. of Ad5-Empty to induce pre-existing immunity (day 0). On day 30, these NHPs were immunized by the intranasal route with $1\times10^{11}$ v.p. of rAd5-YFV, followed by 50 μg of rYFV boost (emulsified 1:1 in Alum adjuvant) via the i.m. route on day 42. Another four NHPs received saline only (without immunization) and served as a control. On day 85, the NHPs were challenged with WT CO92 by the aerosol route. Blood samples were collected from the femoral veins of NHPs at various time points during the experiment. The total IgG titers to Ad5 (FIG. 12A), F1 (FIG. 12B), LcrV (FIG. 12C), and YscF (FIG. 12D) as well as IgA titers to LcrV (FIG. 12E) on days 42, 56, and 85 were evaluated by ELISA. The P values were in comparison to the indicated groups and were based on Two-way ANOVA with the Tukey's post hoc correction. The asterisks indicated statistical significance compared to the control (Ad5-Empty) mice by using multiple Student's t-test with the Holm-sidak post hoc test correction.
Figure 12B:
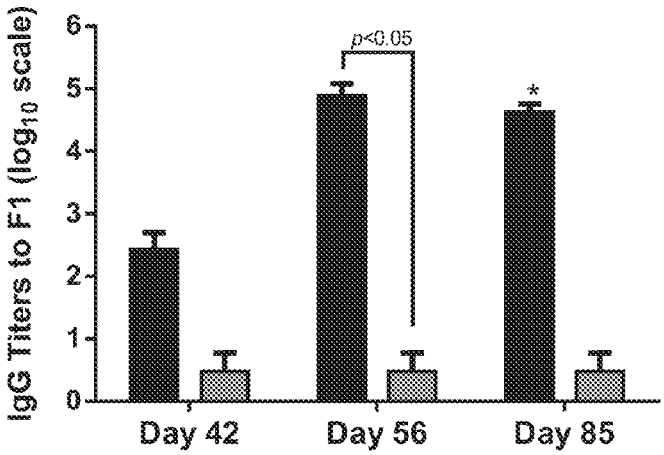
Figure 12C:
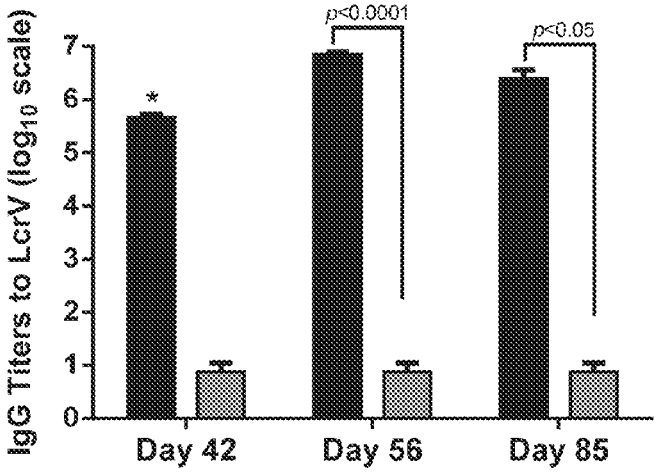
Figure 12D:
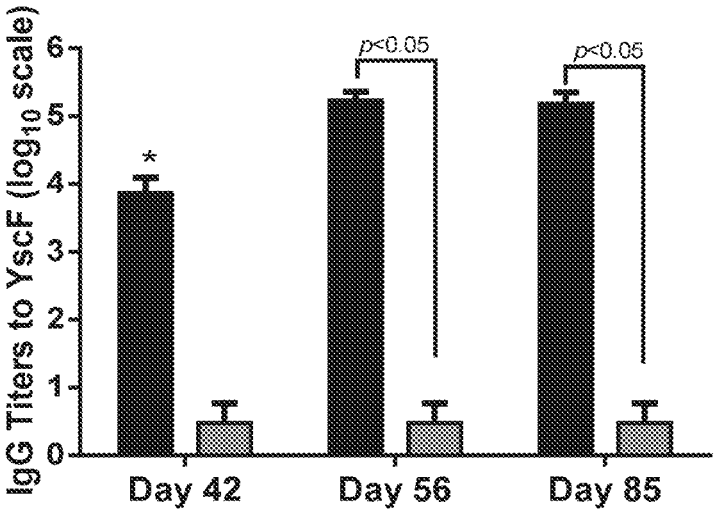
Figure 12E:
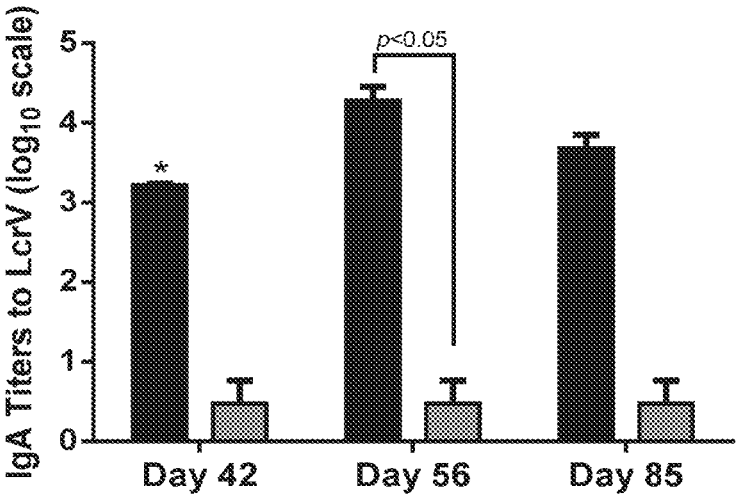
Figure 13A:
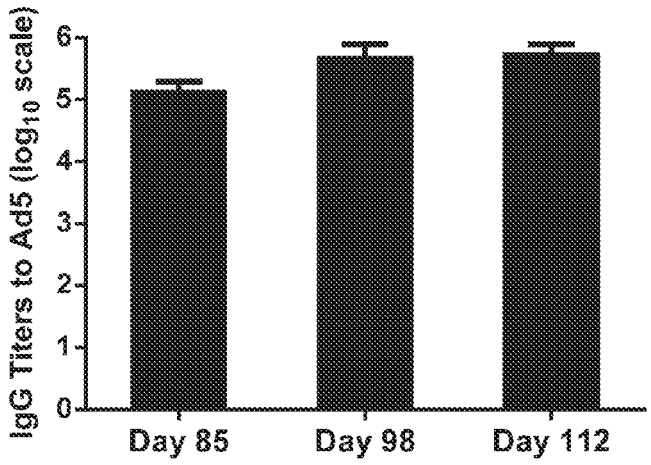
FIG. 13A-13E shows antibody responses of vaccinated NHPs after WT CO92 aerosol challenge. Four randomly selected NHPs were injected in the quadriceps muscle with $5\times10^{10}$ v.p. of Ad5-Empty to induce pre-existing immunity (day 0). On day 30, these NHPs were immunized by the intranasal route with $1\times10^{11}$ v.p. of rAd5-YFV, followed by 50 μg of rYFV boost (emulsified 1:1 in Alum adjuvant) via the i.m. route on day 42. Another four NHPs received saline only (without immunization) and served as a control. On day 85, the NHPs were challenged with WT CO92 by the aerosol route. Blood samples were collected from the femoral veins of NHPs at various time points during the experiment from the immunized NHPs. The total IgG titers to Ad5 (FIG. 13A), F1 (FIG. 13B), LcrV (FIG. 13C), and YscF (FIG. 13D) as well as total IgA titers to LcrV (FIG. 13E) on days 85, 98 and 112 were evaluated by ELISA. Days 98 and 112 represented 14 and 28 days post WT CO92 challenge after immunization.
Figure 13B:
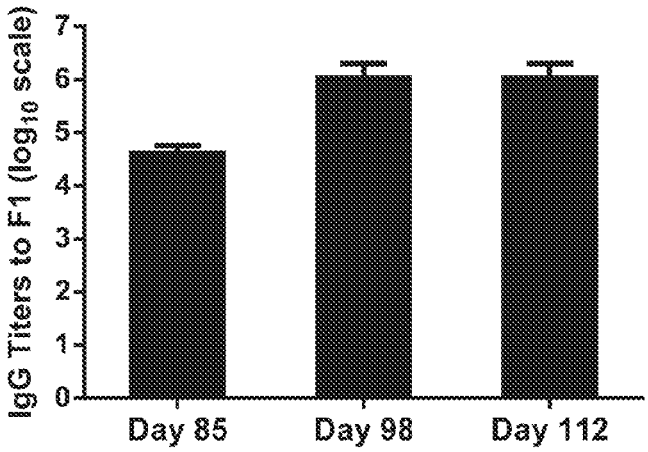
Figure 13C:
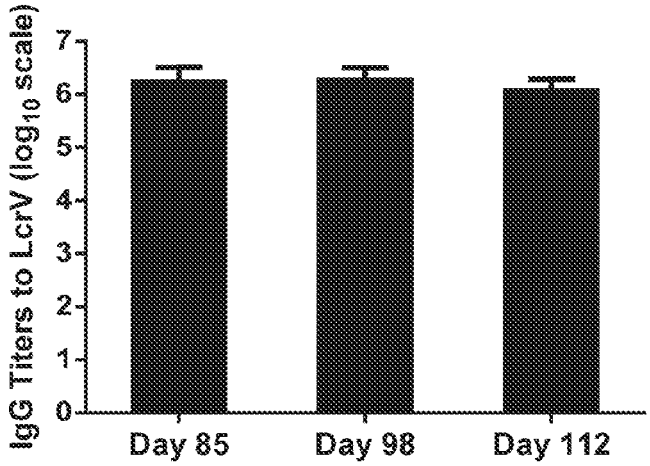
Figure 13D:
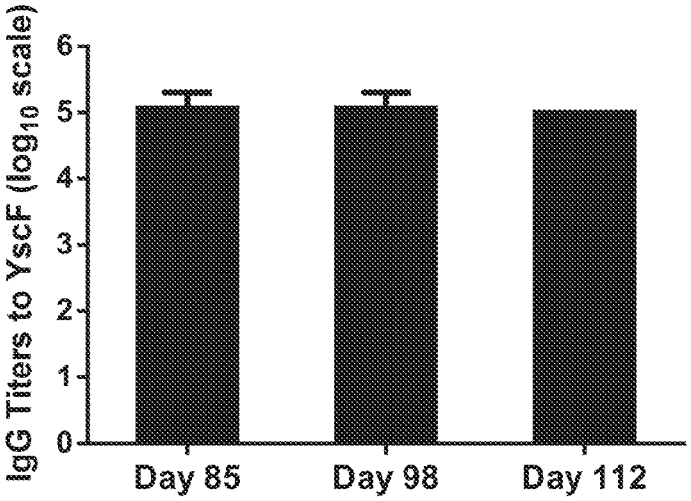
Figure 13E:
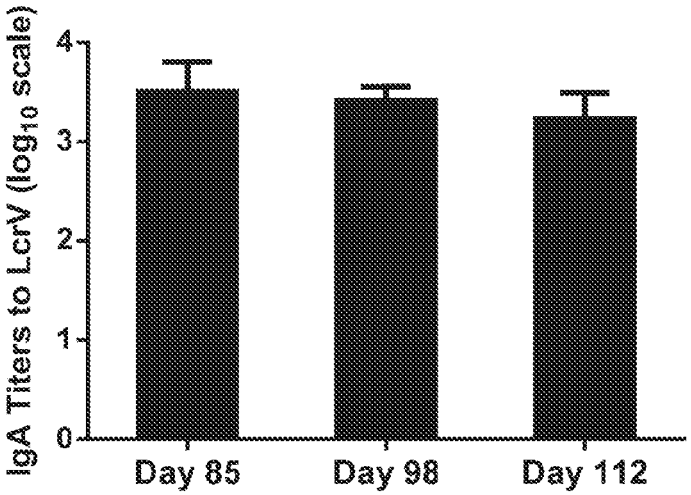

Both immunized and control NHPs showed some level of pre-existing Ad5 antibody titers (6,400-25,600) on day 0 as a consequence of naturally acquired infection with adenoviruses. The anti-Ad5 titer was increased to 409,600 on day 30 in immunized NHPs after receiving the rAd5-Empty injection, and continued to climb up slightly on days 42 and 56 as a result of immunization with rAd5. The anti-Ad5 antibody titer was maintained at a similar level to that observed on day 0 in the control NHPs (FIG. 12A). No pre-existing anti-LcrV, anti-F1, and anti-YscF antibodies were detected in both the groups of NHPs before immunization (data not shown). However, high antibody titers to three Y. pestis-specific antigens (e.g., F1, LcrV, and YscF) were noticed in all of the immunized NHPs (FIG. 12B-12E). Compared to the antibody titers on day 42, the antigen specific IgG antibodies increased ~10 fold for LcrV and YscF, but nearly 1000 fold for F1 on day 56 (FIG. 12B-12D). Thus, boost on day 30 with rYFV (Table 1) led to increase in antibody titers. These antigen-specific antibody titers slightly decreased on day 85 (the day of challenge). A similar trend was observed for the anti-LcrV IgA antibody titers, which were increased ~10 fold on day 56 after the rYFV boost (FIG. 12E). Compared to all three antigen-specific IgG antibody titers, the anti-LcrV titers were the highest followed by anti-YscF and anti-F1 across the course of immunization, and the difference could reach up to 1000 fold (anti-LcrV vs anti-F1 on day 42) (FIGS. 12B and 12C). After WT CO92 aerosol challenge, anti-F1 IgG titers were further boosted, while sustaining IgG titers for LcrV and YscF, and IgA LcrV titers up to 28 days post WT CO92 challenge (overall day 112 after initiation of vaccination) (FIG. 13A-13E).

Figure 14:
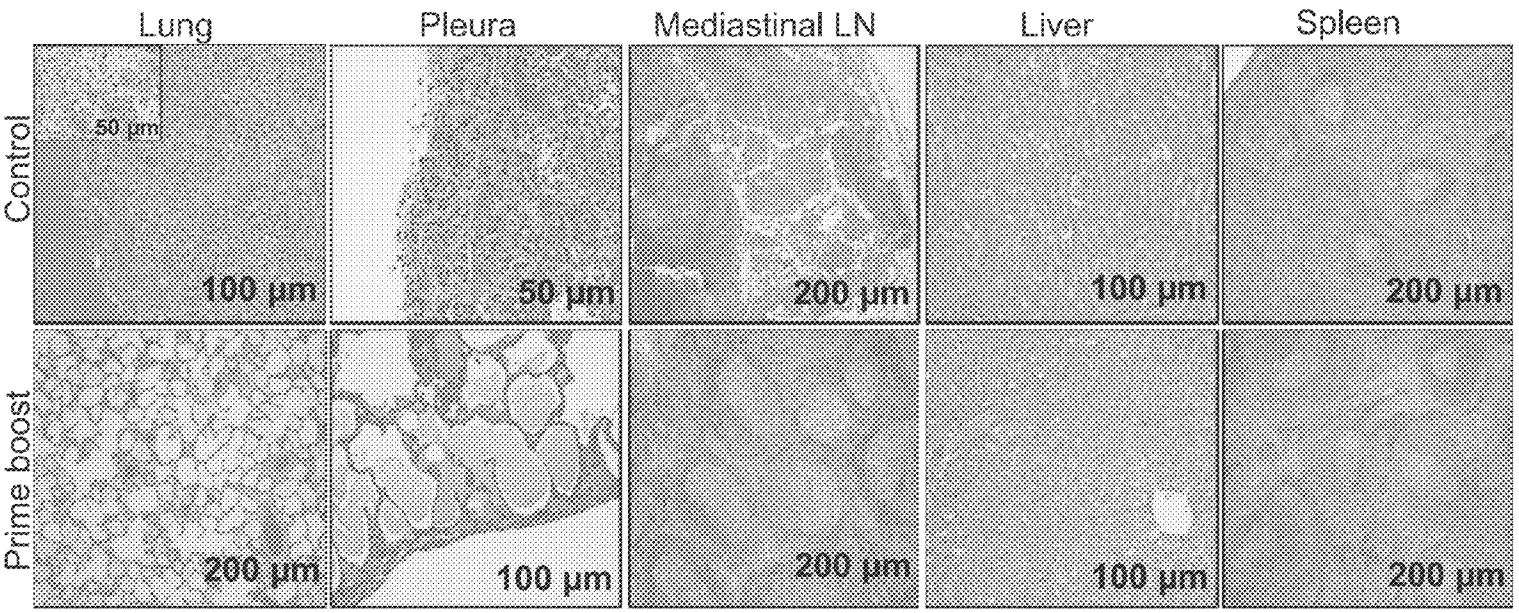
FIG. 14 shows histopathological analysis of tissues collected from NHP after WT CO92 aerosol challenge. Lungs, pleura, mediastinal lymph nodes, liver and the spleen tissues were collected from the control (3 or 4 day post WT CO92 challenge) and immunized NHPs (82 days post WT CO92 challenge) after euthanization and processed for histopathological analysis. The inset from lungs revealed the presence of coccobacilli, presumptively Y. pestis, by Gram staining. The magnification of each image is indicated.

NHP histopathological analysis. As shown in FIG. 14, the unimmunized control NHPs showed marked acute inflammatory reactions in the lungs, pleura, and the mediastinal lymph nodes. Specifically, multifocal hemorrhage and diffused supportive inflammation were observed in the lungs with no alveolar spaces. Similar changes were also observed in pleura and mediastinal lymph nodes of these unimmunized NHPs. Furthermore, tissue sections from the lungs with Gram staining revealed the presence of bacteria, presumptively Y. pestis (FIG. 14, inset). Interestingly, the liver and the spleen tissues of unimmunized NHPs showed normal morphological characteristics in spite of higher bacterial loads (Table 2), indicating that pneumonic changes are the primary cause of death in control groups. In the immunized NHP group, the lungs, pleura, mediastinal lymph nodes, and the liver were normal, and the lungs had alveolar spaces. The only notable and expected changes observed in the prime-boost group was the hyperplasia of lymphoid follicles in mediastinal lymph nodes and the spleen. These changes can mainly be attributed to reaction of vaccination.

DISCUSSION

Historically, vaccination has not only been one of the most significant advances in healthcare, but also a cost-effective means of public health intervention. The high mortality rate associated with pneumonic plague, the potential use of Y. pestis as a biological weapon, and the current lack of a FDA approved plague vaccine highlight the importance of our studies.

Previously, the plague vaccine licensed in the U.S. (sold under the name of USP) was a formaldehyde-killed preparation of the highly virulent 195/P strain of Y. pestis; however, the production of this vaccine was discontinued in 1999. The vaccination regimen included a course of injections over a period of 6 months, and then the annual boosters (38, 39). The vaccine was effective against bubonic plague, but protection against pneumonic plague was uncertain. The incidence of side effects, such as malaise, headaches, elevated body temperature, and lymphadenopathy was high; and the vaccine was expensive (40). A live-attenuated vaccine based on Y. pestis pigmentation locus negative EV76 strains is also available in some parts of the world where plague is endemic (1). These types of vaccines have existed since the first half of the $20^{th}$ century and have proven effective against both subcutaneous and inhalation challenges with Y. pestis. However, the EV76-based vaccines are not genetically uniform and are also highly reactogenic (41), and, hence, would not meet the standards for FDA approval.

The major problems encountered in developing live-attenuated vaccines are inadequate attenuation, particularly in immunocompromised individuals, and the potential to revert back to the virulent phenotype. Efforts have been made to generate well-characterized and rationally-designed attenuated plague vaccines. For example, mutations that effectively attenuate Salmonella such as aroA, phoP, htrA and lpp genes, were introduced in Y. pestis, but these mutations had only a limited effect on Y. pestis virulence (33, 42-44). Similarly, a deletion of the Y. pestis global regulator gene rovA, significantly attenuated the bacterium during subcutaneous infection, but this mutant was only slightly attenuated when given via an intranasal or the intraperitoneal route (45). Recently, a highly attenuated Δlpp ΔmsbB Δail triple mutant, which was deleted for genes encoding Braun lipoprotein (Lpp), an acetyltransferase (MsbB), and the Attachment Invasion Locus (Ail), was constructed (27). Mice immunized with this triple mutant via either the intranasal, subcutaneous, or the intramuscular route, were protected from lethal WT CO92 challenge, and thus could be an excellent vaccine candidate (27, 35). This triple mutant was subsequently excluded from the CDC select agent list in May 2016. However, further evaluation of the efficacy of this triple mutant in higher animal models is warranted.

While the above conventional vaccine strategies have focused on live-attenuated or killed bacterial approaches, a new method in the development of vaccines uses platform technologies to overcome some of the challenges in vaccine design. The adenoviral vector system has been successfully used as a vaccine platform for a number of pathogens, including Y. pestis (46, 47), with several advantages: 1) the adenoviral genome is well characterized with the capability of integrating ≥6-kb of the potential insert size for delivering multiple antigens; 2) the replication-defective Ad5 vector has been developed for gene therapeutic applications at a wide range of doses, with minimal side effects; and 3) adenoviruses have a broad tropism infecting a variety of dividing and non-dividing cells. Studies have shown that adenoviruses transfer genes effectively to APCs in vivo to promote rapid and robust humoral and cellular immune responses to the transgene products (48-55). In addition, adenoviruses can be grown to high titers in tissue culture cells and can be applied systemically as well as through mucosal surfaces, and are relative thermostable to facilitate their clinical use.

Our rAd5-YFV trivalent vaccine had an average yield of $1\times10^{16}$ v.p. per batch in a cell suspension culture in CD 293 Medium. The vaccine was free of proteins, serum, and animal-derived components, thus making it suitable for a broad range of prophylactic and therapeutic use. Compared to a favored Th2 response in mice immunized with rYFV or a mixture of rYscF, rLcrV, and rF1 (given with alum which skews the immune response to Th2) (FIG. 2A), a more balanced Th1- and Th2-based antibody response was observed in mice immunized with the rAd5 vaccines (FIGS. 3C, 4C, and 7A-7C). Indeed, Ad5 has been shown to promote Th1 response (47). As expected, intranasal administration of rAd5-LcrV monovalent and rAd5-YFV trivalent vaccines elicited IgA production in immunized animals (both mice and NHPs), and most importantly, mice immunized with rAd5-YFV alone or in a prime-boost vaccination strategy, exhibited a robust T cell proliferative responses (FIG. 6C). These features suggest superiority of Ad5-based vaccines over the rF1-V-based subunit vaccines, as the protection of the latter vaccines is largely dependent on systemic antibody responses without mucosal and cellular immune components. Interestingly, although generally a higher IgG antibody titer was observed across all mice immunized intranasally when compared to animals immunized intramuscularly with the recombinant adenoviruses, the protection rate was indistinguishable during the development of bubonic plague. However, subtle differences in protection were noted depending upon of the route of immunization of mice in a pneumonic plague model (FIGS. 3A and 3B), which further highlighted the importance of mucosal immunity during the development of pneumonic plague.

Pneumonic plague begins with an anti-inflammatory state (i.e., first 24 to 36 h after infection), which is characterized by a delay in the inflammatory cell recruitment to the lungs and production of pro-inflammatory cytokines and chemokines (56). Therefore, a plague vaccine should be able to stimulate a strong mucosal immunity to overcome this initial immune suppression in the host (57). In our future studies, we plan to discern the role of mucosal immune response (e.g., IgA) that is triggered by the rAd5-YFV vaccine in protection.

Compared to the monovalent rAd5-LcrV vaccine, the trivalent rAd5-YFV vaccine not only mounted higher anti-LcrV antibody titers (both IgG and IgA) (FIGS. 3C and 4C) but also generated immune responses to the F1 and YscF (FIG. 7), which correlated with better protection of animals against both bubonic and pneumonic plague (FIGS. 3A and 3B, 4A and 4B, and 5). In addition, LcrV was more immunogenic than F1 and YscF in both mice and NHPs that were immunized with the trivalent rAd5-YFV vaccine (FIGS. 7 and 12). In contrast, the antibody titers to F1 were the lowest among the three examined antigens in the rAd5-YFV-immunized NHPs (FIG. 12). The difference in immunogenicity may be attributed to the nature of each of the antigens; however, conformation of the antigens in the fusion protein may also play a role, especially as higher anti-LcrV antibody titers were observed in the rAd5-YFV-immunized mice than in rAd5-LcrV vaccinated animals. Alternatively, the presence of other two antigens could augment antibody production to LcrV.

Previously, a rAd5 (designated as rAdsecV) expressing a human Igk secretion (sec) signal fused to 1crV was reported (46). The rAdsecV produced a secreted form of LcrV and elicited specific T cell responses as well as high IgG titers in sera, which protected mice from a lethal intranasal challenge 40 of Y. pestis CO92 in a single intramuscular immunization (46). Although there is no direct comparison, the AdsecV provided better protection (80-100%) in mice than our monovalent rAd5-LcrV vaccine (~20%) (FIGS. 3B and 4B), indicating that the secreted form of LcrV might be more immunogenic in mice. However, different species of mice (Swiss-Webster versus BALB/c) and challenge doses were used in these studies (46). In our initial study, a rAd5 expressing the Igk secretion signal fused to YFV was successfully created; however, we found that the secreted YFV (sYFV) was toxic to HEK 293 cells, which prevented large-scale expansion of this construct (data not shown).

There are several established plague models using NHPs, such as the langur monkey (58), African green vervets (59, 60), baboons (61, 62), and rhesus macaque (63, 64). However, the current recommendations from FDA and the National Institute of Allergy and Infectious Disease to support plague therapeutic and vaccine studies is a cynomolgus macaque (Macaca fascicularies) (CM) pneumonic plague model (65). In addition, the lethal dose of Y. pestis has been established for aerosol challenge of CMs with the standard CO92 strain, and this model was utilized in protection studies including F1-V-based subunit vaccines for the past several years as well as in most recent studies (65-72). Importantly, CMs exhibit a clinical course of the disease similar to that described in humans (73).

Indeed, we observed the unimmunized NHPs after WT CO92 aerosol challenge had cough, respiratory changes, lethargy, and hunched posture, as well as typical pneumonic lesions in the lungs (FIG. 14). However, no fever was observed during the course of infection. This is in contrast to the most recent report that the onset of fever was predominant across all CMs infected with Y. pestis (72). This highlights the importance of using telemetry to observe physiological parameters in a real-time manner. Our study did not employ telemetry, while the other report measured body temperature in real time and the temperature of 1.5° C. above the baseline was considered fever (72). One notable finding of our study was that a significant increase in the antibody titer was noted in immunized NHPs, especially to F1, after rYFV boost as well as after WT CO92 challenge (FIG. 12 and FIG. 13). These data indicated memory B cell evoked recall responses. Similarly, a predominant hyperplasia of lymphoid follicles was observed in the immunized NHPs in mediastinal lymph nodes and spleen for as long as 82 days after the WT CO92 challenge (FIG. 14), suggesting a sustained immune response was developed in these NHPs, which could be pivotal in long-term protection of animals against plague. Our studies also indicated that by using the prime-boost strategy in CMs, higher antibody responses were generated compared to animals that were immunized with only rAd5-YFV (FIG. 12). An average antibody titers of ~$1.7\times10^6$ for LcrV, ~$4.3\times10^4$ for F1 and ~$1.2\times10^5$ for YscF, were mounted when animals were immunized following the prime-boost strategy. These antibodies titers were sufficient for providing complete protection to CMs against high aerosol challenge doses of Y. pestis CO92, although the role of cell-mediated immunity in protection should also be considered.

One of the major concerns of adenoviral vectors for vaccine development is the pre-existing immunity to Ad5 (in ~95% of the human population) that could lessen the efficacy of the vaccine. Currently, most of the efforts to overcome the concerns regarding neutralizing antibodies have been focused on identifying alternative serotypes of adenovirus (74, 75). While some groups have reported favorable results with this approach, it offers only a short-term solution, as new adenoviral vector adaptation will result in the generation of neutralizing antibodies through widespread use. On the other hand, a number of studies indicated that administration of Ad5-vectored vaccines via the i.n. route might overcome pre-existing immunity against the Ad5 vector (76-79). We did observe slightly lower Y. pestis antigen-specific antibody titers in mice with the pre-existing adenoviral immunity than those animals without the pre-existing adenoviral immunity when mice were i.n.-immunized with either the rAd5-LcrV or the rAd5-YFV vaccine (FIG. 4C). However, the protection conferred in mice against Y. pestis challenge was similar in both groups of mice irrespective of the pre-existing adenoviral immunity (FIGS. 4A and 4B). Most importantly, NHPs with pre-existing adenoviral immunity and immunized with the rAd5-YFV vaccine, plus a boost of rYFV, were fully protected from a high aerosol challenge dose of WT CO92 (FIG. 9).

In addition to YscF, other Y. pestis antigens such as the T3SS components YpkA, YopH, YopE, YopK, YopN, as well as a subunit of pH 6 antigen and purified LPS were studied for their immunogenic efficacies against plague infection, but did not generate promising results (80). The only protection was observed in mice vaccinated with YopD, a protein involved in the delivery of T3 SS effectors into the host cell (81). However, YopD-vaccination provided protection only against the non-encapsulated bacilli but not against the encapsulated Y. pestis CO92 strain.

As the most promising plague subunit vaccines currently under development are primarily dependent on only two antigens F1 and LcrV, the incorporation of a new antigen YscF may help in formulating a better vaccine against all human plague causing-strains as we showed using the bacteriophage T4-based platform (82). Furthermore, the adenoviral vector has been demonstrated to have adjuvant activities as well as the ability to promote cellular immunity (51, 83, 84). In this regard, our trivalent rAd5-YFV vaccine has unique advantages as a plague vaccine. Our further studies will include in depth characterization of cell-mediated immune responses in vaccinated CMs.

CITATIONS

1. Smiley S T. 2008. Current challenges in the development of vaccines for pneumonic plague. Expert Rev Vaccines 7:209-221.
2. Sun W, Roland K L, Curtiss R, 3rd. 2011. Developing live vaccines against plague. J Infect Dev Ctries 5:614-627.
3. Perry R D, Fetherston J D. 1997. Yersinia pestis—etiologic agent of plague. Clin Microbiol Rev 10:35-66.
4. Cornelis G R. 2002. Yersinia type III secretion: send in the effectors. J Cell Biol 158:401-408.
5. Powell B S, Andrews G P, Enama J T, Jendrek S, Bolt C, Worsham P, Pullen J K, Ribot W, Hines H, Smith L, Heath D G, Adamovicz J J. 2005. Design and testing for a nontagged F1-V fusion protein as vaccine antigen against bubonic and pneumonic plague. Biotechnol Prog 21:1490-1510.
6. Alvarez M L, Pinyerd H L, Crisantes J D, Rigano M M, Pinkhasov J, Walmsley A M, Mason H S, Cardineau G A. 2006. Plant-made subunit vaccine against pneumonic and bubonic plague is orally immunogenic in mice. Vaccine 24:2477-2490.
7. Williamson E D, Flick-Smith H C, Waters E, Miller J, Hodgson I, Le Butt C S, Hill J. 2007. Immunogenicity of the rF1+rV vaccine for plague with identification of potential immune correlates. Microb Pathog 42:11-21.
8. Cornelius C A, Quenee L E, Overheim K A, Koster F, Brasel T L, Elli D, Ciletti N A, Schneewind O. 2008. Immunization with recombinant V10 protects cynomolgus macaques from lethal pneumonic plague. Infect Immun 76:5588-5597.
9. Baker E E, Somer H, Foster L W, Meyer E, Meyer K F. 1952. Studies on immunization against plague. I. The isolation and characterization of the soluble antigen of Pasteurella pestis. J Immunol 68:131-145.
10. Rosenzweig J A, Jejelowo O, Sha J, Erova T E, Brackman S M, Kirtley M L, van Lier C J, Chopra A K. 2011. Progress on plague vaccine development. Appl Microbiol Biotechnol 91:265-286.
11. Quenee L E, Ciletti N, Berube B, Krausz T, Elli D, Hermanas T, Schneewind O. 2011. Plague in Guinea pigs and its prevention by subunit vaccines. Am J Pathol 178:1689-1700.
12. Quenee L E, Ciletti N A, Elli D, Hermanas T M, Schneewind O. 2011. Prevention of pneumonic plague in mice, rats, guinea pigs and non-human primates with clinical grade rV10, rV10-2 or F1-V vaccines. Vaccine 29:6572-6583.

13. Lin J S, Kummer L W, Szaba F M, Smiley S T. 2011. IL-17 contributes to cell-mediated defense against pulmonary Yersinia pestis infection. J Immunol 186:1675-1684.
14. Smiley S T. 2008. Immune defense against pneumonic plague. Immunol Rev 225:256-271.
15. Agar S L, Sha J, Foltz S M, Erova T E, Walberg K G, Baze W B, Suarez G, Peterson J W, Chopra A K. 2009. Characterization of the rat pneumonic plague model: infection kinetics following aerosolization of Yersinia pestis CO92. Microbes Infect 11:205-214.
16. Williamson E D, Packer P J, Waters E L, Simpson A J, Dyer D, Hartings J, Twenhafel N, Pitt M L. 2011. Recombinant (F1+V) vaccine protects cynomolgus macaques against pneumonic plague. Vaccine 29:4771-4777.
17. FDA. 2012. African Green monkey (Chlorocebus aethiops) animal model development to evaluate treatment of pneumonic plague.
18. Sha J, Endsley J J, Kirtley M L, Foltz S M, Huante M B, Erova T E, Kozlova E V, Popov V L, Yeager L A, Zudina I V, Motin V L, Peterson J W, DeBord K L, Chopra A K. 2011. Characterization of an F1 deletion mutant of Yersinia pestis CO92, pathogenic role of F1 antigen in bubonic and pneumonic plague, and evaluation of sensitivity and specificity of F1 antigen capture-based dipsticks. J Clin Microbiol 49:1708-1715.
19. Quenee L E, Cornelius C A, Ciletti N A, Elli D, Schneewind O. 2008. Yersinia pestis caf1 variants and the limits of plague vaccine protection. Infect Immun 76:2025-2036.
20. Anisimov A P, Dentovskaya S V, Panfertsev E A, Svetoch T E, Kopylov P, Segelke B W, Zemla A, Telepnev M V, Motin V L. 2010. Amino acid and structural variability of Yersinia pestis LcrV protein. Infect Genet Evol 10:137-145.
21. Motin V L, Pokrovskaya M S, Telepnev M V, Kutyrev V V, Vidyaeva N A, Filippov A A, Smirnov G B. 1992. The difference in the lcrV sequences between Y. pestis and Y. pseudotuberculosis and its application for characterization of Y. pseudotuberculosis strains. Microb Pathog 12:165-175.
22. Matson J S, Durick K A, Bradley D S, Nilles M L. 2005. Immunization of mice with YscF provides protection from Yersinia pestis infections. BMC Microbiol 5:38.
23. Swietnicki W, Powell B S, Goodin J. 2005. Yersinia pestis Yop secretion protein F: purification, characterization, and protective efficacy against bubonic plague. Protein Expr Purif 42:166-172.
24. Lathem W W, Price P A, Miller V L, Goldman W E. 2007. A plasminogen-activating protease specifically controls the development of primary pneumonic plague. Science 315:509-513.
25. Doll J M, Zeitz P S, Ettestad P, Bucholtz A L, Davis T, Gage K. 1994. Cat-transmitted fatal pneumonic plague in a person who traveled from Colorado to Arizona. Am J Trop Med Hyg 51:109-114.
26. Sha J, Rosenzweig J A, Kirtley M L, van Lier C J, Fitts E C, Kozlova E V, Erova T E, Tiner B L, Chopra A K. 2013. A non-invasive in vivo imaging system to study dissemination of bioluminescent Yersinia pestis CO92 in a mouse model of pneumonic plague. Microb Pathog 55:39-50.
27. Tiner B L, Sha J, Kirtley M L, Erova T E, Popov V L, Baze W B, van Lier C J, Ponnusamy D, Andersson J A, Motin V L, Chauhan S, Chopra A K. 2015. Combinational deletion of three membrane protein-encoding genes highly attenuates Yersinia pestis while retaining immunogenicity in a mouse model of pneumonic plague. Infect Immun 83:1318-1338.
28. Agar S L, Sha J, Foltz S M, Erova T E, Walberg K G, Parham T E, Baze W B, Suarez G, Peterson J W, Chopra A K. 2008. Characterization of a mouse model of plague after aerosolization of Yersinia pestis CO92. Microbiology 154:1939-1948.
29. Suarez G, Sierra J C, Kirtley M L, Chopra A K. 2010. Role of Hcp, a type 6 secretion system effector, of Aeromonas hydrophila in modulating activation of host immune cells. Microbiology 156:3678-3688.
30. van Lier C J, Tiner B L, Chauhan S, Motin V L, Fitts E C, Huante M B, Endsley J J, Ponnusamy D, Sha J, Chopra A K. 2015. Further characterization of a highly attenuated Yersinia pestis CO92 mutant deleted for the genes encoding Braun lipoprotein and plasminogen activator protease in murine alveolar and primary human macrophages. Microb Pathog 80:27-38.
31. Sha J, Kirtley M L, van Lier C J, Wang S, Erova T E, Kozlova E V, Cao A, Cong Y, Fitts E C, Rosenzweig J A, Chopra A K. 2013. Deletion of the Braun lipoprotein-encoding gene and altering the function of lipopolysaccharide attenuate the plague bacterium. Infect Immun 81:815-828.
32. van Lier C J, Sha J, Kirtley M L, Cao A, Tiner B L, Erova T E, Cong Y, Kozlova E V, Popov V L, Baze W B, Chopra A K. 2014. Deletion of Braun lipoprotein and plasminogen-activating protease-encoding genes attenuates Yersinia pestis in mouse models of bubonic and pneumonic plague. Infect Immun 82:2485-2503.
33. Sha J, Agar S L, Baze W B, Olano J P, Fadl A A, Erova T E, Wang S, Foltz S M, Suarez G, Motin V L, Chauhan S, Klimpel G R, Peterson J W, Chopra A K. 2008. Braun lipoprotein (Lpp) contributes to virulence of yersiniae: potential role of Lpp in inducing bubonic and pneumonic plague. Infect Immun 76:1390-1409.
34. Guyton A C. 1947. Measurement of the respiratory volumes of laboratory animals. Am J Physiol 150:70-77.
35. Tiner B L, Sha J, Ponnusamy D, Baze W B, Fitts E C, Popov V L, van Lier C J, Erova T E, Chopra A K. 2015. Intramuscular immunization of mice with a live-attenuated triple mutant of Yersinia pestis CO92 induces robust humoral and cell-mediated immunity to completely protect animals against pneumonic plague. Clin Vaccine Immunol doi:10.1128/CVI.00499-15.
36. Agar S L, Sha J, Baze W B, Erova T E, Foltz S M, Suarez G, Wang S, Chopra A K. 2009. Deletion of Braun lipoprotein gene (lpp) and curing of plasmid pPCP1 dramatically alter the virulence of Yersinia pestis CO92 in a mouse model of pneumonic plague. Microbiology 155:3247-3259.
37. Warren R, Lockman H, Barnewall R, Krile R, Blanco O B, Vasconcelos D, Price J, House R V, Bolanowksi M A, Fellows P. 2011. Cynomolgus macaque model for pneumonic plague. Microb Pathog 50:12-22.
38. Russell P, Eley S M, Hibbs S E, Manchee R J, Stagg A J, Titball R W. 1995. A comparison of Plague vaccine, USP and EV76 vaccine induced protection against Yersinia pestis in a murine model. Vaccine 13:1551-1556.
39. Titball R W, Williamson E D. 2001. Vaccination against bubonic and pneumonic plague. Vaccine 19:4175-4184.
40. Titball R W, Williamson E D. 2004. Yersinia pestis (plague) vaccines. Expert Opin Biol Ther 4:965-973.

41. Cui Y, Yang X, Xiao X, Anisimov A P, Li D, Yan Y, Zhou D, Rajerison M, Carniel E, Achtman M, Yang R, Song Y. 2014. Genetic variations of live attenuated plague vaccine strains (Yersinia pestis EV76 lineage) during laboratory passages in different countries. Infect Genet Evol 26:172-179.
42. Oyston P C, Dorrell N, Williams K, Li S R, Green M, Titball R W, Wren B W. 2000. The response regulator PhoP is important for survival under conditions of macrophage-induced stress and virulence in Yersinia pestis. Infect Immun 68:3419-3425.
43. Oyston P C, Russell P, Williamson E D, Titball R W. 1996. An aroA mutant of Yersinia pestis is attenuated in guinea-pigs, but virulent in mice. Microbiology 142 (Pt 7):1847-1853.
44. Williams K, Oyston P C, Dorrell N, Li S, Titball R W, Wren B W. 2000. Investigation into the role of the serine protease HtrA in Yersinia pestis pathogenesis. FEMS Microbiol Lett 186:281-286.
45. Cathelyn J S, Crosby S D, Lathem W W, Goldman W E, Miller V L. 2006. RovA, a global regulator of Yersinia pestis, specifically required for bubonic plague. Proc Natl Acad Sci USA 103:13514-13519.
46. Chiuchiolo M J, Boyer J L, Krause A, Senina S, Hackett N R, Crystal R G. 2006. Protective immunity against respiratory tract challenge with Yersinia pestis in mice immunized with an adenovirus-based vaccine vector expressing V antigen. J Infect Dis 194:1249-1257.
47. Tatsis N, Ertl H C. 2004. Adenoviruses as vaccine vectors. Mol Ther 10:616-629.
48. Boyer J L, Kobinger G, Wilson J M, Crystal R G. 2005. Adenovirus-based genetic vaccines for biodefense. Hum Gene Ther 16:157-168.
49. Barouch D H, Nabel G J. 2005. Adenovirus vector-based vaccines for human immunodeficiency virus type 1. Hum Gene Ther 16:149-156.
50. Bessis N, GarciaCozar F J, Boissier M C. 2004. Immune responses to gene therapy vectors: influence on vector function and effector mechanisms. Gene Ther 11 Suppl 1:S10-17.
51. Molinier-Frenkel V, Lengagne R, Gaden F, Hong S S, Choppin J, Gahery-Segard H, Boulanger P, Guillet J G. 2002. Adenovirus hexon protein is a potent adjuvant for activation of a cellular immune response. J Virol 76:127-135.
52. Hackett N R, Kaminsky S M, Sondhi D, Crystal R G. 2000. Antivector and antitransgene host responses in gene therapy. Curr Opin Mol Ther 2:376-382.
53. Song W, Kong H L, Traktman P, Crystal R G. 1997. Cytotoxic T lymphocyte responses to proteins encoded by heterologous transgenes transferred in vivo by adenoviral vectors. Hum Gene Ther 8:1207-1217.
54. Wilson J M. 1996. Adenoviruses as gene-delivery vehicles. N Engl J Med 334:1185-1187.
55. Tripathy S K, Black H B, Goldwasser E, Leiden J M. 1996. Immune responses to transgene-encoded proteins limit the stability of gene expression after injection of replication-defective adenovirus vectors. Nat Med 2:545-550.
56. Lathem W W, Crosby S D, Miller V L, Goldman W E. 2005. Progression of primary pneumonic plague: a mouse model of infection, pathology, and bacterial transcriptional activity. Proc Natl Acad Sci USA 102:17786-17791.
57. Do Y, Didierlaurent A M, Ryu S, Koh H, Park C G, Park S, Perlin D S, Powell B S, Steinman R M. 2012. Induction of pulmonary mucosal immune responses with a protein vaccine targeted to the DEC-205/CD205 receptor. Vaccine 30:6359-6367.
58. Chen T H, Meyer K F. 1965. Susceptibility of the langur monkey (Semnopithecus entellus) to experimental plague: pathology and immunity. J Infect Dis 115:456-464.
59. Hallett A F, Isaacson M, Meyer K F. 1973. Pathogenicity and immunogenic efficacy of a live attentuated plaque vaccine in vervet monkeys. Infect Immun 8:876-881.
60. Chen T H, Elbert S S, Eisler D M. 1976. Immunity in plague: protection induced in Cercopithecus aethiops by oral administration of live, attenuated Yersinia pestis. J Infect Dis 133:302-309.
61. Stacy S, Pasquali A, Sexton V L, Cantwell A M, Kraig E, Dube P H. 2008. An age-old paradigm challenged: old baboons generate vigorous humoral immune responses to LcrV, a plague antigen. J Immunol 181:109-115.
62. Byvalov A A, Pautov V N, Chicherin Iu V, Lebedinskii V A, Evtigneev V I. 1984. Effectiveness of revaccinating hamadryas baboons with NISS live dried plague vaccine and fraction I of the plague microbe. Zh Mikrobiol Epidemiol Immunobiol 4:74-76.
63. Ransom J P, Krueger A P. 1954. Chronic pneumonic plague in Macaca mulatta. Am J Trop Med Hyg 3:1040-1054.
64. Finegold M J, Petery R F, Berendt R F, Adams H R. 1968. Studies on the pathogenesis of plague: blood coagulation and tissue responses of Macaca mulatta following exposure to aerosols of Pasteurella pestis. Am J Pathol 53:99-114.
65. Van Andel R, Sherwood R, Gennings C, Lyons C R, Hutt J, Gigliotti A, Barr E. 2008. Clinical and pathologic features of cynomolgus macaques (Macaca fascicularis) infected with aerosolized Yersinia pestis. Comp Med 58:68-75.
66. Williamson E D, Flick-Smith H C, Waters E, Miller J, Hodgson I, Le Butt C S, Hill J. 2007. Immunogenicity of the rF1+rV vaccine for plague with identification of potential immune correlates. Microb Pathog 42:11-21.
67. Mett V, Lyons J, Musiychuk K, Chichester J A, Brasil T, Couch R, Sherwood R, Palmer G A, Streatfield S J, Yusibov V. 2007. A plant-produced plague vaccine candidate confers protection to monkeys. Vaccine 25:3014-3017.
68. Cornelius C A, Quenee L E, Overheim K A, Koster F, Brasel T L, Elli D, Ciletti N A, Schneewind O. 2008. Immunization with recombinant V10 protects cynomolgus macaques from lethal pneumonic plague. Infect Immun 76:5588-5597.
69. Welkos S, Norris S, Adamovicz J. 2008. Modified caspase-3 assay indicates correlation of caspase-3 activity with immunity of nonhuman primates to Yersinia pestis infection. Clin Vaccine Immunol 15:1134-1137.
70. Mizel S B, Graff A H, Sriranganathan N, Ervin S, Lees C J, Lively M O, Hantgan R R, Thomas M J, Wood J, Bell B. 2009. Flagellin-F1-V fusion protein is an effective plague vaccine in mice and two species of nonhuman primates. Clin Vaccine Immunol 16:21-28.
71. Koster F, Perlin D S, Park S, Brasel T, Gigliotti A, Barr E, Myers L, Layton R C, Sherwood R, Lyons C R. 2010. Milestones in progression of primary pneumonic plague in cynomolgus macaques. Infect Immun 78:2946-2955.
72. Fellows P, Price J, Martin S, Metcalfe K, Krile R, Barnewall R, Hart M K, Lockman H. 2015. Characterization of a Cynomolgus Macaque Model of Pneumonic Plague for Evaluation of Vaccine Efficacy. Clin Vaccine Immunol 22:1070-1078.

73. Pitt M L. Non-human primates as a model for pneumonic plague. 2004. In: Animal Models and Correlates of Protection for Plague Vaccines Workshop.
74. Barouch D H, Pau M G, Custers J H, Koudstaal W, Kostense S, Havenga M J, Truitt D M, Sumida S M, Kishko M G, Arthur J C, Korioth-Schmitz B, Newberg M H, Gorgone D A, Lifton M A, Panicali D L, Nabel G J, Letvin N L, Goudsmit J. 2004. Immunogenicity of recombinant adenovirus serotype 35 vaccine in the presence of pre-existing anti-Ad5 immunity. J Immunol 172:6290-6297.
75. Nanda A, Lynch D M, Goudsmit J, Lemckert A A, Ewald B A, Sumida S M, Truitt D M, Abbink P, Kishko M G, Gorgone D A, Lifton M A, Shen L, Carville A, Mansfield K G, Havenga M J, Barouch D H. 2005. Immunogenicity of recombinant fiber-chimeric adenovirus serotype 35 vector-based vaccines in mice and rhesus monkeys. J Virol 79:14161-14168.
76. Zhang J, Jex E, Feng T, Sivko G S, Baillie L W, Goldman S, Van Kampen K R, Tang D C. 2013. An adenovirus-vectored nasal vaccine confers rapid and sustained protection against anthrax in a single-dose regimen. Clin Vaccine Immunol 20:1-8.
77. Croyle M A, Patel A, Tran K N, Gray M, Zhang Y, Strong J E, Feldmann H, Kobinger G P. 2008. Nasal delivery of an adenovirus-based vaccine bypasses pre-existing immunity to the vaccine carrier and improves the immune response in mice. PLoS One 3:e3548.
78. Xu Q, Pichichero M E, Simpson L L, Elias M, Smith L A, Zeng M. 2009. An adenoviral vector-based mucosal vaccine is effective in protection against botulism. Gene Ther 16:367-375.
79. Yu J R, Kim S, Lee J B, Chang J. 2008. Single intranasal immunization with recombinant adenovirus-based vaccine induces protective immunity against respiratory syncytial virus infection. J Virol 82:2350-2357.
80. Benner G E, Andrews G P, Byrne W R, Strachan S D, Sample A K, Heath D G, Friedlander A M. 1999. Immune response to Yersinia outer proteins and other Yersinia pestis antigens after experimental plague infection in mice. Infect Immun 67:1922-1928.
81. Andrews G P, Strachan S T, Benner G E, Sample A K, Anderson G W, Jr., Adamovicz J J, Welkos S L, Pullen J K, Friedlander A M. 1999. Protective efficacy of recombinant Yersinia outer proteins against bubonic plague caused by encapsulated and nonencapsulated Yersinia pestis. Infect Immun 67:1533-1537.
82. Tao P, Mahalingam M, Kirtley M L, van Lier C J, Sha J, Yeager L A, Chopra A K, Rao V B. 2013. Mutated and bacteriophage T4 nanoparticle arrayed F1-V immunogens from Yersinia pestis as next generation plague vaccines. PLoS Pathog 9:e1003495.
83. Jones F R, Gabitzsch E S, Xu Y, Balint J P, Borisevich V, Smith J, Peng B H, Walker A, Salazar M, Paessler S. 2011. Prevention of influenza virus shedding and protection from lethal H1N1 challenge using a consensus 2009 H1N1 H A and N A adenovirus vector vaccine. Vaccine 29:7020-7026.
84. Patel A, Zhang Y, Croyle M, Tran K, Gray M, Strong J, Feldmann H, Wilson J M, Kobinger G P. 2007. Mucosal delivery of adenovirus-based vaccine protects against Ebola virus infection in mice. J Infect Dis 196 Suppl 2:S413-420.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

SEQUENCE LISTING

<160> NUMBER OF SEQ ID NOS: 17

<210> SEQ ID NO 1
<211> LENGTH: 261
<212> TYPE: DNA
<213> ORGANISM: artificial

<220> FEATURE:
<223> OTHER INFORMATION: A nucleotide sequence encoding the YscF protein domain SEQ ID NO:2

<400> SEQUENCE: 1 atggctaatt tctccgggtt cacaaagggc actgacattg ccgatcttga tgccgttgcc 60 cagactctca agaagcctgc ggacgatgcc aacaaggcag taaatgattc catcgcagcc 120 ctgaaagaca agcctgacaa tccagcactc ttggccgacc tgcaacatag tatcaacaaa 180 tggtctgtaa tttacaatat aaactctacc attgtgcggt ccatgaaaga tctgatgcag 240 gggatcctgc aaaaatttcc c 261

<210> SEQ ID NO 2
<211> LENGTH: 87
<212> TYPE: PRT
<213> ORGANISM: artificial
<220> FEATURE:
<223> OTHER INFORMATION: An example of a YscF protein domain

<400> SEQUENCE: 2

Met Ala Asn Phe Ser Gly Phe Thr Lys Gly Thr Asp Ile Ala Asp Leu
1 5 10 15

Asp Ala Val Ala Gln Thr Leu Lys Lys Pro Ala Asp Asp Ala Asn Lys
20 25 30

Ala Val Asn Asp Ser Ile Ala Ala Leu Lys Asp Lys Pro Asp Asn Pro
35 40 45

Ala Leu Leu Ala Asp Leu Gln His Ser Ile Asn Lys Trp Ser Val Ile
50 55 60

Tyr Asn Ile Asn Ser Thr Ile Val Arg Ser Met Lys Asp Leu Met Gln
65 70 75 80

Gly Ile Leu Gln Lys Phe Pro
85

<210> SEQ ID NO 3
<211> LENGTH: 447
<212> TYPE: DNA
<213> ORGANISM: artificial
<220> FEATURE:
<223> OTHER INFORMATION: A nucleotide sequence encoding the mature F1 protein domain SEQ ID NO:4

<400> SEQUENCE: 3 gccgacctta cagctagtac cactgccaca gcaacgcttg tagagcctgc ccgaatcacc 60 ctgacgtata aggagggggc tccaatcaca ataatggaca atggaaacat cgataccgaa 120 ctgctggtgg ggaccctgac actgggtggc tacaagaccg gcacaacctc cacatccgtg 180 aacttcaccg acgccgccgg cgatcccatg tatctcacat tcacttcaca ggacggcaac 240 aatcatcagt tcaccactaa ggtgattggc aaggattcca gagacttcga catctctccc 300 aaggtgaatg gcgagaacct cgtgggggac gacgtggtac tggcaacagg ttcccaggat 360 ttctttgtcc ggtccattgg aagcaaaggg ggcaagctgg cagcaggaaa atacaccgac 420 gcagttacag tgactgtgtc aaaccag 447

<210> SEQ ID NO 4
<211> LENGTH: 149
<212> TYPE: PRT
<213> ORGANISM: artificial
<220> FEATURE:
<223> OTHER INFORMATION: An example of a mature F1 protein domain

<400> SEQUENCE: 4

Ala Asp Leu Thr Ala Ser Thr Thr Ala Thr Ala Thr Leu Val Glu Pro
1 5 10 15

Ala Arg Ile Thr Leu Thr Tyr Lys Glu Gly Ala Pro Ile Thr Ile Met
20 25 30

Asp Asn Gly Asn Ile Asp Thr Glu Leu Leu Val Gly Thr Leu Thr Leu
35 40 45

Gly Gly Tyr Lys Thr Gly Thr Thr Ser Thr Ser Val Asn Phe Thr Asp
50 55 60

Ala Ala Gly Asp Pro Met Tyr Leu Thr Phe Thr Ser Gln Asp Gly Asn
65 70 75 80

Asn His Gln Phe Thr Thr Lys Val Ile Gly Lys Asp Ser Arg Asp Phe
85 90 95

Asp Ile Ser Pro Lys Val Asn Gly Glu Asn Leu Val Gly Asp Asp Val
100 105 110

Val Leu Ala Thr Gly Ser Gln Asp Phe Phe Val Arg Ser Ile Gly Ser
115 120 125

Lys Gly Gly Lys Leu Ala Ala Gly Lys Tyr Thr Asp Ala Val Thr Val
130 135 140

Thr Val Ser Asn Gln
145

<210> SEQ ID NO 5
<211> LENGTH: 978
<212> TYPE: DNA
<213> ORGANISM: artificial
<220> FEATURE:
<223> OTHER INFORMATION: A nucleotide sequence encoding a LcrV protein
domain SEQ ID NO:6

<400> SEQUENCE: 5 atgatccgcg cctacgagca aaatcctcag cacttcattg aagaccttga gaaggtgcgc 60 gtggagcagc tcacaggcca cggtagcagt gtcctggagg agcttgtgca gctggtgaag 120 gacaagaata tcgatattag tataaaatac gatccaagga aagactctga ggtgttcgcg 180 aaccgcgtta ttaccgacga tattgaactc ctgaagaaaa tcctggccta ttttttgcca 240 gaggacgcta tcctgaaagg ggggcactat gataatcagc tccaaaatgg tatcaaacgg 300 gtgaaagagt tcctggagtc tagcccaaat actcagtggg agctgcgggc ctttatggct 360 gtgatgcact ttagtctgac agccgatcgg attgacgatg atatccttaa ggtgatcgtc 420 gatagcatga accatcatgg tgacgcaaga agtaaactga gggaggaact ggccgagctg 480 actgcagagc tcaaaatcta tagcgtcata caggccgaaa tcaataagca cttgagctca 540 tcaggcacca ttaacatcca cgacaagtcc attaatctga tggacaaaaa tctgtacgga 600 tataccgacg aggagatttt caaagcgtcc gccgagtata aaatcctcga gaaaatgcct 660 cagacaacta tacaggtgga tggttctgaa aaaaagattg tttctataaa ggacttcctc 720 gggtccgaga acaaaaggac cggcgcactg ggcaatctca agaactcata cagttataat 780 aaagataata atgagctttc ccattttgcc acaacctgct ccgacaaaag tagacctctg 840 aacgacctcg tgtcccaaaa gacaacacag ctgagtgata taacctccag gttcaactca 900 gcgatcgagg ctttgaacag gttcatccag aagtacgatt cagtgatgca gaggctgttg 960 gatgatacta gcggtaag 978

<210> SEQ ID NO 6
<211> LENGTH: 326
<212> TYPE: PRT
<213> ORGANISM: artificial
<220> FEATURE:
<223> OTHER INFORMATION: An example of a LcrV protein domain

<400> SEQUENCE: 6

```
Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325
```

<210> SEQ ID NO 7
<211> LENGTH: 1686
<212> TYPE: DNA
<213> ORGANISM: artificial

<220> FEATURE:
<223> OTHER INFORMATION: A nucleotide sequence encoding a fusion protein
domain SEQ ID NO:8

<400> SEQUENCE: 7 atggctaatt tctccgggtt cacaaagggc actgacattg ccgatcttga tgccgttgcc 60 cagactctca agaagcctgc ggacgatgcc aacaaggcag taaatgattc catcgcagcc 120 ctgaaagaca agcctgacaa tccagcactc ttggccgacc tgcaacatag tatcaacaaa 180 tggtctgtaa tttacaatat aaactctacc attgtgcggt ccatgaaaga tctgatgcag 240 gggatcctgc aaaaatttcc cgccgacctt acagctagta ccactgccac agcaacgctt 300 gtagagcctg cccgaatcac cctgacgtat aaggaggggg ctccaatcac aataatggac 360 aatggaaaca tcgataccga actgctggtg gggaccctga cactgggtgg ctacaagacc 420 ggcacaacct ccacatccgt gaacttcacc gacgccgccg gcgatcccat gtatctcaca 480 ttcacttcac aggacggcaa caatcatcag ttcaccacta aggtgattgg caaggattcc 540 agagacttcg acatctctcc caaggtgaat ggcgagaacc tcgtggggga cgacgtggta 600 ctggcaacag gttcccagga tttctttgtc cggtccattg gaagcaaagg gggcaagctg 660 gcagcaggaa aatacaccga cgcagttaca gtgactgtgt caaaccagat gatccgcgcc 720 tacgagcaaa atcctcagca cttcattgaa gaccttgaga aggtgcgcgt ggagcagctc 780 acaggccacg gtagcagtgt cctggaggag cttgtgcagc tggtgaagga caagaatatc 840 gatattagta taaaatacga tccaaggaaa gactctgagg tgttcgcgaa ccgcgttatt 900 accgacgata ttgaactcct gaagaaaatc ctggcctatt ttttgccaga ggacgctatc 960 ctgaaagggg ggcactatga taatcagctc caaaatggta tcaaacgggt gaaagagttc 1020 ctggagtcta gcccaaatac tcagtgggag ctgcgggcct ttatggctgt gatgcacttt 1080 agtctgacag ccgatcggat tgacgatgat atccttaagg tgatcgtcga tagcatgaac 1140 catcatggtg acgcaagaag taaactgagg gaggaactgg ccgagctgac tgcagagctc 1200 aaaatctata gcgtcataca ggccgaaatc aataagcact tgagctcatc aggcaccatt 1260 aacatccacg acaagtccat taatctgatg gacaaaaatc tgtacggata taccgacgag 1320 gagattttca aagcgtccgc cgagtataaa atcctcgaga aaatgcctca gacaactata 1380 caggtggatg gttctgaaaa aaagattgtt tctataaagg acttcctcgg gtccgagaac 1440 aaaaggaccg gcgcactggg caatctcaag aactcataca gttataataa agataataat 1500 gagctttccc attttgccac aacctgctcc gacaaaagta gacctctgaa cgacctcgtg 1560 tcccaaaaga caacacagct gagtgatata acctccaggt tcaactcagc gatcgaggct 1620 ttgaacaggt tcatccagaa gtacgattca gtgatgcaga ggctgttgga tgatactagc 1680 ggtaag 1686

<210> SEQ ID NO 8
<211> LENGTH: 562
<212> TYPE: PRT
<213> ORGANISM: artificial
<220> FEATURE:
<223> OTHER INFORMATION: An example of a fusion protein

<400> SEQUENCE: 8

Met Ala Asn Phe Ser Gly Phe Thr Lys Gly Thr Asp Ile Ala Asp Leu
1 5 10 15

Asp Ala Val Ala Gln Thr Leu Lys Lys Pro Ala Asp Asp Ala Asn Lys
20 25 30

```
Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro Ala Asp Leu Thr Ala Ser Thr Thr Ala
                85                  90                  95

Thr Ala Thr Leu Val Glu Pro Ala Arg Ile Thr Leu Thr Tyr Lys Glu
            100                 105                 110

Gly Ala Pro Ile Thr Ile Met Asp Asn Gly Asn Ile Asp Thr Glu Leu
        115                 120                 125

Leu Val Gly Thr Leu Thr Leu Gly Gly Tyr Lys Thr Gly Thr Thr Ser
    130                 135                 140

Thr Ser Val Asn Phe Thr Asp Ala Ala Gly Asp Pro Met Tyr Leu Thr
145                 150                 155                 160

Phe Thr Ser Gln Asp Gly Asn Asn His Gln Phe Thr Thr Lys Val Ile
                165                 170                 175

Gly Lys Asp Ser Arg Asp Phe Asp Ile Ser Pro Lys Val Asn Gly Glu
            180                 185                 190

Asn Leu Val Gly Asp Asp Val Val Leu Ala Thr Gly Ser Gln Asp Phe
        195                 200                 205

Phe Val Arg Ser Ile Gly Ser Lys Gly Gly Lys Leu Ala Ala Gly Lys
    210                 215                 220

Tyr Thr Asp Ala Val Thr Val Thr Val Ser Asn Gln Met Ile Arg Ala
225                 230                 235                 240

Tyr Glu Gln Asn Pro Gln His Phe Ile Glu Asp Leu Glu Lys Val Arg
                245                 250                 255

Val Glu Gln Leu Thr Gly His Gly Ser Ser Val Leu Glu Glu Leu Val
            260                 265                 270

Gln Leu Val Lys Asp Lys Asn Ile Asp Ile Ser Ile Lys Tyr Asp Pro
        275                 280                 285

Arg Lys Asp Ser Glu Val Phe Ala Asn Arg Val Ile Thr Asp Asp Ile
    290                 295                 300

Glu Leu Leu Lys Lys Ile Leu Ala Tyr Phe Leu Pro Glu Asp Ala Ile
305                 310                 315                 320

Leu Lys Gly Gly His Tyr Asp Asn Gln Leu Gln Asn Gly Ile Lys Arg
                325                 330                 335

Val Lys Glu Phe Leu Glu Ser Ser Pro Asn Thr Gln Trp Glu Leu Arg
            340                 345                 350

Ala Phe Met Ala Val Met His Phe Ser Leu Thr Ala Asp Arg Ile Asp
        355                 360                 365

Asp Asp Ile Leu Lys Val Ile Val Asp Ser Met Asn His His Gly Asp
    370                 375                 380

Ala Arg Ser Lys Leu Arg Glu Glu Leu Ala Glu Leu Thr Ala Glu Leu
385                 390                 395                 400

Lys Ile Tyr Ser Val Ile Gln Ala Glu Ile Asn Lys His Leu Ser Ser
                405                 410                 415

Ser Gly Thr Ile Asn Ile His Asp Lys Ser Ile Asn Leu Met Asp Lys
            420                 425                 430

Asn Leu Tyr Gly Tyr Thr Asp Glu Glu Ile Phe Lys Ala Ser Ala Glu
        435                 440                 445
```

```
Tyr Lys Ile Leu Glu Lys Met Pro Gln Thr Thr Ile Gln Val Asp Gly
    450                 455                 460

Ser Glu Lys Lys Ile Val Ser Ile Lys Asp Phe Leu Gly Ser Glu Asn
465                 470                 475                 480

Lys Arg Thr Gly Ala Leu Gly Asn Leu Lys Asn Ser Tyr Ser Tyr Asn
                485                 490                 495

Lys Asp Asn Asn Glu Leu Ser His Phe Ala Thr Thr Cys Ser Asp Lys
            500                 505                 510

Ser Arg Pro Leu Asn Asp Leu Val Ser Gln Lys Thr Thr Gln Leu Ser
        515                 520                 525

Asp Ile Thr Ser Arg Phe Asn Ser Ala Ile Glu Ala Leu Asn Arg Phe
    530                 535                 540

Ile Gln Lys Tyr Asp Ser Val Met Gln Arg Leu Leu Asp Asp Thr Ser
545                 550                 555                 560

Gly Lys


<210> SEQ ID NO 9
<211> LENGTH: 1776
<212> TYPE: DNA
<213> ORGANISM: artificial
<220> FEATURE:
<223> OTHER INFORMATION: A nucleotide sequence encoding a fusion protein
      including linkers SEQ ID NO:10

<400> SEQUENCE: 9

atggctaatt tctccgggtt cacaaagggc actgacattg ccgatcttga tgccgttgcc     60

cagactctca agaagcctgc ggacgatgcc aacaaggcag taaatgattc catcgcagcc    120

ctgaaagaca agcctgacaa tccagcactc ttggccgacc tgcaacatag tatcaacaaa    180

tggtctgtaa tttacaatat aaactctacc attgtgcggt ccatgaaaga tctgatgcag    240

gggatcctgc aaaaatttcc cgggggcggg ggttccgggg gaggcggtag tggcggcggt    300

ggatcagccg accttacagc tagtaccact gccacagcaa cgcttgtaga gcctgcccga    360

atcaccctga cgtataagga gggggctcca atcacaataa tggacaatgg aaacatcgat    420

accgaactgc tggtggggac cctgacactg ggtggctaca agaccggcac aacctccaca    480

tccgtgaact tcaccgacgc cgccggcgat cccatgtatc tcacattcac ttcacaggac    540

ggcaacaatc atcagttcac cactaaggtg attggcaagg attccagaga cttcgacatc    600

tctcccaagg tgaatggcga gaacctcgtg ggggacgacg tggtactggc aacaggttcc    660

caggatttct ttgtccggtc cattggaagc aaagggggca agctggcagc aggaaaatac    720

accgacgcag ttacagtgac tgtgtcaaac cagggaggcg gtggatccgg aggcggaggc    780

tcaggaggcg gggggagcat gatccgcgcc tacgagcaaa atcctcagca cttcattgaa    840

gaccttgaga aggtgcgcgt ggagcagctc acaggccacg gtagcagtgt cctggaggag    900

cttgtgcagc tggtgaagga caagaatatc gatattagta taaaatacga tccaaggaaa    960

gactctgagg tgttcgcgaa ccgcgttatt accgacgata ttgaactcct gaagaaaatc   1020

ctggcctatt ttttgccaga ggacgctatc ctgaaagggg ggcactatga taatcagctc   1080

caaaatggta tcaaacgggt gaaagagttc ctggagtcta gcccaaatac tcagtgggag   1140

ctgcgggcct ttatggctgt gatgcacttt agtctgacag ccgatcggat tgacgatgat   1200

atccttaagg tgatcgtcga tagcatgaac catcatggtg acgcaagaag taaactgagg   1260

gaggaactgg ccgagctgac tgcagagctc aaaatctata gcgtcataca ggccgaaatc   1320

aataagcact tgagctcatc aggcaccatt aacatccacg acaagtccat taatctgatg   1380
```

```
gacaaaaatc tgtacggata taccgacgag gagattttca aagcgtccgc cgagtataaa   1440

atcctcgaga aaatgcctca gacaactata caggtggatg gttctgaaaa aaagattgtt   1500

tctataaagg acttcctcgg gtccgagaac aaaaggaccg gcgcactggg caatctcaag   1560

aactcataca gttataataa agataataat gagctttccc attttgccac aacctgctcc   1620

gacaaaagta gacctctgaa cgacctcgtg tcccaaaaga caacacagct gagtgatata   1680

acctccaggt tcaactcagc gatcgaggct ttgaacaggt tcatccagaa gtacgattca   1740

gtgatgcaga ggctgttgga tgatactagc ggtaag                             1776
```

```
<210> SEQ ID NO 10
<211> LENGTH: 592
<212> TYPE: PRT
<213> ORGANISM: artificial
<220> FEATURE:
<223> OTHER INFORMATION: An example of a fusion protein including
      linkers

<400> SEQUENCE: 10

Met Ala Asn Phe Ser Gly Phe Thr Lys Gly Thr Asp Ile Ala Asp Leu
1               5                   10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Lys Pro Asp Asn Pro
        35                  40                  45

Ala Leu Leu Ala Asp Leu Gln His Ser Ile Asn Lys Trp Ser Val Ile
    50                  55                  60

Tyr Asn Ile Asn Ser Thr Ile Val Arg Ser Met Lys Asp Leu Met Gln
65                  70                  75                  80

Gly Ile Leu Gln Lys Phe Pro Gly Gly Gly Gly Ser Gly Gly Gly Gly
                85                  90                  95

Ser Gly Gly Gly Gly Ser Ala Asp Leu Thr Ala Ser Thr Thr Ala Thr
            100                 105                 110

Ala Thr Leu Val Glu Pro Ala Arg Ile Thr Leu Thr Tyr Lys Glu Gly
        115                 120                 125

Ala Pro Ile Thr Ile Met Asp Asn Gly Asn Ile Asp Thr Glu Leu Leu
    130                 135                 140

Val Gly Thr Leu Thr Leu Gly Gly Tyr Lys Thr Gly Thr Thr Ser Thr
145                 150                 155                 160

Ser Val Asn Phe Thr Asp Ala Ala Gly Asp Pro Met Tyr Leu Thr Phe
                165                 170                 175

Thr Ser Gln Asp Gly Asn Asn His Gln Phe Thr Thr Lys Val Ile Gly
            180                 185                 190

Lys Asp Ser Arg Asp Phe Asp Ile Ser Pro Lys Val Asn Gly Glu Asn
        195                 200                 205

Leu Val Gly Asp Asp Val Val Leu Ala Thr Gly Ser Gln Asp Phe Phe
    210                 215                 220

Val Arg Ser Ile Gly Ser Lys Gly Gly Lys Leu Ala Ala Gly Lys Tyr
225                 230                 235                 240

Thr Asp Ala Val Thr Val Thr Val Ser Asn Gln Gly Gly Gly Gly Ser
                245                 250                 255

Gly Gly Gly Gly Ser Gly Gly Gly Gly Ser Met Ile Arg Ala Tyr Glu
            260                 265                 270

Gln Asn Pro Gln His Phe Ile Glu Asp Leu Glu Lys Val Arg Val Glu
        275                 280                 285
```

```
Gln Leu Thr Gly His Gly Ser Ser Val Leu Glu Glu Leu Val Gln Leu
    290                 295                 300

Val Lys Asp Lys Asn Ile Asp Ile Ser Ile Lys Tyr Asp Pro Arg Lys
305                 310                 315                 320

Asp Ser Glu Val Phe Ala Asn Arg Val Ile Thr Asp Asp Ile Glu Leu
                325                 330                 335

Leu Lys Lys Ile Leu Ala Tyr Phe Leu Pro Glu Asp Ala Ile Leu Lys
            340                 345                 350

Gly Gly His Tyr Asp Asn Gln Leu Gln Asn Gly Ile Lys Arg Val Lys
        355                 360                 365

Glu Phe Leu Glu Ser Ser Pro Asn Thr Gln Trp Glu Leu Arg Ala Phe
    370                 375                 380

Met Ala Val Met His Phe Ser Leu Thr Ala Asp Arg Ile Asp Asp Asp
385                 390                 395                 400

Ile Leu Lys Val Ile Val Asp Ser Met Asn His His Gly Asp Ala Arg
                405                 410                 415

Ser Lys Leu Arg Glu Glu Leu Ala Glu Leu Thr Ala Glu Leu Lys Ile
            420                 425                 430

Tyr Ser Val Ile Gln Ala Glu Ile Asn Lys His Leu Ser Ser Ser Gly
        435                 440                 445

Thr Ile Asn Ile His Asp Lys Ser Ile Asn Leu Met Asp Lys Asn Leu
    450                 455                 460

Tyr Gly Tyr Thr Asp Glu Glu Ile Phe Lys Ala Ser Ala Glu Tyr Lys
465                 470                 475                 480

Ile Leu Glu Lys Met Pro Gln Thr Thr Ile Gln Val Asp Gly Ser Glu
                485                 490                 495

Lys Lys Ile Val Ser Ile Lys Asp Phe Leu Gly Ser Glu Asn Lys Arg
            500                 505                 510

Thr Gly Ala Leu Gly Asn Leu Lys Asn Ser Tyr Ser Tyr Asn Lys Asp
        515                 520                 525

Asn Asn Glu Leu Ser His Phe Ala Thr Thr Cys Ser Asp Lys Ser Arg
    530                 535                 540

Pro Leu Asn Asp Leu Val Ser Gln Lys Thr Thr Gln Leu Ser Asp Ile
545                 550                 555                 560

Thr Ser Arg Phe Asn Ser Ala Ile Glu Ala Leu Asn Arg Phe Ile Gln
                565                 570                 575

Lys Tyr Asp Ser Val Met Gln Arg Leu Leu Asp Asp Thr Ser Gly Lys
            580                 585                 590


<210> SEQ ID NO 11
<211> LENGTH: 5
<212> TYPE: PRT
<213> ORGANISM: artificial
<220> FEATURE:
<223> OTHER INFORMATION: Linker

<400> SEQUENCE: 11

Gly Gly Gly Gly Ser
1               5


<210> SEQ ID NO 12
<211> LENGTH: 33
<212> TYPE: DNA
<213> ORGANISM: artificial
<220> FEATURE:
<223> OTHER INFORMATION: Primer
```

-continued

```
<400> SEQUENCE: 12

cacatatgag taacttctct ggatttacga aag                                33


<210> SEQ ID NO 13
<211> LENGTH: 31
<212> TYPE: DNA
<213> ORGANISM: artificial
<220> FEATURE:
<223> OTHER INFORMATION: Primer

<400> SEQUENCE: 13

cactcgagtg ggaacttctg taggatgcct t                                  31


<210> SEQ ID NO 14
<211> LENGTH: 30
<212> TYPE: DNA
<213> ORGANISM: artificial
<220> FEATURE:
<223> OTHER INFORMATION: Primer

<400> SEQUENCE: 14

cacatatgaa aaaaatcagt tccgttatcg                                    30


<210> SEQ ID NO 15
<211> LENGTH: 34
<212> TYPE: DNA
<213> ORGANISM: artificial
<220> FEATURE:
<223> OTHER INFORMATION: Primer

<400> SEQUENCE: 15

cactcgagtt ggttagatac ggttacggtt acag                               34


<210> SEQ ID NO 16
<211> LENGTH: 31
<212> TYPE: DNA
<213> ORGANISM: artificial
<220> FEATURE:
<223> OTHER INFORMATION: Primer

<400> SEQUENCE: 16

cacatatgat tagagcctac gaacaaaacc c                                  31


<210> SEQ ID NO 17
<211> LENGTH: 34
<212> TYPE: DNA
<213> ORGANISM: artificial
<220> FEATURE:
<223> OTHER INFORMATION: Primer

<400> SEQUENCE: 17

cagtcgactt taccagacgt gtcatctagc agac                               34
```

What is claimed is:

1. A method comprising:

administering a first composition to a subject by an intranasal route, wherein the first composition comprises a vector comprising a polynucleotide encoding a fusion protein, wherein the fusion protein comprises a YscF protein domain, a mature F1 protein domain, and a LcrV protein domain; and administering a second composition to the subject by an intramuscular route, wherein the second composition comprises the fusion protein, wherein the fusion protein is isolated, and wherein the intramuscular administration is after the intranasal administration.

2. The method of claim 1 wherein the fusion protein comprises at least one linker, wherein the linker is present between two of the domains.

3. The method of claim 1 wherein the fusion protein comprises a His-tag.

4. The method of claim 1 wherein the vector is a replication defective adenovirus vector.

5. The method of claim 4 wherein the defective adenovirus vector is type-5 (Ad5).

6. The method of claim 1 wherein the fusion protein comprises the YscF protein, the mature F1 protein, and the LcrV protein.

7. The method of claim 1 wherein the intramuscular administration is at least 7 days after the intranasal administration.

8. The method of claim 1 wherein the subject is a human.

9. The method of claim 1 wherein the administering confers immunity to plague caused by Yersinia pestis.

10. The method of claim 9 wherein the plague is pneumonic plague *or bubonic plague*.

*11. A method comprising:*

*administering a composition to a subject by an intranasal route,*

*wherein the composition comprises a vector comprising a polynucleotide encoding a fusion protein,*

*wherein the fusion protein comprises a YscF protein domain, a mature F1 protein domain, and a LcrV protein domain; and*

*administering a second administration of the composition to the subject by an intranasal route.*

*12. The method of claim 11 wherein the fusion protein comprises at least one linker, wherein the linker is present between two of the domains.*

*13. The method of claim 11 wherein the fusion protein comprises a His-tag.*

*14. The method of claim 11 wherein the vector is a replication defective adenovirus vector.*

*15. The method of claim 14 wherein the defective adenovirus vector is type-5 (Ad5).*

*16. The method of claim 11 wherein the fusion protein comprises the YscF protein, the mature F1 protein, and the LcrV protein.*

*17. The method of claim 11 wherein the subject is a human.*

*18. The method of claim 11 wherein the administering confers immunity to plague caused by Yersinia pestis.*

*19. The method of claim 18 wherein the plague is pneumonic plague or bubonic plague.*

* * * * *